(12) United States Patent
Nguyen

(10) Patent No.: US 8,545,633 B2
(45) Date of Patent: Oct. 1, 2013

(54) METHOD FOR PRODUCING ETHANOL AND CO-PRODUCTS FROM CELLULOSIC BIOMASS

(75) Inventor: Quang A. Nguyen, Chesterfield, MO (US)

(73) Assignee: Abengoa Bioenergy New Technologies, Inc., Chesterfield, MS (US)

( * ) Notice: Subject to any disclaimer, the term of this patent is extended or adjusted under 35 U.S.C. 154(b) by 7 days.

(21) Appl. No.: 13/236,272

(22) Filed: Sep. 19, 2011

(65) Prior Publication Data

US 2012/0006320 A1 Jan. 12, 2012

Related U.S. Application Data

(63) Continuation of application No. 13/056,074, filed as application No. PCT/US2010/046561 on Aug. 24, 2010.

(60) Provisional application No. 61/236,345, filed on Aug. 24, 2009.

(51) Int. Cl.
*D21C 1/00* (2006.01)

(52) U.S. Cl.
USPC .......................................................... 127/34

(58) Field of Classification Search
None
See application file for complete search history.

(56) References Cited

U.S. PATENT DOCUMENTS

| | | |
|---|---|---|
| 319,299 A | 6/1885 | Morgan |
| 459,113 A | 9/1891 | Rymal |
| 1,073,425 A | 9/1913 | Lamert |
| 1,106,736 A | 8/1914 | Schuler |
| 1,247,153 A | 11/1917 | Roberts |
| 1,560,855 A | 11/1925 | Queneau |
| 1,824,221 A | 9/1931 | Mason |
| 2,080,327 A | 5/1937 | McKinnis |
| 2,086,701 A | 7/1937 | Dreyfus |
| 2,263,608 A | 11/1941 | Brown |
| 2,333,739 A | 11/1943 | Puckett |
| 2,541,058 A | 2/1951 | Heritage et al. |
| 2,541,059 A | 2/1951 | Heritage et al. |

(Continued)

FOREIGN PATENT DOCUMENTS

| | | |
|---|---|---|
| CA | 1070537 | 1/1980 |
| CA | 1096374 B | 2/1981 |

(Continued)

OTHER PUBLICATIONS

Aden, A., et al., "Lignocellulosic Biomass to Ethanol Process Design and Economics Utilizing Co-Current Dilute Acid Prehydrolysis and Enzymatic Hydrolysis for Corn Stover," 2002, Technical Report published by National Renewable Energy Laboratory, 154 pages.

(Continued)

*Primary Examiner* — Patricia L Hailey
*Assistant Examiner* — Stefanie Cohen
(74) *Attorney, Agent, or Firm* — Armstrong Teasdale LLP

(57) ABSTRACT

The present invention generally relates to processes for production of ethanol from cellulosic biomass. The present invention also relates to production of various co-products of preparation of ethanol from cellulosic biomass. The present invention further relates to improvements in one or more aspects of preparation of ethanol from cellulosic biomass including, for example, improved methods for cleaning biomass feedstocks, improved acid impregnation, and improved steam treatment, or "steam explosion."

48 Claims, 4 Drawing Sheets

(56) References Cited

U.S. PATENT DOCUMENTS

| | | |
|---|---|---|
| 2,541,127 A | 2/1951 | Van Beckum |
| 2,570,042 A | 10/1951 | West |
| 2,595,827 A | 5/1952 | Boruff et al. |
| 2,615,883 A | 10/1952 | Sweeney et al. |
| 2,697,703 A | 12/1954 | Heritage et al. |
| 2,758,031 A | 8/1956 | Ozai-Durrani |
| 3,017,404 A | 1/1962 | Ball |
| 3,109,560 A | 11/1963 | Rosenleaf |
| 3,223,697 A | 12/1965 | Ball et al. |
| 3,357,437 A | 12/1967 | Maguire |
| 3,383,277 A | 5/1968 | Gordon et al. |
| 3,407,943 A | 10/1968 | Douglass, Jr. |
| 3,572,593 A | 3/1971 | Guarisco |
| 3,617,433 A | 11/1971 | Sutherland |
| 3,743,572 A | 7/1973 | Richter et al. |
| 3,817,826 A | 6/1974 | Hoye |
| 3,964,880 A | 6/1976 | Siegrist |
| 4,023,982 A | 5/1977 | Knauth |
| 4,055,673 A | 10/1977 | Mueller et al. |
| 4,062,304 A | 12/1977 | Herbold et al. |
| 4,119,025 A | 10/1978 | Brown |
| 4,136,207 A | 1/1979 | Bender |
| 4,160,695 A | 7/1979 | Dietrichs et al. |
| 4,181,796 A | 1/1980 | Dietrichs et al. |
| 4,186,658 A | 2/1980 | Brown |
| 4,196,827 A | 4/1980 | Leafdale |
| 4,200,692 A | 4/1980 | Puls et al. |
| 4,211,163 A | 7/1980 | Brown et al. |
| 4,237,226 A | 12/1980 | Grethlein |
| 4,281,934 A | 8/1981 | Krause et al. |
| 4,286,884 A | 9/1981 | Retrum |
| 4,296,864 A | 10/1981 | Misaka et al. |
| 4,316,748 A | 2/1982 | Rugg et al. |
| 4,331,447 A | 5/1982 | Kamada et al. |
| 4,341,353 A | 7/1982 | Hamilton et al. |
| 4,364,667 A | 12/1982 | Reiner |
| 4,412,485 A | 11/1983 | Brown |
| 4,427,453 A | 1/1984 | Reitter |
| 4,432,805 A | 2/1984 | Nuuttila et al. |
| 4,436,586 A | 3/1984 | Elmore |
| 4,451,567 A | 5/1984 | Ishibashi et al. |
| 4,461,648 A | 7/1984 | Foody |
| 4,470,851 A | 9/1984 | Paszner et al. |
| 4,483,625 A | 11/1984 | Fisher |
| 4,511,433 A | 4/1985 | Tournier et al. |
| 4,584,057 A | 4/1986 | Rowe et al. |
| 4,600,590 A | 7/1986 | Dale |
| 4,615,742 A | 10/1986 | Wright |
| 4,645,541 A | 2/1987 | Delong |
| 4,667,373 A | 5/1987 | Roder |
| 4,670,944 A | 6/1987 | Thrash |
| 4,676,363 A | 6/1987 | Buchmuller et al. |
| 4,746,404 A | 5/1988 | Laakso |
| 4,751,034 A | 6/1988 | Delong et al. |
| 4,752,579 A | 6/1988 | Arena et al. |
| 4,764,596 A | 8/1988 | Lora et al. |
| 4,775,239 A | 10/1988 | Martinek et al. |
| 4,798,651 A | 1/1989 | Kokta |
| 4,822,737 A | 4/1989 | Saida |
| 4,867,846 A | 9/1989 | Fleck |
| 4,869,786 A | 9/1989 | Hanke |
| 4,908,098 A | 3/1990 | DeLong et al. |
| 4,908,099 A | 3/1990 | Delong |
| 4,911,558 A | 3/1990 | Teske |
| 4,947,743 A | 8/1990 | Brown et al. |
| 4,966,650 A | 10/1990 | Delong et al. |
| 4,997,488 A | 3/1991 | Gould et al. |
| 5,012,731 A | 5/1991 | Maisonneuve |
| 5,023,097 A | 6/1991 | Tyson |
| 5,034,099 A | 7/1991 | Nilsson |
| 5,047,332 A | 9/1991 | Chahal |
| 5,052,874 A | 10/1991 | Johanson |
| 5,100,066 A | 3/1992 | Frei |
| 5,114,488 A | 5/1992 | Huber et al. |
| 5,122,228 A | 6/1992 | Bouchette et al. |
| 5,135,861 A | 8/1992 | Pavilon |
| 5,176,295 A | 1/1993 | Stefanik |
| 5,181,804 A | 1/1993 | Wysong et al. |
| 5,188,298 A | 2/1993 | Gerber |
| 5,198,074 A | 3/1993 | Villavicencio et al. |
| 5,221,357 A | 6/1993 | Brink |
| 5,338,366 A | 8/1994 | Grace et al. |
| 5,348,871 A | 9/1994 | Scott et al. |
| 5,366,558 A | 11/1994 | Brink |
| 5,411,594 A | 5/1995 | Brelsford |
| 5,424,417 A | 6/1995 | Torget et al. |
| 5,487,989 A | 1/1996 | Fowler et al. |
| 5,503,996 A | 4/1996 | Torget et al. |
| 5,504,259 A | 4/1996 | Diebold et al. |
| 5,536,325 A | 7/1996 | Brink |
| 5,571,703 A | 11/1996 | Chieffalo et al. |
| 5,597,714 A | 1/1997 | Farone et al. |
| 5,611,930 A | 3/1997 | Nguyen et al. |
| 5,628,830 A | 5/1997 | Brink |
| 5,677,154 A | 10/1997 | Van Draanen et al. |
| 5,705,216 A | 1/1998 | Tyson |
| 5,705,369 A | 1/1998 | Torget et al. |
| 5,730,837 A | 3/1998 | Black et al. |
| 5,733,758 A | 3/1998 | Nguyen |
| 5,735,916 A | 4/1998 | Lucas et al. |
| 5,791,779 A | 8/1998 | Smith, Sr. |
| 5,843,760 A | 12/1998 | Zhang et al. |
| 5,863,389 A | 1/1999 | White et al. |
| 5,916,780 A | 6/1999 | Foody et al. |
| 5,932,452 A | 8/1999 | Mustranta et al. |
| 6,022,419 A | 2/2000 | Torget et al. |
| 6,063,204 A | 5/2000 | Hester et al. |
| 6,090,595 A | 7/2000 | Foody et al. |
| 6,199,299 B1 | 3/2001 | Prough et al. |
| 6,228,177 B1 | 5/2001 | Torget |
| 6,330,767 B1 | 12/2001 | Carr et al. |
| 6,336,573 B1 | 1/2002 | Johanson |
| 6,409,841 B1 | 6/2002 | Lombard |
| 6,419,788 B1 | 7/2002 | Wingerson |
| 6,423,145 B1 * | 7/2002 | Nguyen et al. .................. 127/37 |
| 6,498,029 B2 | 12/2002 | Keller, Jr. et al. |
| 6,557,267 B2 | 5/2003 | Wanger |
| 6,569,653 B1 | 5/2003 | Alard et al. |
| 6,572,734 B2 | 6/2003 | Baker |
| 6,620,292 B2 | 9/2003 | Wingerson |
| 6,660,506 B2 | 12/2003 | Nguyen et al. |
| 6,737,258 B2 | 5/2004 | Hames et al. |
| 6,743,928 B1 | 6/2004 | Zeitsch |
| 6,927,048 B2 | 8/2005 | Verser et al. |
| 7,178,698 B2 | 2/2007 | Forslund et al. |
| 7,198,925 B2 | 4/2007 | Foody |
| 7,238,242 B2 | 7/2007 | Pinatti et al. |
| 7,445,691 B2 | 11/2008 | Snekkenes et al. |
| 7,494,675 B2 | 2/2009 | Abbas et al. |
| 7,503,981 B2 | 3/2009 | Wyman et al. |
| 7,598,069 B2 | 10/2009 | Felby et al. |
| 7,842,490 B2 | 11/2010 | Felby et al. |
| 7,937,851 B2 | 5/2011 | Rajagopalan et al. |
| 7,943,350 B2 | 5/2011 | Vlasenko et al. |
| 7,976,259 B2 | 7/2011 | Craig et al. |
| 8,287,651 B2 | 10/2012 | Benson |
| 2002/0003032 A1 | 1/2002 | Nay et al. |
| 2002/0164730 A1 * | 11/2002 | Ballesteros Perdices et al. ............................. 435/163 |
| 2002/0164731 A1 | 11/2002 | Eroma et al. |
| 2004/0121436 A1 | 6/2004 | Blount |
| 2004/0154760 A1 | 8/2004 | Dean |
| 2004/0171136 A1 | 9/2004 | Holtzapple et al. |
| 2004/0231661 A1 | 11/2004 | Griffin et al. |
| 2004/0231811 A1 | 11/2004 | Engstrand et al. |
| 2005/0269048 A1 | 12/2005 | Rodriguez et al. |
| 2006/0088922 A1 | 4/2006 | Yang et al. |
| 2006/0163118 A1 | 7/2006 | Kelsey et al. |
| 2006/0169430 A1 | 8/2006 | Tarasenko |
| 2006/0188965 A1 | 8/2006 | Wyman et al. |
| 2006/0233864 A1 | 10/2006 | Power |
| 2006/0272518 A1 | 12/2006 | Babbini |
| 2006/0275895 A1 | 12/2006 | Jensen et al. |
| 2007/0037267 A1 | 2/2007 | Lewis et al. |

| | | | |
|---|---|---|---|
| 2007/0148751 A1 | 6/2007 | Griffin et al. | |
| 2007/0209974 A1 | 9/2007 | Lees | |
| 2007/0215300 A1 | 9/2007 | Upfal et al. | |
| 2007/0218530 A1 | 9/2007 | Duck et al. | |
| 2007/0227063 A1 | 10/2007 | Dale et al. | |
| 2008/0026431 A1 | 1/2008 | Saito et al. | |
| 2008/0038784 A1 | 2/2008 | D'Arnaud-Taylor | |
| 2008/0227161 A1 | 9/2008 | Levie et al. | |
| 2009/0029432 A1 | 1/2009 | Abbas et al. | |
| 2009/0062516 A1 | 3/2009 | Belanger et al. | |
| 2009/0069550 A1 | 3/2009 | Belanger et al. | |
| 2009/0098616 A1 | 4/2009 | Burke et al. | |
| 2009/0098617 A1 | 4/2009 | Burke et al. | |
| 2009/0240088 A1 | 9/2009 | Fenton et al. | |
| 2009/0246848 A1 | 10/2009 | Noel | |
| 2010/0024806 A1 | 2/2010 | Burke et al. | |
| 2010/0024807 A1 | 2/2010 | Burke et al. | |
| 2010/0024808 A1 | 2/2010 | Burke et al. | |
| 2010/0024809 A1 | 2/2010 | Burke et al. | |
| 2010/0028089 A1 | 2/2010 | Burke et al. | |
| 2010/0055747 A1 | 3/2010 | Kelemen et al. | |
| 2010/0124583 A1 | 5/2010 | Medoff | |
| 2010/0159552 A1 | 6/2010 | Benson et al. | |
| 2010/0181034 A1 | 7/2010 | Bradt et al. | |
| 2010/0186735 A1 | 7/2010 | Burke et al. | |
| 2010/0186736 A1 | 7/2010 | Burke et al. | |
| 2010/0200806 A1 | 8/2010 | Medoff et al. | |
| 2010/0255554 A1 | 10/2010 | Benson et al. | |
| 2010/0263814 A1 | 10/2010 | Dottori et al. | |
| 2010/0269990 A1 | 10/2010 | Dottori et al. | |
| 2010/0313882 A1 | 12/2010 | Dottori et al. | |
| 2011/0011391 A1 | 1/2011 | Burke | |
| 2011/0287498 A1 | 11/2011 | Medoff et al. | |
| 2011/0308141 A1 | 12/2011 | Christensen | |
| 2012/0138546 A1 | 6/2012 | Bonanni et al. | |
| 2012/0142068 A1 | 6/2012 | Medoff | |

FOREIGN PATENT DOCUMENTS

| | | |
|---|---|---|
| CA | 1147105 A | 5/1983 |
| CA | 1173825 A | 9/1984 |
| CA | 1190923 A | 7/1985 |
| CA | 1267407 B | 4/1990 |
| CA | 1287705 C | 8/1991 |
| CA | 2037275 A1 | 8/1992 |
| CA | 1322366 C | 9/1993 |
| CA | 2063547 A1 | 9/1993 |
| CA | 2065939 A1 | 10/1993 |
| CA | 2339002 A1 | 2/2000 |
| EP | 0487793 A1 | 6/1992 |
| EP | 0884391 B1 | 1/2002 |
| EP | 1316620 A2 | 6/2003 |
| EP | 1036236 B1 | 7/2003 |
| EP | 2198035 B1 | 6/2010 |
| FR | 777824 | 3/1935 |
| GB | 892506 | 3/1962 |
| WO | 9213849 A1 | 8/1992 |
| WO | 9640970 A1 | 12/1996 |
| WO | 9732073 A1 | 9/1997 |
| WO | 0078446 A2 | 12/2000 |
| WO | 0132715 A1 | 5/2001 |
| WO | 0212529 A1 | 2/2002 |
| WO | 0238787 A2 | 5/2002 |
| WO | 2004018645 A2 | 3/2004 |
| WO | 2004081193 A2 | 9/2004 |
| WO | 2004106624 A1 | 12/2004 |
| WO | 2005079190 A2 | 9/2005 |
| WO | 2005118165 A1 | 12/2005 |
| WO | 2006017655 A3 | 2/2006 |
| WO | 2006034591 A1 | 4/2006 |
| WO | 2006055362 A1 | 5/2006 |
| WO | 2006063467 A1 | 6/2006 |
| WO | 2007009463 A2 | 1/2007 |
| WO | 2007065241 A1 | 6/2007 |
| WO | 2007111605 A2 | 10/2007 |
| WO | 2008086115 A2 | 7/2008 |
| WO | 2008144903 A1 | 12/2008 |
| WO | 2009012779 A2 | 1/2009 |
| WO | 2009018469 A1 | 2/2009 |
| WO | 2009089439 A1 | 7/2009 |
| WO | 2010009547 A1 | 1/2010 |
| WO | 2010009548 A1 | 1/2010 |
| WO | 2010009549 A1 | 1/2010 |
| WO | 2010009550 A1 | 1/2010 |
| WO | 2010009551 A1 | 1/2010 |
| WO | 2010083600 A1 | 7/2010 |
| WO | 2010083601 A1 | 7/2010 |
| WO | 2011028554 A1 | 3/2011 |

OTHER PUBLICATIONS

Al-Halaly, A.S.M., "A Study of Some Anatomical Chemical Properties and Specific Gravity of Casuarina Equisetifolia Forst. Wood Grown in Iraq," 1985, AGRIS Record No. IQ8500239, Abstract, 1 page.

Antongiovanni, M., et al., "Variability in Chemical Composition of Straws," 1991, CIHEAM—Options Mediterraneennes, Serie Seminaires, 16:49-53.

Awafo, V.A., et al., "Evaluation of Combination Treatments of Sodium Hydroxide and Steam Explosion for the Production of Cellulase-Systems by Two T. reesei Mutants Under Solid-State Fermentation Conditions," 2000, Bioresource Tech, 73:235-245.

Azadbakht, M., et al., "Preparation of Lignin From Wood Dust as Vanillin Source and Comparison of Different Extraction Methods," Oct. 2004, Int J of Biol and Biotech, 1/4:535-537, Abstract Only, 1 page.

Ballerini, D., et al., "Ethanol Production from Lignocellulosics: Large Scale Experimentation and Economics," 1994, Bioresource Technology, 50:17-23.

Bigelow, M., et al., "Cellulase Production on Bagasse Pretreated with Hot Water," 2002, App Biochem and Biotech, 98-100:921-934.

Brownell, H.H., et al., "Steam-Explosion Pretreatment of Wood: Effect of Chip Size, Acid, Moisture Content and Pressure Drop," 1986, Biotechnol Bioeng, 28/6:792-801, Abstract Only, 1 page.

Coons, R., "DSM Launches Cellulosic Biofuel Project," Oct. 27, 2008, Chemical Week, 170/33:9.

Coons, R., "Novozymes Ramps Up Focus on Second-Generation Biofuels," Oct. 27, 2008, Chemical Week, 170/33:30.

Cullis, I.F., et al., "Effect of Initial Moisture Content and Chip Size on the Bioconversion Efficiency of Softwood Lignocellulosics," 2004, Biotechnol Bioeng, 85/4:413-421, Abstract Only, 1 page.

Cunningham, R.L., et al., "Improved Hemicellulose Recovery From Wheat Straw," 1985, Biotech and Bioeng Symp No. 15, Seventh Symposium on Biotechnology for Fuels and Chemicals, pp. 17-26.

Dasari, R.K., et al., "The Effect of Particle Size on Hydrolysis Reaction Rates and Rheological Properties in Cellulosic Slurries," 2007, Appl Biochem and Biotech, Session 2, 137-140/1-2, 289-299, Abstract Only.

Dowe, N., et al., "SSF Experimental Protocols-Lignocellulosic Biomass Hydrolysis and Fermentation, Laboratory Analytical Procedure (LAP)," Jan. 2008, NREL Technical Report, NREL/TP-510-42630, 19 pages.

Duff, S.J.B., et al., "Bioconversion of Forest Products Industry Waste Cellulosics to Fuel Ethanol: A Review", 1996, Bioresource Technology, 55:1-33.

Eggeman, T., et al., "Process and Economics Analysis of Pretreatment Technologies," 2005, Bioresource Technology, 96:2019-2025.

Emert, G.H., et al., "Gasohol/Biomass Developments: Economic Update of the Gulf Cellulose Alcohol Process," 1980, Chemical Engineering Progress, 76/9:47-52.

Flint, S.I., et al., "Recovery of Lignin During Nonstarch Polysaccharide Analysis," 1992, Cereal Chem, 69/4:444-447.

Foody, P., "Optimization of Steam Explosion Pretreatment," 1980, Final Report to DOE, Report No. DOE/ET23050-1, Contract No. AC02-79ET23050, Bibliographic Citation, 1 page.

Hames, B., et al., "Determination of Protein Content in Biomass, Laboratory Analytical Procedure (LAP)," May 2008, NREL Technical Report, NREL/TP-510-42625, 8 pages.

Hames, B., et al., "Preparation of Samples for Compositional Analysis, Laboratory Analytical Procedure (LAP)," Aug. 2008, NREL Technical Report, NREL/TP-510-42620, 12 pages.

Juhasz, T., et al., "Characterization of Cellulases and Hemicellulases Produced by Trichoderma reesei on Various Carbon Sources," 2005, Process Biochem, 40:3519-3525.

Katzen, R., et al., "Wood Hydrolysis. A Continuous Process," 1942, Industrial and Engineering Chemistry 34/3:314-322.

Kazi, K.M.F., et al., "Preimpregnation: An Important Step for Biomass Refining Processes," 1998, Biomass and Bioenergy, 15/2:125-141.

Keller, F.A., et al., "Yeast Adaptation on Softwood Prehydrolysate," 1998, Appl Biochem and Biotech, 70-72:137-148.

Kim, K.H. et al., "Continuous Countercurrent Extraction of Hemicellulose from Pretreated Wood Residues," 2001, Appl Biochem and Biotech, 91-93:253-267.

Kim, S.B., et al., "Diffusion of Sulfuric Acid within Lignocellulosic Biomass Particles and Its Impact on Dilute-Acid Pretreatment," 2002, Bioresource Technology 83:165-171.

Knappert, D., et al., "Partial Acid Hydrolysis of Cellulosic Materials as a Pretreatment for Enzymatic Hydrolysis," 1980, Biotech and Bioeng, 22:1449-1463.

Kolar, L., et al., "Agrochemical Value of Organic Matter of Fermenter Wastes in Biogas Production," 2008, Plant Soil Environ, 54/8:321-328.

Kotrba, R., "The Project of a Lifetime," Feb. 2006, Ethanol Producer Magazine, as republished in Biomassmagazine.com, 3 pages.

Kumar, R., et al., "The Impact of Dilute Sulfuric Acid on the Selectivity of Xylooligomer Depolymerization to Monomers," 2008, Carbohydrate Res, 343:290-300.

Linde, M., et al., "Steam Pretreatment of Acid-Sprayed and Acid-Soaked Barley Straw for Production of Ethanol," 2006, Appl Biochem and Biotech, 129-132:546-562.

Mosier, N., et al., "Features of Promising Technologies for Pretreatment of Lignocellulosic Biomass," 2005, Bioresource Technology, 96:673-686.

Nguyen, Q.A., et al., "NREL/DOE Ethanol Pilot-Plant: Current Status and Capabilities," 1996, Bioresource Technology, 58:189-196.

Nguyen, Q.A., et al., "Dilute Acid Pretreatment of Softwoods," 1998, Appl Biochem and Biotech, 70-72:77-87.

Nguyen, Q.A., et al., "Dilute Acid Hydrolysis of Softwoods", 1999, Appl Biochem and Biotech 77-79:133-142.

Nguyen, Q.A., et al., "Two-Stage Dilute-Acid Pretreatment of Softwoods," 2000, Appl Biochem and Biotech, 84-86:561-576.

Ohgren, K., et al., "High Temperature Enzymatic Prehydrolysis Prior to Simultaneous Saccharification and Fermentation of Steam Pretreated Corn Stover for Ethanol Production," 2007, Enzyme Microb Technol, 40/4:607-613.

Overend, R.P., et al., "Fractionation of Lignocellulosics by Steam-Aqueous Pretreatments," 1987, Phil Trans R Soc Lond A, 321:523-536.

Pan, X., et al., "Bioconversion of Hybrid Poplar to Ethanol and Co-Products Using an Organosolv Fractionation Process: Optimization of Process Yields," 2006, Biotech and Bioeng, 94/5:851-861.

Ramsay, J.A., et al., "Biological Conversion of Hemicellulose to Propionic Acid," 1998, Enzyme Microb Technol, 22:292-295.

Schell, D.J., et al., "Dilute-Sulfuric Acid Pretreatment of Corn Stover in Pilot-Scale Reactor," 2003, Appl Biochem and Biotech, 105-108:69-85.

Schell, D.J., et al., "A Bioethanol Process Development Unit: Initial Operating Experiences and Results with a Corn Fiber Feedstock," 2004, Bioresource Technol, 91:179-188.

Sharma-Shivappa, R.R., et al, "Conversion of Cotton Wastes to Bioenergy and Value-Added Products," 2008, Transactions of the ASABE, 51/6:2239-2246.

Sluiter, A., et al., "Determination of Ash in Biomass, Laboratory Analytical Procedure (LAP)," NREL Technical Report, NREL/TP-510-42622, Jan. 2008, 8 pages.

Sluiter, A., et al., "Determination of Extractives in Biomass, Laboratory Analytical Procedure (LAP)," NREL Technical Report, NREL/TP-510-42619, Jan. 2008, 12 pages.

Sluiter, A., et al., "Determination of Sugars, Byproducts, and Degradation Products in Liquid Fraction Process Samples, Laboratory Analytical Procedure (LAP)," NREL Technical Report, NREL/TP-510-42623, Jan. 2008, 14 pages.

Sluiter, A., et al., "Determination of Total Solids in Biomass and Total Dissolved Solids in Liquid Process Samples, Laboratory Analytical Procedure (LAP)," NREL Technical Report, NREL/TP-510-42621, Mar. 2008, 9 pages.

Sluiter, A., et al., "Determination of Structural Carbohydrates and Lignin in Biomass, Laboratory Analytical Procedure (LAP)," NREL Technical Report, NREL/TP-510-42618, Apr. 2008, 16 pages.

Sun, L., "Silicon-Based Materials from Rice Husks and Their Applications," 2001, Ind Eng Chem Res, 40/25:5861-5877, Abstract Only, 1 page.

Supplementary European Search Report issued in related European Application No. 10814265, dated Jun. 18, 2012.

International Search Report and the Written Opinion issued in PCT Application No. PCT/US2012/022552, dated May 15, 2012, 18 pages.

International Search Report and the Written Opinion issued in PCT Application No. PCT/CA2009/001034, dated Oct. 20, 2009, 9 pages.

Taherzadeh, M. J. et al., "Pretreatment of Lignocellulosic Wastes to Improve Ethanol and Biogas Production: A Review," 2008, Int. J. Mol. Sci., (9) 1621-1651.

Bakker, R. R., et al., "Biofuel Production from Acid-Impregnated Willow and Switchgrass," 2nd World Conference on Biomass for Energy, Industry and Climate Protection, May 10-14, 2004, Rome, Italy, pp. 1467-1470.

Thompson, D.N., et al., "Post-Harvest Processing Methods for Reduction of Silica and Alkali Metals in Wheat Straw," 2002, 24th Symposium on Biotechnology for Fuels and Chemicals, Poster #1-30, 21 pages.

Tucker, M.P., et al, "Comparison of Yellow Poplar Pretreatment Between NREL Digester and Sunds Hydrolyzer," 1998, Appl Biochem and Biotech, 70-72:25-35.

Tucker, M.P., et al, "Effects of Temperature and Moisture on Dilute-Acid Steam Explosion Pretreatment of Corn Stover and Cellulase Enzyme Digestibility," 2003, Appl Biochem and Biotech, 105-108:165-177.

Tucker, M.P., et al, "Conversion of Distiller's Grain into Fuel Alcohol and a Higher-Value Animal Feed by Dilute-Acid Pretreament," 2004, Appl Biochem and Biotech, 113-116:1139-1159.

Viamajala, S., et al., "Catalyst Transport in Corn Stover Internodes," 2005, Appl Biochem and Biotech, 129-132:509-527.

Wyman, C.E., et al., "Comparative Sugar Recovery Data from Laboratory Scale Application of Leading Pretreatment Technologies to Corn Stover," 2005, Bioresource Technology, 96:2026-2032.

Wyman, C.E., "Coordinated Development of Leading Biomass Pretreatment Technologies," 2005, Bioresource Technology 96:1959-1966.

Yang, B., et al., "Chapter 6. Unconventional Relationships for Hemicellulose Hydrolysis and Subsequent Cellulose Digestion," 2004, Lignocellulose Biodegradation, ACS Symposium Series 889, American Chemical Society, pp. 100-125.

On-Line Moisture Measurement and Control Manufacturing Industries Worldwide, Product Information, online: Process Sensors Corporation <http://processsensors.com/index.html?gclid=CKT27fXvJOCFREWagodclkUcw>, 2 pages, downloaded Dec. 30, 2011.

Metso Automation, Metso Automation's Newsletter for Neles and Jamesbury products, "Biofuels—a growth market for Metso", (Summer 2008), online: Metso <http://valveproducts.metso.com/metsoautomation/DocDB/catalogs/catalog.taf?pg_parent=397>, 11 pages.

SunOpta Inc., News Release, "SunOpta Announces Sale of Cellulosic Ethanol Facility to China Resources Alcohol Corporation," (Jun. 23, 2006), online: SunOpta Inc. <http://investor.sunopta.com/releasedetail.cfm?ReleaseID=287111>, 2 pages.

Buell Classifier Fisher-Klosterman, Leaflet, "Operation Principles and Efficiency," 2008, 4 pages.

Abengoa Bioenergy, Press Release, "Abengoa Bioenergy Awarded DOE Financial Assistance Agreement" (Feb.28, 2007), online: Abengoa Bioenergy <http://www.abengoabioenergy.com/corp/web/en/prensa/noticias/historico/2007/20071015_noticias.html>, 1 page.

Abengoa Bioenergy, Press Release, "Abengoa Bioenergy Opens Pilot Plant for the Energy of the Future" (Oct. 15, 2007), online: Abengoa Bioenergy <http://www.abengoabioenergy.com/corp/web/en/prensa/noticias/historico/2007/20071015_noticias.html>, 1 page.

Annual Report Under Section 13 or 15(d) of the Securities Exchange Act of 1934, for Bluefire Ethanol Fuels, Inc., U.S. Securities and Exchange Commission, Feb. 2008, 102 pages.

Annual Report Under Section 13 or (15)d of the Securities Exchange Act of 1934, for CleanTech Biofuels, Inc., U.S. Securities and Exchange Commission, Mar. 28, 2008, 78 pages.

"Building a Bridge to the Corn Ethanol Industry. Corn Stover to Ethanol at High Plains Corporation's York, Nebraska Co-Located Plant Site", Merrick & Company, Final Report of Jan., 2000, 17 pages.

"Clean Cities: Ethanol Basics" (Oct. 2008), NREL, U.S. Department of Energy, <http://www.afdc.energy.gov/afdc/pdfs/43835.pdf>, 6 pages.

"Fuel Ethanol: Background and Public Policy Issues", (Mar. 3, 2006), CRS Report for Congress, Yacobucci, B.D., online: U.S. Department of State, Foreign Press Centre <http://fpc.state.gov/documents/organization/62837.pdf>, 26 pages.

Kitani, O., et al., "Biomass Handbook," 1989, pp. 470-474 (Gordon and Breach Science Publishers: New York).

Wooley, R., et al., "Lignocellulosic Biomass to Ethanol Process Design and Economics Utilizing Co-Current Dilute Acid Prehydrolysis and Enzymatic Hydrolysis Current and Futuristic Scenarios," 1999, NREL Technical Report, TP-580-26157, 132 pages.

Moiser, N.S.,"Cellulosic Ethanol--Biofuel Beyond Corn," 2006, Bio Energy, ID-335, Purdue University, 4 pages.

Overend, R.P., "The Lignocellulosic Bottleneck: Material Properties, Architecture and Pretreatment", Slideshow, 25 pages, 2007.

Roberts, A.W., "Design Considerations and Performance Evaluation of Screw Conveyors", online: The South African Institute of Materials Handling <http://www.saimh.co.za/beltcon/beltcon11/beltcon1114.htm>, 11 pages, 2006.

"Ethanol Annual Report FY 1990", SERI, TP-231/3996, Prepared for the U.S. DOE, Jan. 1991, Contract No. DE-AC02-83CH10093, Texeira, R.H. and Goodman, B.J., editors, 344 pages.

"Ethanol Market Penetration," U.S. Department of Energy, Energy Efficiency & Renewable Energy, Alternative Fuels & Advanced Vehicles Data Center, online: U.S. Department of Energy <http://www.afdc.energy.gov/afdc/ethanol/market.html>, 2 pages.

Outputs from the EPOBIO Workshop, Greece, "Products from Plants—From Crops and Forests to Zero Waste Biorefineries", May 15-17, 2007, 49 pages.

"Process Design and Cost Estimate of Critical Equipment in the Biomass to Ethanol Process," Subcontract ACO-9-29067-01, Acid Hydrolysis Reactors Batch System, Report 99-10600/18, NREL, (Prepared by Harris Group Inc., Seattle, Washington, 2001), 36 pages.

"Research Advances: NREL Leads the Way", 2007, Cellulosic Ethanol, Brochure, NREL/BR-510-40742, Mar. 2007, online: National Renewable Energy Laboratory, <http://www.nrel.gov/biomass/pdfs/40742.pdf>, 8 pages.

"Softwood Biomass to Ethanol Feasibility Study, Final Report: Jun. 14, 1999," NREL/SR-510-27310, Aug. 2004, Subcontractor Report published by National Renewable Energy Laboratory, Merrick & Company, 122 pages.

"Fuel Ethanol Production", U.S. Department of Energy Office of Science, Genomics Science Program, archived website (2009): U.S. Department of Energy Office of Science <http://genomicscience.energy.gov/biofuels/ethanolproduction.shtml>, 6 pages.

International Search Report and the Written Opinion issued in connection with PCT Application No. PCT/CA2009/001035, dated Nov. 5, 2009, 7 pages.

International Search Report and the Written Opinion issued in connection with PCT Application No. PCT/CA2009/001036, dated Nov. 13, 2009, 6 pages.

International Search Report and the Written Opinion issued in connection with PCT Application No. PCT/US2010/46561, dated Dec. 20, 2010, 16 pages.

International Search Report and the Written Opinion issued in connection with PCT Application No. PCT/CA2010/000087, mailed on May 4, 2010, 10 pages.

International Search Report and the Written Opinion issued in connection with PCT Application No. PCT/CA2010/000088, mailed on May 14, 2010, 15 pages.

De Castro, F.B., "The Use of Steam Treatment to Upgrade Lignocellulosic Materials for Animal Feed," 1994, Thesis, University of Aberdeen, 214 pages.

Esteghlalian, A., et al., "Modeling and Optimization of the Dilute-Sulfuric-Acid Pretreatment of Corn Stover, Poplar and Switchgrass," 1997, Bioresource Technology, 59:129-136.

Fan, L.T., et al., "Evaluation of Pretreatments for Enzymatic Conversion of Agricultural Residues," 1981, Biotechnology & Bioengineering Symposium, 11:29-45 (Proceedings of the Third Symposium on Biotechnology in Energy Production and Conservation, Gatlinburg, TN, May 12-15, 1981).

Ghose, T.K., "Measurement of Cellulase Activities," 1987, Pure and Appl. Chem., 59/2:257-268.

Grethlein, H.E., et al., "Common Aspects of Acid Prehydrolysis and Steam Explosion for Pretreating Wood," 1991, Bioresource Technology, 36:77-82.

Grethlein, H.E., "Chemical Breakdown of Cellulosic Materials," 1978, J. Appl. Chem. Biotechnol. 28:296-308.

Grohmann, K, et al., "Optimization of Dilute Acid Pretreatment of Biomass," Proceedings of the Seventh Symposium on Biotechnology for Fuels and Chemicals, May 14-17, 1986, 24 pages.

Nguyen, Q.A., et al., "An Integrated Model for the Technical and Economic Evaluation of an Enzymatic Biomass Conversion Process," 1991, Bioresource Technology, 35:275-282.

Teleman, et al., "Progress-Curve Analysis Shows that Glucose Inhibits the Cellotriose Hydrosysis Catalysed by Cellobiohydrolase II from Trichoderma Reesi," 1995, European J Biochem, 231:250-258.

Thomas, S., et al., "Biofuels Program C-Milestone Completion Report," FY02, DOE Biofuels Program, Report #373, 2002, 51 pages.

Office action issued in Canadian Application No. 2,638,152, dated Feb. 8, 2011, 4 pages.

International Search Report and the Written Opinion issued in connection with PCT Application No. PCT/CA2009/001032, mailed on Oct. 27, 2009, 11 pages.

Activator 90, Product Brochure, 2009, Loveland Products Inc., No. 6566_May 2009, 1 page.

Amistco Tower Trays, Product Brochure, Amistco Separation Products, Inc., 8 pages.

The Artisan Dualflo Tray, Product Brochure, Artisan Industries, Inc., Bulletin 9801, Edit Date Apr. 17, 2003, 2 pages.

Fuel Ethanol Application Sheet, "CELLIC Ctec and Htec2—Enzymes for Hydrolysis of Lignocellulosic Materials," Novozymes A/S, Luna No. 2010-01668-01, 9 pages.

Flexitray Valve Trays, Product Brochure, Koch-Glitsch, Bulletin FTCVT-01, Revised Mar. 2010, 12 pages.

GEA Wiegand, GmbH, Process Engineering Division, "Bioethanol Technology", Ettlingen, Germany, Company Brochure, 16 pages, 2010.

GEA Wiegand, GmbH, Process Engineering Division, "Distillation Technology", Ettlingen, Germany, Company Brochure, 16 pages.

PROPAX Yeast Propagation Technology, Product Brochure, Meura S.A., Edited 2009, 2 pages.

SILWET L-77 Surfactant, Specimen Label, Helena Chemical Company, Copyright 2006, 2 pages.

SUPERFRAC High Performance Trays, Product Brochure, Koch-Glitsch, Bulletin KGSF-1, Revised Mar. 2010, 16 pages.

"Biofuels Pilot Plant Under Way," Newsbriefs, Chemical Week, Oct. 13/20, 2008, p. 4.

"Lessons Learned from Existing Biomass Power Plants," Feb. 2000, NREL/SR-570-26946, G. Wiltsee, Appel Consultants, Inc., Valencia, CA, 149 pages.

"Types of Lignin and Their Properties," 2001, Information Service from the Lignin Institute, 9/1:4 pages, www.lignin.org/01augdialogue.html.

"Enzyme Sugar-Ethanol Platform Project," NREL, U.S. Dept. of Energy by Midwest Research Institute, Battelle, Bechtel, 47 pages, 2002.

"Easy Steps for Optimal Yeast Rehydration," Laboratory Protocol, Scott Laboratories, Petaluma CA, 1 page, 2010.

Liu, H., et al., "Lignin-Metal Complexation to Eliminate Nonproductive Enzyme Adsorption by Lignin in Unwashed Lignocellulosic Substrates," 2010, 32nd Symposium on Biotechnology for Fuels and Chemicals, 28 pages.

Thomas, S.R., "Corn Stover Feedstock Variability," 2005, Feedstock Area Stage Gate Review Meeting, 34 pages.

Weiss, N.D., et al., "Catalyst Impregnation for High Solids Biomass Pretreatment," 2008, AIChE Annual Meeting, 24 pages.

Zimbardi, F., et al., "Acid Impregnation and Steam Explosion of Corn Stover in Batch Processes," 2007, Ind Crops and Products, 26:195-206.

"Process Design and Cost Estimate of Critical Equipment in the Biomass to Ethanol Process, Report 99-10600/17 Continuous Acid Hydrolysis Reactor," Jan. 22, 2011 Rev WEB, Subcontract ACO-9-29067-01, National Renewable Energy Laboratory, Golden, CO, Harris Group Inc., Seattle, WA, 14 pages.

Abstract of Chinese Patent Application CN 101310879 A, 2008, Institute of Process Engineering, Chinese Academy of Sciences.

* cited by examiner

METHOD FOR PRODUCING ETHANOL AND CO-PRODUCTS FROM CELLULOSIC BIOMASS

REFERENCE TO RELATED APPLICATIONS

This application is a continuation of pending U.S. patent application Ser. No. 13/056,074, filed Jan. 26, 2011, which is a national stage application under 35 U.S.C. 371 of International Patent Application Serial No. PCT/US2010/046561, filed Aug. 24, 2010, which claims the benefit of U.S. Provisional Application Ser. No. 61/236,345, filed Aug. 24, 2009. The entire content of each of the above applications is hereby incorporated herein by reference.

GOVERNMENT LICENSE RIGHTS

This invention was made with Government support under DOE Cooperative Agreement Nos. DE-FC36-03G013142 and DE-FC36-07G017028. The Government has certain rights in this invention.

FIELD OF THE INVENTION

The present invention generally relates to processes for production of ethanol from cellulosic biomass. The present invention also relates to production of various co-products of preparation of ethanol from cellulosic biomass. The present invention further relates to improvements in one or more aspects of preparation of ethanol from cellulosic biomass including, for example, improved methods for cleaning biomass feedstocks, improved acid impregnation, and improved steam treatment, or "steam explosion."

BACKGROUND OF THE INVENTION

Lignocellulosic biomass is a complex structure comprising cellulose, hemicellulose, and lignin in which cellulose and hemicellulose are bound to the lignin. Cellulose is a polymer of D-glucose with β[1-4] linkages between each of the about 500 to 10,000 glucose units. Hemicellulose is a polymer of sugars, primarily D-xylose with other pentoses and some hexoses with β[1-4] linkages derived from herbaceous materials and various hardwood species. Lignin is a complex random polyphenolic polymer.

There are a variety of widely available sources of lignocellulosic biomass including, for example, corn stover, agricultural residues (e.g., straw, corn cobs, etc.), woody materials, energy crops (e.g., sorghum, poplar, etc.), and bagasse (e.g., sugarcane). Thus, lignocellulosic biomass is a relatively inexpensive and readily available substrate for the preparation of sugars, which may be fermented to produce alcohols such as ethanol. Ethanol has a number of uses, including in fuel. For example, ethanol may be used as an additive to gasoline to boost octane, reduce pollution, and/or to partially replace gasoline and reduce crude oil requirements.

Generally, preparation of ethanol from lignocellulosic biomass involves (1) liberating cellulose and hemicellulose from lignin and/or increasing the accessibility of cellulose and hemicellulose to enzymatic hydrolysis, (2) depolymerizing carbohydrate sugars of hemicellulose and cellulose to free sugars, and (3) fermenting the sugars to ethanol.

Processes for preparation of ethanol from lignocellulosic biomass are known, but there remains an unfulfilled need for an ethanol production process that may be practiced economically on a commercial scale. For example, the need exists for ethanol production processes that provide improved ethanol yields over conventional processes and/or provide useful, improved co-products of ethanol production.

SUMMARY OF THE INVENTION

Briefly, therefore, the present invention is directed to improved processes for production of ethanol that provide one or more advantageous results including, for example, improved ethanol yield and/or improved co-products of ethanol production.

The present invention is also directed to methods for cleaning a biomass feedstock. In one embodiment, the method comprises removing from the biomass feedstock a fine particulate fraction, wherein the fine particulate fraction has a particle size distribution such that at least about 95 wt % of the particles pass through a screen having openings of a size of about U.S. Sieve No. 20 (840 µm), thereby forming a cleaned biomass feedstock having an ash content of no more than about 75% of the ash content of the biomass feedstock (dry weight basis).

In another embodiment, the method comprises removing from the biomass feedstock a fine particulate fraction, wherein the fine particulate fraction has a particle size distribution such that at least about 95 wt % of the particles pass through a screen having openings of a size of about U.S. Sieve No. 20 (840 µm), thereby forming a cleaned biomass feedstock having an ash content of less than about 8 wt % (dry weight basis).

In another embodiment, the method comprises removing from the biomass feedstock a fine particulate fraction, thereby forming a cleaned biomass feedstock, wherein the fine particulate fraction has a particle size distribution such that at least about 95 wt % of the particles pass through a screen having openings of a size of about U.S. Sieve No. 20 (840 nm), the ash content of the cleaned biomass feedstock comprises an acid soluble fraction and an acid insoluble fraction, and the acid soluble ash fraction constitutes at least about 30 wt % of the ash content of the cleaned biomass feedstock.

In a further embodiment, the method comprises removing from the biomass feedstock a fine particulate fraction comprising ash, thereby forming a cleaned biomass feedstock, wherein the ratio of ash content of the fine particulate fraction to the ash content of the biomass feedstock is at least about 3:1.

In a still further embodiment, the method comprises removing from the biomass feedstock a fine particulate fraction, thereby forming a cleaned biomass feedstock, wherein the ratio of the ash content of the fine particulate fraction to the ash content of the cleaned biomass feedstock is at least about 5:1.

The present invention is also directed to methods for cleaning a cellulosic biomass feedstock comprising corn stover having an ash content of at least 3 wt %. In one embodiment, the method comprises removing from the biomass feedstock a fine particulate fraction, wherein the fine particulate fraction has a particle size distribution such that at least about 95 wt % of the particles pass through a screen having openings of a size of about U.S. Sieve No. 20 (840 µm), thereby forming a cleaned biomass feedstock having an ash content of no more than about 75% of the ash content of the biomass feedstock (dry weight basis). In another embodiment, the method comprises removing from the biomass feedstock a fine particulate fraction comprising ash, thereby forming a cleaned biomass feedstock, wherein the ratio of ash content of the fine particulate fraction to the ash content of the biomass feedstock is at least about 3:1.

The present invention is further directed to methods for cleaning a cellulosic biomass feedstock wheat straw having an ash content of at least 3 wt %. In one embodiment, the method comprises removing from the biomass feedstock a fine particulate fraction, wherein the fine particulate fraction has a particle size distribution such that at least about 95 wt % of the particles pass through a screen having openings of a size of about U.S. Sieve No. 20 (840 μm), thereby forming a cleaned biomass feedstock having an ash content of no more than about 75% of the ash content of the biomass feedstock (dry weight basis). In another embodiment, the method comprises removing from the biomass feedstock a fine particulate fraction comprising ash, thereby forming a cleaned biomass feedstock, wherein the ratio of ash content of the fine particulate fraction to the ash content of the biomass feedstock is at least about 3:1.

The present invention is further directed to methods for pretreatment of cellulosic biomass feedstock comprising cellulose, hemicellulose, and lignin.

The present invention is also directed to methods for pretreatment of particulate cellulosic biomass feedstock that comprise removing a fine particulate fraction from the biomass feedstock. In one embodiment, a cleaned particulate biomass feedstock having an acid neutralization capacity as determined in accordance with Protocol A of less than 0.01 is formed. In another embodiment, a cleaned particulate biomass feedstock having an acid neutralization capacity as determined in accordance with Protocol A that is no more than about 90% of the acid neutralization capacity of the biomass feedstock is formed.

In one embodiment, the method comprises removing from the particulate biomass feedstock a fine particulate fraction, thereby forming a cleaned particulate biomass feedstock; contacting the cleaned particulate biomass feedstock with an acidic liquid medium in an acid impregnation zone to form an acid-impregnated cellulosic biomass feedstock, the weight ratio of acid to solids fraction of the cleaned particulate biomass feedstock introduced into the acid impregnation zone is less than about 0.05:1; and contacting the acid-impregnated biomass feedstock with water at elevated temperature and pressure in a pretreatment zone, thereby forming a pretreated biomass feedstock comprising a solids fraction and a liquid fraction comprising xylose, wherein the xylose content, as determined in accordance with Protocol B, of the pretreated biomass feedstock liquid fraction represents a yield of at least about 70% (based on hemicellulose content of the particulate biomass feedstock).

In another embodiment, the method comprises removing from the particulate biomass feedstock a fine particulate fraction, thereby forming a cleaned particulate biomass feedstock; contacting the cleaned particulate biomass feedstock with an acidic liquid medium in an acid impregnation zone to form an acid-impregnated cellulosic biomass feedstock, the weight ratio of acid to solids fraction of the cleaned particulate biomass feedstock introduced into the acid impregnation zone is less than about 0.05:1; and contacting the acid-impregnated biomass feedstock with water at elevated temperature and pressure in a pretreatment zone, thereby forming a pretreated biomass feedstock comprising a solids fraction comprising cellulose; the cellulose digestibility of the pretreated biomass feedstock as determined in accordance with Protocol C is at least about 60%.

In one embodiment, the method comprises contacting the cellulosic biomass feedstock with an acidic liquid medium to form an acid-impregnated biomass feedstock; contacting the acid-impregnated cellulosic biomass feedstock with $H_2O$ at elevated temperature and pressure within a contact zone under conditions effective for solubilizing hemicellulose and producing a steam treated feedstock; subjecting the steam treated feedstock within a depressurization zone to conditions effective for solubilizing hemicellulose and producing a volatilized fraction of the steam treated feedstock; and releasing at least a portion of the volatilized fraction from the depressurization zone for control of temperature and pressure within the depressurization zone, wherein control of the temperature and pressure within the depressurization zone consists essentially of releasing at least a portion of the volatilized fraction therefrom.

The present invention is also directed to methods for pretreatment of virgin cellulosic biomass feedstock comprising cellulose, hemicellulose, and lignin. In one embodiment, the method comprises contacting the cellulosic biomass feedstock and an acidic aqueous liquid medium to form an acid-impregnated cellulosic biomass feedstock containing less than 50 wt % aqueous liquid on a water basis.

The present invention is further directed to methods for pretreatment of particulate cellulosic biomass feedstock comprising cellulose, hemicellulose, and lignin. In one embodiment the method comprises contacting the cellulosic biomass feedstock and an acidic aqueous liquid medium to form an acid-impregnated cellulosic biomass feedstock, wherein at least about 50 wt % of the feedstock particles have a size in their largest dimension of from about 0.6 cm (0.25 inches) to about 4 cm (1.5 inches).

In one embodiment, the method comprises spraying an acidic liquid medium onto the cellulosic biomass feedstock to form an acid-impregnated cellulosic biomass feedstock; and contacting the acid-impregnated cellulosic biomass feedstock with $H_2O$ for between about 1 and about 120 minutes at elevated temperature within a contact zone containing a vapor phase wherein the partial pressure of water vapor is at least about 55 psig.

In another embodiment, the method comprises spraying an acidic liquid medium onto the cellulosic biomass feedstock to form an acid-impregnated cellulosic biomass feedstock, and agitating the feedstock to distribute the medium within the feedstock and bring particles of the feedstock into mutually abrading contact.

In another embodiment, the method comprises spraying an acidic liquid medium onto the cellulosic biomass feedstock to form an acid-impregnated cellulosic biomass feedstock in a contact zone, wherein the contact zone comprises parallel counter-rotating shafts having flights mounted thereon for agitation of the biomass.

In a still further embodiment, the method comprises, contacting the cellulosic biomass feedstock with an aqueous liquid medium comprising an acid and a surfactant (wetting agent) to form an acid-impregnated biomass feedstock.

In another embodiment, the method comprises contacting the cellulosic biomass feedstock and an acidic liquid medium to form an acid-impregnated cellulosic biomass feedstock; contacting the acid-impregnated cellulosic biomass feedstock with $H_2O$ at elevated temperature within a contact zone containing a vapor phase wherein the partial pressure of water vapor is at least about 55 psig to solubilize hemicellulose and produce a volatilized fraction of the acid-impregnated feedstock; and releasing at least a portion of the volatilized fraction from the contact zone at a rate effective to control the pressure in the contact zone.

In another embodiment, the method comprises introducing the feedstock into a steam contact zone, the contact zone having an inlet for steam and an outlet for pretreated feedstock; introducing steam into the contact zone at the inlet to contact steam and the feedstock and form a steam treated feedstock; and removing pretreated feedstock from the contact zone through the outlet and into a receiving zone, wherein the pressure in the receiving zone does not differ from the pressure in the contact zone by more than about 200 psig.

In another embodiment, the method comprises introducing the feedstock into a steam contact zone; introducing steam into the contact zone to contact the feedstock and form a steam-treated feedstock; and passing the steam-treated feedstock from the steam contact zone through a flow restriction and into a receiving zone, the pressure drop across the flow restriction being less than about 150 psi.

In another embodiment, the method comprises contacting the cellulosic biomass feedstock with $H_2O$ within a contact zone containing a vapor phase wherein the partial pressure of water vapor is at least about 55 psig, the $H_2O$ being distributed within the zone so that the biomass is brought to a target temperature, and the average temperature of any region of the biomass that contains more than 15% by weight of the biomass does not differ by more than 5° C. from the target temperature.

The present invention is further directed to methods for pretreatment of cellulosic biomass feedstock comprising cellulose, hemicellulose, lignin, and one or more impurities. In one embodiment, the method comprises contacting the cellulosic biomass feedstock with an acidic aqueous liquid medium to form an acid-impregnated cellulosic biomass feedstock; and removing an aqueous liquid fraction from the acid-impregnated cellulosic biomass feedstock to form an acid-impregnated feedstock having a reduced content of the one or more impurities.

The present invention is further directed to methods for washing a virgin solid phase biomass feedstock comprising cellulose, hemicellulose, and lignin. In one embodiment, the method comprises contacting the cellulosic biomass with an aqueous washing liquid and thereafter separating the resulting wash liquor from the solid phase biomass, the biomass being contacted with the washing liquid under conditions that do not degrade the fibers by more than 20% as measured by the average length of fibers in the biomass after the contacting as compared to the average length of fibers in the biomass before the contacting.

The present invention is further directed to methods for recovering $C_5$ sugars from cellulosic biomass feedstock comprising cellulose, hemicellulose and lignin. In one embodiment, the method comprises pretreating the biomass feedstock in the presence of an aqueous liquid medium; contacting the pretreated feedstock with a hemicellulase to produce a hydrolyzate slurry comprising an aqueous phase containing $C_5$ sugar(s) and a solid phase comprising cellulose and lignin; and separating an aqueous liquid hydrolyzate fraction comprising $C_5$ sugar(s) from the hydrolyzate slurry.

The present invention is further directed to methods for producing fermentable sugars from a cellulosic biomass feedstock comprising cellulose, hemicellulose, and lignin. In one embodiment, the method comprises contacting the cellulosic biomass feedstock with an acidic liquid medium to form an acid-impregnated cellulosic biomass feedstock; forming a pretreated cellulosic biomass feedstock, the forming comprising contacting the acid-impregnated cellulosic biomass feedstock with $H_2O$ at elevated temperature and pressure; contacting the pretreated cellulosic biomass feedstock with a hemicellulase enzyme to hydrolyze hemicellulose and produce hemicellulose-derived fermentable sugars in a hemicellulose hydrolyzate comprising a liquid phase comprising solubilized hemicellulose-derived fermentable sugars and a solid phase comprising cellulose and lignin; and removing an aqueous liquid phase comprising hemicellulose-derived fermentable sugars from the pretreated hydrolyzate.

The present invention is further directed to methods for conversion of cellulose to glucose in an aqueous hydrolysis medium. In one embodiment, the method comprises contacting glucose, cellulose, a nitrogen source, and a microbe that is effective to express a cellulase enzyme in an aqueous biosynthesis medium within a microbe proliferation zone thereby producing cellulase enzyme within the proliferation zone; transferring cellulase from the proliferation zone to a cellulose hydrolysis zone wherein cellulase is contacted with cellulose in a cellulase hydrolysis medium; and enzymatically hydrolyzing cellulose in the cellulase hydrolysis medium within the enzymatic hydrolysis zone, thereby generating $C_6$ sugars.

The present invention is further directed to methods for producing a cellulase enzyme from virgin cellulosic biomass feedstock comprising cellulose, hemicellulose, and lignin. In one embodiment, the method comprises contacting the cellulosic biomass feedstock with an acidic liquid medium to form an acid-impregnated cellulosic biomass feedstock; forming a pretreated cellulosic biomass feedstock, the forming comprising contacting the acid-impregnated cellulosic biomass feedstock with $H_2O$ at elevated temperature and pressure; hydrolyzing hemicellulose of the pretreated cellulosic biomass feedstock to produce hemicellulose-derived fermentable sugars in a hemicellulose hydrolyzate comprising a liquid phase comprising solubilized hemicellulose-derived fermentable sugars and a solid phase comprising cellulose and lignin; separating an aqueous liquid hydrolyzate fraction comprising hemicellulose-derived fermentable sugars from the pretreated hydrolyzate; and contacting in a proliferation zone a portion of the solid phase comprising cellulose, a nitrogen source, and a microbe that is effective to express a cellulase enzyme, thereby producing cellulase enzyme within the proliferation zone.

The present invention is further directed to methods for producing and/or recovering ethanol from a cellulosic biomass feedstock comprising cellulose, hemicellulose, and lignin.

In one embodiment, the method comprises pretreating the biomass to increase the bioavailability of the hemicellulose and cellulose contained therein; contacting the pretreated biomass with a hemicellulase to cause hemicellulose to be hydrolyzed to yield soluble $C_5$ sugar(s) and produce a hemicellulase hydrolyzate slurry comprising an aqueous phase containing $C_5$ sugar(s) and a solid phase comprising cellulose and lignin; separating an aqueous phase $C_5$ fraction comprising $C_5$ sugar(s) from the hemicellulase hydrolyzate slurry, yielding a thickened residual fraction comprising a cake or concentrated slurry comprising the solid phase cellulose and lignin; contacting $C_5$ sugars obtained in the aqueous phase $C_5$ fraction with a yeast, thereby converting $C_5$ sugar(s) to ethanol and producing a $C_5$ fermentate containing ethanol; contacting cellulose of the thickened fraction with a cellulase, thereby converting cellulose to $C_6$ sugar(s) and producing a $C_6$ hydrolyzate; and contacting $C_6$ sugars produced in the $C_6$ hydrolyzate fraction with a yeast, thereby converting $C_6$ sugar(s) to ethanol and producing a $C_6$ fermentate containing ethanol.

In another embodiment, the method comprises contacting the cellulosic biomass feedstock with an acidic aqueous liquid medium to form an acid-impregnated cellulosic biomass feedstock; forming a pretreated feedstock comprising solubilized hemicellulose and a solid phase comprising cellulose and lignin, the forming comprising contacting the acid-impregnated cellulosic biomass feedstock with $H_2O$ at elevated temperature and pressure; removing an aqueous liquid phase comprising solubilized hemicellulose from the pretreated feedstock, forming a thickened pretreated hydrolyzate comprising the solid phase cellulose and lignin; introducing solid phase cellulose and lignin into a cellulose hydrolysis zone wherein cellulose is contacted with a cellulase and cellulose is enzymatically hydrolyzed to produce a cellulose hydrolyzate slurry comprising an aqueous phase comprising cellulose-derived fermentable sugars and a solid phase comprising lignin; contacting the cellulose hydrolyzate slurry with a yeast to convert cellulose-derived fermentable sugars to ethanol and form a fermentation slurry comprising an aqueous phase comprising ethanol and a solid phase comprising lignin; distilling the fermentation slurry to produce an ethanol rich product stream and a bottoms product comprising a solid phase comprising lignin; and recovering a lignin-rich product from the bottoms product.

In another embodiment, the method comprises contacting the cellulosic biomass feedstock with an acidic aqueous liquid medium to form an acid-impregnated cellulosic biomass feedstock; forming a pretreated feedstock comprising solubilized hemicellulose and a solid phase comprising cellulose and lignin, the forming comprising contacting the acid-impregnated cellulosic biomass feedstock with $H_2O$ at elevated temperature and pressure; removing an aqueous liquid phase comprising solubilized hemicellulose from the pretreated feedstock, forming a thickened pretreated hydrolyzate comprising the solid phase cellulose and lignin; and introducing the thickened pretreated hydrolyzate into a saccharification and fermentation zone wherein solid phase cellulose and a cellulase are contacted to form cellulose-derived fermentable sugars and at least a portion of the cellulose-derived fermentable sugars are contacted with a yeast to convert cellulose-derived fermentable sugars to ethanol, wherein the solid phase cellulose of the thickened pretreated hydrolyzate is in the form of fibers such that at least about 10% (by weight) of the fibers have a size in their largest dimension less than about 1 mm.

In another embodiment, the method comprises contacting the cellulosic biomass feedstock with an acidic aqueous liquid medium to form an acid-impregnated cellulosic biomass feedstock; forming a pretreated feedstock comprising solubilized hemicellulose and a solid phase comprising cellulose and lignin, the forming comprising contacting the acid-impregnated cellulosic biomass feedstock with $H_2O$ at elevated temperature and pressure; removing lignin from the pretreated feedstock; introducing solid phase cellulose into a cellulose hydrolysis zone wherein cellulose is contacted with a cellulase and cellulose is enzymatically hydrolyzed to produce a cellulose hydrolyzate slurry comprising an aqueous phase comprising cellulose-derived fermentable sugars; contacting the cellulose hydrolyzate slurry with a yeast to convert cellulose-derived fermentable sugars to ethanol and form a fermentation slurry comprising an aqueous phase comprising ethanol; and distilling the fermentation slurry to produce an ethanol rich product stream.

In a further embodiment, the method comprises contacting the cellulosic biomass feedstock with an acidic aqueous liquid medium to form an acid-impregnated cellulosic biomass feedstock comprising cellulose, hemicellulose, and lignin; introducing a portion of the acid-impregnated feedstock into a microbe proliferation zone, and contacting cellulose, glucose, a nitrogen source, and a microbe that is effective to express a cellulase enzyme in an aqueous biosynthesis medium within the microbe proliferation zone, thereby producing cellulase enzyme within the proliferation zone; introducing a portion of the acid-impregnated feedstock into a cellulose hydrolysis zone wherein cellulose is contacted with a cellulase and cellulose is enzymatically hydrolyzed to produce a cellulose hydrolyzate slurry comprising an aqueous phase comprising cellulose-derived fermentable sugars; introducing at least a portion of the cellulase produced within the proliferation zone into the cellulose hydrolysis zone; contacting the cellulose hydrolyzate slurry with a yeast to convert cellulose-derived fermentable sugars to ethanol and form a fermentation slurry comprising an aqueous phase comprising ethanol; and distilling the fermentation slurry to produce an ethanol rich product stream.

In a further embodiment, the method comprises pretreating the biomass to increase the bioavailability of the hemicellulose and cellulose contained therein; contacting the pretreated biomass with a hemicellulase to cause hemicellulose to be hydrolyzed to soluble $C_5$ sugar(s) and produce a hemicellulase hydrolyzate slurry comprising an aqueous phase containing $C_5$ sugar(s) and a solid phase comprising cellulose and lignin; separating an aqueous phase $C_5$ hydrolyzate fraction comprising $C_5$ sugar(s) from the hemicellulase hydrolyzate slurry, yielding a thickened residual fraction comprising a cake or concentrated slurry comprising the solid phase cellulose and lignin; contacting $C_5$ sugars obtained in the aqueous phase $C_5$ fraction with a yeast, thereby converting $C_5$ sugar(s) to ethanol and producing a $C_5$ fermentate containing ethanol; removing lignin from the thickened residual fraction; and contacting cellulose of the thickened fraction having lignin removed therefrom with a cellulase, thereby converting cellulose to $C_6$ sugar(s) and producing a $C_6$ hydrolyzate.

In another embodiment, the method comprises contacting the cellulosic biomass feedstock with an acidic aqueous liquid medium to form an acid-impregnated cellulosic biomass feedstock comprising cellulose, hemicellulose, and lignin; introducing a portion of the acid-impregnated feedstock into a microbe proliferation zone, and contacting cellulose, glucose, a nitrogen source, and a microbe that is effective to express a cellulase enzyme in an aqueous biosynthesis medium within the microbe proliferation zone, thereby producing cellulase enzyme within the proliferation zone; removing lignin from the acid-impregnated cellulosic biomass feedstock; introducing solid phase cellulose of the acid-impregnated cellulosic biomass feedstock having lignin removed therefrom into a cellulose hydrolysis zone wherein cellulose is contacted with a cellulase and cellulose is enzymatically hydrolyzed to produce a cellulose hydrolyzate slurry comprising an aqueous phase comprising cellulose-derived fermentable sugars; and introducing at least a portion of the cellulase produced within the proliferation zone into the cellulose hydrolysis zone.

In another embodiment, the method comprises pretreating the biomass to increase the bioavailability of the hemicellulose and cellulose contained therein; contacting the pretreated biomass with a hemicellulase to cause hemicellulose to be hydrolyzed to soluble $C_5$ sugar(s) and produce a hemicellulase hydrolyzate slurry comprising an aqueous phase containing $C_5$ sugar(s) and a solid phase comprising cellulose and lignin; separating an aqueous phase $C_5$ hydrolyzate fraction comprising $C_5$ sugar(s) from the hemicellulase hydrolyzate slurry, yielding a thickened residual fraction comprising a cake or concentrated slurry comprising the solid phase cellulose and lignin; contacting $C_5$ sugars obtained in the aqueous phase $C_5$ fraction with a yeast, thereby converting $C_5$ sugar(s) to ethanol and producing a $C_5$ fermentate containing ethanol; introducing a portion of the thickened residual fraction into a microbe proliferation zone, and contacting cellulose, glucose, a nitrogen source, and a microbe that is effective to express a cellulase enzyme in an aqueous biosynthesis medium within the microbe proliferation zone, thereby producing cellulase enzyme within the proliferation zone; and contacting cellulose of the thickened fraction with a cellulase, thereby converting cellulose to $C_6$ sugar(s) and producing a $C_6$ hydrolyzate, wherein at least a portion of the cellulase is cellulase enzyme produced within the proliferation zone.

In a further embodiment, the method comprises pretreating the biomass to increase the bioavailability of the hemicellulose and cellulose contained therein; contacting the pretreated biomass with a hemicellulase to cause hemicellulose to be hydrolyzed to soluble $C_5$ sugar(s) and produce a hemicellulase hydrolyzate slurry comprising an aqueous phase containing $C_5$ sugar(s) and a solid phase comprising cellulose and lignin; separating an aqueous phase $C_5$ fraction comprising $C_5$ sugar(s) from the hemicellulase hydrolyzate slurry, yielding a thickened residual fraction comprising a cake or concentrated slurry comprising the solid phase cellulose and lignin; contacting $C_5$ sugars obtained in the aqueous phase $C_5$ fraction with a yeast, thereby converting $C_5$ sugar(s) to ethanol and producing a $C_5$ fermentate containing ethanol; contacting cellulose of the thickened fraction with a cellulase, thereby converting cellulose to $C_6$ sugar(s) and producing a $C_6$ hydrolyzate slurry comprising $C_6$ sugars and a solid phase comprising lignin; contacting the $C_6$ hydrolyzate slurry with a yeast to convert $C_6$ sugars to ethanol and form a fermentation slurry comprising an aqueous phase comprising ethanol and a solid phase comprising lignin; distilling the fermentation slurry to produce an ethanol rich product stream and a bottoms product comprising a solid phase comprising lignin; and recovering a lignin-rich product from the bottoms product.

In a further embodiment, the method comprises removing from the biomass feedstock a fine particulate fraction, thereby forming a cleaned particulate biomass feedstock; contacting the cleaned particulate biomass feedstock with an acidic aqueous liquid medium to form an acid-impregnated cellulosic biomass feedstock; forming a pretreated feedstock comprising solubilized hemicellulose and a solid phase comprising cellulose and lignin, said forming comprising contacting the acid-impregnated cellulosic biomass feedstock with $H_2O$ at elevated temperature and pressure; removing lignin from the pretreated feedstock; introducing solid phase cellulose into a cellulose hydrolysis zone wherein cellulose is contacted with a cellulase and cellulose is enzymatically hydrolyzed to produce a cellulose hydrolyzate slurry comprising an aqueous phase comprising cellulose-derived fermentable sugars; contacting the cellulose hydrolyzate slurry with a yeast to convert cellulose-derived fermentable sugars to ethanol and form a fermentation slurry comprising an aqueous phase comprising ethanol; and distilling the fermentation slurry to produce an ethanol rich product stream.

In another embodiment, the method comprises removing from the biomass feedstock a fine particulate fraction, thereby forming a cleaned particulate biomass feedstock; contacting the cleaned particulate biomass feedstock with an acidic aqueous liquid medium to form an acid-impregnated cellulosic biomass feedstock comprising cellulose; introducing a portion of the acid-impregnated feedstock into a microbe proliferation zone, and contacting cellulose, glucose, a nitrogen source, and a microbe that is effective to express a cellulase enzyme in an aqueous biosynthesis medium within the microbe proliferation zone, thereby producing cellulase enzyme within said proliferation zone; introducing a portion of the acid-impregnated feedstock into a cellulose hydrolysis zone wherein cellulose is contacted with a cellulase and cellulose is enzymatically hydrolyzed to produce a cellulose hydrolyzate slurry comprising an aqueous phase comprising cellulose-derived fermentable sugars; introducing at least a portion of the cellulase produced within said proliferation zone into said cellulose hydrolysis zone; contacting the cellulose hydrolyzate slurry with a yeast to convert cellulose-derived fermentable sugars to ethanol and form a fermentation slurry comprising an aqueous phase comprising ethanol; and distilling the fermentation slurry to produce an ethanol rich product stream.

In a still further embodiment, the method comprises removing from the biomass feedstock a fine particulate fraction, thereby forming a cleaned particulate biomass feedstock; pretreating the cleaned particulate biomass feedstock to increase the bioavailability of the hemicellulose and cellulose contained therein; contacting the pretreated biomass with a hemicellulase to cause hemicellulose to be hydrolyzed to soluble $C_5$ sugar(s) and produce a hemicellulase hydrolyzate slurry comprising an aqueous phase containing $C_5$ sugar(s) and a solid phase comprising cellulose and lignin; separating an aqueous phase $C_5$ hydrolyzate fraction comprising $C_5$ sugar(s) from the hemicellulase hydrolyzate slurry, yielding a thickened residual fraction comprising a cake or concentrated slurry comprising said solid phase cellulose and lignin; contacting $C_5$ sugars obtained in said aqueous phase $C_5$ fraction with a yeast, thereby converting $C_5$ sugar(s) to ethanol and producing a $C_5$ fermentate containing ethanol; removing lignin from the thickened residual fraction; and contacting cellulose of said thickened fraction having lignin removed therefrom with a cellulase, thereby converting cellulose to $C_6$ sugar(s) and producing a $C_6$ hydrolyzate.

In another embodiment, the method comprises contacting the cellulosic biomass feedstock with an acidic aqueous liquid medium to form an acid-impregnated cellulosic biomass feedstock comprising cellulose, hemicellulose, and lignin; introducing a portion of the acid-impregnated feedstock into a microbe proliferation zone, and contacting cellulose, glucose, a nitrogen source, and a microbe that is effective to express a cellulase enzyme in an aqueous biosynthesis medium within the microbe proliferation zone, thereby producing cellulase enzyme within the proliferation zone; introducing solid phase cellulose into a cellulose hydrolysis zone wherein cellulose is contacted with a cellulase and cellulose is enzymatically hydrolyzed to produce a cellulose hydrolyzate slurry comprising an aqueous phase comprising cellulose-derived fermentable sugars; introducing at least a portion of the cellulase produced within the proliferation zone into the cellulose hydrolysis zone; contacting the cellulose hydrolyzate slurry with a yeast to convert cellulose-derived fermentable sugars to ethanol and form a fermentation slurry comprising an aqueous phase comprising ethanol and a solid phase comprising lignin; distilling the fermentation slurry to produce an ethanol rich product stream and a bottoms product comprising a solid phase comprising lignin; and recovering a lignin-rich product from the bottoms product.

The present invention is further directed to a distiller's biomass product prepared from a cellulosic biomass feedstock comprising cellulose, hemicellulose, lignin, and protein. In one embodiment, the weight ratio of the protein content of the biomass product to the protein content of the biomass feedstock is at least 1:1.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE PREFERRED EMBODIMENTS

Figure 1:
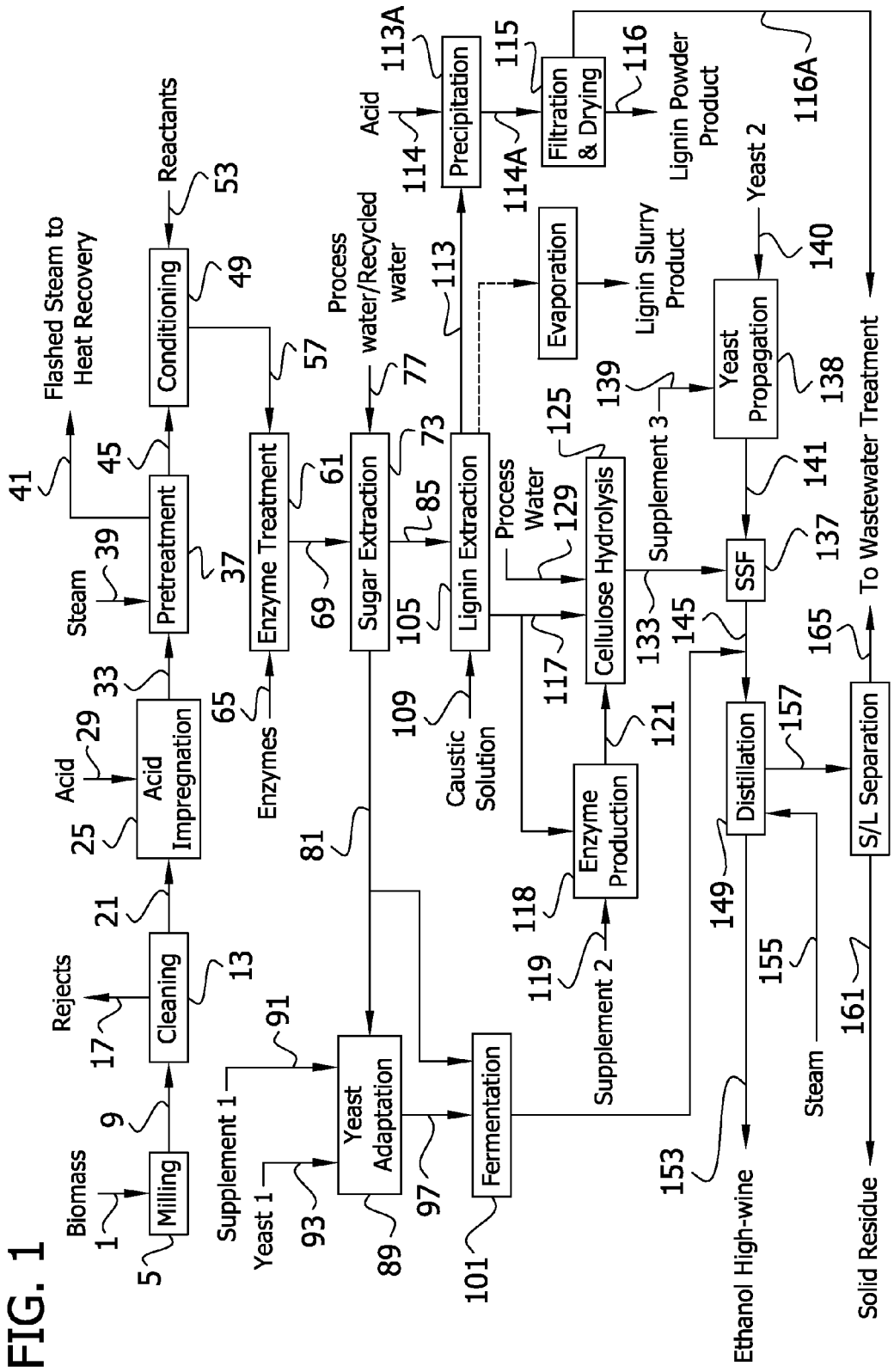
FIG. 1 depicts a process flow of one embodiment of an ethanol production process of the present invention.

Described herein are improved processes for production of ethanol from lignocellulosic biomass including, for example, processes which provide improved ethanol yield. Also described herein are processes which provide various advantageous co-products. As detailed herein, improvements in ethanol yield and/or advantageous co-products may be provided by one or more aspects of various protocols for treatment of lignocellulosic biomass that may be utilized in an ethanol production process.

For example, various protocols for pretreatment of lignocellulosic biomass have been observed to improve process efficiencies. Generally, these pretreatment protocols comprise contacting a lignocellulosic biomass feedstock with an acidic liquid medium under certain conditions (e.g., certain mass ratios of acid to biomass feed). As used herein, the term "pretreatment" refers to processing of biomass feedstock prior to hydrolysis of the lignocellulosic biomass for the primary purpose of producing fermentable sugars by hydrolysis of hemicellulose and/or cellulose.

Various embodiments of the present invention involve pretreatment protocols that utilize a feedstock and/or provide a pretreated feedstock having relatively high solids content (i.e., low moisture content). Various other protocols provide prescribed manners for contact of the feedstock and the acidic liquid medium (e.g., by soaking or spraying) that promote advantageous dispersion of the acidic liquid medium throughout the biomass feedstock. These and other pretreatment protocols may also utilize methods for removal of one or more volatile components by venting during contact of acid-impregnated biomass feedstock and steam at elevated temperature and pressure. By way of further example, one or more parameters of the pretreatment protocol are controlled and/or selected to provide a pretreated biomass feedstock having minimal temperature variation. Further in accordance with the present invention, pretreated feedstock may be subjected to a conditioning operation to remove one or more components of the pretreated feedstock that may inhibit fermentation of sugars derived from hemicellulose and/or cellulose.

In accordance with various embodiments of the present invention, the biomass feedstock is subjected to a cleaning operation for purposes of providing a cleaned biomass feedstock suitable for effective acid impregnation. In particular, various methods detailed herein are effective for providing a cleaned biomass feedstock having a significant portion of impurities (e.g., components of the ash fraction of the biomass feedstock) removed therefrom. As detailed elsewhere herein, these methods provide biomass feedstocks that provide advantageous consumption of the acid by the feedstock as evidenced by, for example, advantageous fermentable sugar yields during pretreatment. Advantageously, these methods are conducted in the absence of wash water and, thus, are referred to herein as "dry cleaning" methods.

The present invention is further directed to enzymatic hydrolysis of hemicellulose-derived sugars prior to and/or in parallel with hydrolysis of fermentable cellulose-derived sugars, which has also been observed to contribute to improved processes (e.g., improved ethanol yields). For example, various aspects of the present invention are directed to methods for production of ethanol that include recovery of hemicellulose-derived sugars and their conversion to ethanol along with recovery of cellulose-derived sugars and their conversion to ethanol.

By way of further example, various aspects of the present invention are directed to cellulase enzyme generation integrated into a process for preparing ethanol from lignocellulosic biomass. For example, aspects of the present invention are directed to conversion of cellulose to glucose by methods that include producing a cellulase enzyme within a proliferation zone and contacting the cellulase enzyme thus produced with cellulose to generate cellulose-derived sugars (i.e., glucose). In various embodiments, integrated cellulase generation is combined along with recovery of hemicellulose-derived sugars and their conversion to ethanol.

The present invention is also directed to protein-rich distiller's biomass products and lignin-rich co-products. More particularly, processes of the present invention are directed to recovery of lignin-rich co-products from biomass feedstock prior to production of fermentable sugars by hydrolysis of cellulose-derived sugars. Processes of the present invention are likewise directed to recovery of lignin-rich co-products after production of ethanol from cellulose-derived sugars. These processes for recovery of lignin-rich co-products may be combined with recovery of hemicellulose-derived sugars and their conversion to ethanol, either before or after recovery of the lignin-rich co-product. Further in accordance with the present invention, recovery of lignin-rich co-products may be combined along with integrated cellulase generation.

I. Feedstock

Generally, the feedstock (1 in FIG. 1) comprises woody and non-woody cellulosic biomass provided by, for example, plant biomass, agricultural wastes, forestry residues, and sugar processing residues. More particularly, the feedstock may comprise grasses, such as switchgrass, cord grass, rye grass, reed canary grass, miscanthus, or combinations thereof. Additionally or alternatively, the feedstock may include agricultural wastes such as rice straw, rice hulls, barley straw, corn cobs, wheat straw, canola straw, oat straw, oat hulls, corn fiber, stover (e.g., sorghum, soybean stover and/or corn stover), or combinations thereof. Suitable sugar-processing residues include, for example, sugar cane bagasse, sweet sorghum, beet pulp, and combinations thereof. In various embodiments the feedstock comprises a non-woody biomass selected from the group consisting of corn stover, wheat straw, barley straw, sorghum, switchgrass, miscanthus, and combinations thereof. In various preferred embodiments, the feedstock comprises corn stover. In these and other preferred embodiments, the feedstock comprises wheat straw. Still further, in these and various other preferred embodiments, the feedstock comprises switchgrass. The feedstock may also include wood and forestry wastes such as, for example, recycled wood pulp fiber, sawdust, hardwood, softwood, forest thinnings, orchard thinnings, or combinations thereof. Accordingly, in various embodiments, the feedstock comprises a woody biomass.

Much of the following discussion, including the discussion below regarding FIGS. 1 and 2, focuses on corn stover as the feedstock. However, unless specifically noted otherwise, it is to be understood that the following discussion generally applies to all suitable lignocellulosic biomass feedstocks.

Lignocellulosic biomass is a mixture of carbohydrate polymers from plant cell walls (i.e., cellulose and hemicellulose), lignin, and various other components (e.g., ash and sand). For example, corn stover typically has a cellulose content of from about 30 wt % to about 40 wt %, a hemicellulose content of from about 20 wt % to about 30 wt %, and a lignin content of from about 15 wt % to about 25 wt %. Corn stover typically contains a portion of ash (e.g., at least about 3 wt %, from about 3 wt % to about 10 wt %, or from about 4 wt % to about 8 wt %). A major portion of the ash in corn stover is silica. Therefore, for example, the silica content of corn stover is generally at least about 1 wt % or at least 5 wt %, typically from about 1 wt % to about 7 wt % or from about 1 wt % to 5 wt % (e.g., from about 3 wt % to 5 wt %).

Wheat straw typically has a cellulose content of from about 30 wt % to about 45 wt %, a hemicellulose content of from about 20 wt % to about 30 wt %, and a lignin content of from about 15 wt % to about 25 wt %. Wheat straw typically contains a portion of ash (e.g., at least about 3 wt %, from about 3 wt % to about 10 wt %, or from about 4 wt % to about 8 wt %). A portion of the ash in wheat straw is silica. Therefore, for example, the silica content of wheat straw is generally at least about 1 wt % and typically from about 1 wt % to about 7 wt %.

By way of further example, switchgrass typically has a cellulose content of from about 30 wt % to about 38 wt %, a hemicellulose content of from about 22 wt % to about 30 wt %, and a lignin content of from about 16 wt % to about 22 wt %. Switchgrass also typically contains a minor portion of ash (e.g., from about 3 wt % to about 8 wt %, or from about 4 wt % to about 6 wt %).

Woody biomass, for example, typically has a cellulose content of from about 30 wt % to about 55 wt %, a hemicellulose content of from about 20 wt % to about 35 wt %, and a lignin content of from about 15 wt % to about 25 wt %. Woody biomass typically contains a very minor portion of ash (e.g., less than about 5 wt %, less than about 2 wt %, from about 0.1 wt % to about 5 wt %, or from about 0.1 wt % to about 2 wt %). Similarly, the silica content in woody biomass is generally very low, approaching zero in some species. For example, the silica content of woody biomass is generally less than about 0.2 wt % and typically from about 0.01 wt % to about 0.2 wt %.

Various processes for production of ethanol from lignocellulosic biomass utilize sources of cellulose that have been subjected to one or more operations prior to treatment as detailed herein to break down the cellulose-hemicellulose-lignin complex (i.e., complex) and provide fermentable sugars (e.g., acid impregnation followed by steam treatment). For example, sugar cane bagasse is typically processed to provide a slurry comprising biomass feedstock from which a substantial portion, if not substantially all the soluble components have been removed. These treatments may also solubilize hemicellulose, thereby reducing fermentable sugar yield during later processing. In addition, prior treatment of the bagasse typically provides a moisture-impregnated substrate. A moisture-impregnated substrate impedes acid impregnation (detailed elsewhere herein).

Methods of the present invention are suitable for treatment of biomass feedstock prior to any processing that will impact later processing for the purposes of deriving fermentable sugars and/or increasing the bioavailability of cellulose. Thus, biomass feedstock treated by the present methods may be referred to as field-harvested or virgin feedstock. In contrast to feedstock subjected to prior treatment (e.g., sugar cane bagasse) as described above, soluble components remain in the feedstock. As detailed herein, solubilized hemicellulose provides fermentable sugars that contribute to ethanol yields. In this manner, maximum fermentable sugar yields and/or improvements in cellulose bioavailability may be provided by the present methods Inhibitors of break down of the complex and/or enzymatic hydrolysis may be present in the field-harvested or virgin feedstock. Various strategies detailed herein address these issues to substantially minimize, and preferably avoid any impact on complex break down and/or fermentable sugar yields.

Typically, lignocellulosic biomass is provided for processing in its condition as stored and the precise properties of the biomass feedstock are not narrowly critical. Moisture content of the feedstock may vary depending on a variety of factors including, for example, the duration of storage prior to processing. For example, corn stover typically has a moisture content of from about 5 wt % to about 20 wt % or from about 5 wt % to about 15 wt %, preferably less than about 15 wt %, and even more preferably less than 10 wt %. It is to be understood that moisture contents provided herein refer to both free and bound moisture. If the feedstock provided contains a relatively high moisture content (e.g., greater than 20 wt %, or greater than about 25 wt %), the feedstock may be heated prior to use to reduce its moisture content. However, feedstocks having moisture content within or below the above-noted ranges are preferred. Heating of the feedstock prior to processing increases the cost of the process. In addition, the energy requirements of milling operations (detailed elsewhere herein) likewise increase as moisture content of the feedstock increases.

Regardless of the moisture content, if the feedstock is stored at relatively low temperatures it may be desired to heat the feedstock prior to treatment. For example, the rate of diffusion of acid throughout the feedstock decreases with decreasing temperature, and heating relatively cold feedstock to temperatures that ensure sufficient diffusion of acid during acid impregnation increases energy costs. In particular, during the winter months it is generally preferred to preheat frozen biomass feedstock to avoid rapid cooling of the dilute acidic liquid medium upon contact with the feedstock, which impedes diffusion of acid throughout the feedstock (e.g., through formation of an acid film on the surface of the feedstock). Also, relatively hot acid may be used during acid impregnation, but generally does not overcome the issues attendant relatively cold feedstock. Pre-heating the feedstock may allow for a reduced temperature of the acidic liquid medium. Thus, in various embodiments, the feedstock may be heated to temperatures up to about 40° C., up to about 50° C., or up to about 60° C. in an environment comprising an oxygen-containing gas (e.g., air or waste gas such as boiler stack gas) to reduce the moisture content and/or increase the temperature of the feedstock, e.g., to a temperature in the range of from about 30° C. to about 60° C.

Generally, the feedstock (milled as described herein or as-provided for processing) contains particles of a size in their largest dimension of less than about 6 cm (about 2.5 inches), less than about 5 cm (about 2 inches), less than about 4 cm (about 1.5 inches), or less than about 2.5 cm (about 1 inch). Typically, the feedstock contains particles of a size from about 0.01 cm (about 0.004 inches) to about 6 cm (about 2.4 inches), from about 0.1 cm (about 0.04 inches) to about 5 cm (about 2 inches), or from about 0.5 cm (about 0.2 inches) to about 4 cm (about 1.5 inches).

While not narrowly critical, the size of particulate feedstock may impact processing. For example, during acid-impregnation as detailed elsewhere herein, a significant portion of relatively large particles may provide relatively low exposed surface area for acid-biomass contact. Accordingly, it is currently believed that a significant fraction of solids within the above-noted preferred ranges promotes impregnation of the acid throughout the solids. If necessary to provide solids within the preferred range(s), the feedstock may be comminuted prior to processing to provide a feedstock of reduced and/or relatively consistent particle size (e.g., comprising particles within the above-noted preferred ranges).

FIG. 1 depicts one embodiment of a process of the present invention and, in particular, describes a process for, inter alia, production of ethanol from corn stover (e.g., field-harvested, or virgin corn stover). The feedstock may be treated in a grinder, hammer mill or other suitable comminuting device known in the art. As shown in FIG. 1, corn stover 1 is introduced into milling apparatus 5 in which the feedstock is treated to reduce the particle size of the feedstock material and produce a milled feedstock 9. If the feedstock is delivered in the form of bales, the bale wrap or strings are removed either manually or mechanically prior to grinding. The bale wrap or strings are commonly constructed of polypropylene or other plastic material which can interfere with processing of the biomass feedstock.

In accordance with various preferred embodiments, the particles of the milled feedstock may be described by various particle size parameters. For example, in various embodiments, milled feedstock comprises particles of a size distribution such that no more than about 40 wt %, no more than about 30 wt %, or no more than about 20 wt % of the feedstock particles are retained by a #10 Sieve. Additionally or alternatively, milled feedstock suitable for use in the processes of the present invention may comprise particles of a size distribution such at least about 60 wt %, at least about 70 wt %, or at least about 80 wt % of the feedstock particles are retained by a #60 Sieve.

A significant portion, or fraction of relatively fine feedstock particles may be undesired due to their impact on processing of the feedstock. For example, relatively fine particles may be lost during filtration and washing of feedstock particles, representing a loss in cellulose and/or hemicellulose. Accordingly, in various preferred embodiments, a fraction of relatively fine feedstock particles is removed prior to processing (i.e., prior to acid impregnation). For example, a fraction of feedstock particles comprising particles having a size in their largest dimension of less than about 100 microns may be removed from the feedstock prior to processing. Fractions of relatively fine particles may include a relatively high ash content (e.g., up to 40 wt %). Thus, removal of such a portion of the feedstock likewise reduces the ash proportion of the feedstock. As detailed elsewhere herein, removal of a fine particulate fraction provides a cleaned biomass feedstock exhibiting one or more advantageous properties based on the reduced ash content. For example, in various preferred embodiments cleaned biomass feedstocks provide advantageous fermentable sugar yields during pretreatment and/or enzymatic hydrolysis.

Milling, or grinding of the feedstock generally proceeds in accordance with conventional methods known in the art. In various embodiments the milling or grinding operation is conducted as a single-step operation. In such an embodiment, feedstock (e.g., de-stringed bales of biomass feedstock) is introduced into a milling apparatus suitable for providing a milled feedstock of the desired properties. For example, in various preferred embodiments suitable milling operations comprise grinding the feedstock for passage through a screen having openings of a size ranging from about 1.25 cm (about 0.5 inches) to about 4 cm (about 1.5 inches) (e.g., about 2.5 cm (about 1 inch)).

One-step milling of feedstock has generally been observed to provide feedstock of suitable particle size distributions. However, such methods may suffer one or more disadvantages. For example, wear on the screens may be accelerated due to the lack of removal of contaminants (e.g., rocks, metal, and other contaminants present in the virgin feedstock) prior to passing the feedstock over the screens. While the particle size distributions provided by one-step milling are generally suitable, the distributions may be wider than those provided by other methods. In various other preferred embodiments, milling of the feedstock proceeds via a two-step process. In such processes, feedstock (e.g., de-stringed bales of feedstock) is first subjected to relatively coarse size reduction and passed over screens for the primary purpose of removing larger particles (including contaminants) from the feedstock. Screens suitable for the first step of a two-step milling operation typically comprise openings of a size of from about 8 cm (about 3 inches) to about 12.5 cm (about 5 inches). The second step utilizes smaller screens for the purpose of isolating and recovering feedstock particles within the desired particle size distribution including, for example, screens described above in connection with one-step milling. It is currently believed that two-step milling comprising removal of larger particles prior to final milling provides for recovery of milled feedstock that is not only within the desired particle size distribution but has a narrower particle size distribution than is obtained in the single step process. However, this advantage may be offset by the increased cost associated with the additional processing. One skilled in the art may select an appropriate milling protocol based on, for example, the properties of the virgin, or untreated feedstock and the desired properties of the milled feedstock.

Regardless of whether a one-step or two-step milling operation is utilized, contaminants (e.g., rocks and/or metal) may be removed from the feedstock by passing the feedstock over magnets during, between, or after milling operations. For example, in those embodiments in which a two-step milling operation is utilized, feedstock is passed over magnets between milling operations.

In various embodiments, the feedstock (e.g., milled corn stover) may be subjected to a cleaning operation prior to further treatment to remove various impurities and contaminants (e.g., rock, dirt, sand, and other tramp materials) and feedstock particles of undesired size. Cleaning of the milled feedstock proceeds generally as known in the art including, for example, by a process comprising passing the feedstock over a suitable screen that separates desired and undesired particles. Typically, desired and undesired particles are separated by vibration and/or shaking of the screen. Contaminants (e.g., ferrous contaminants) and oversized particles and fines may also be removed by magnetic separation. Contaminants may also be removed from the feedstock by contact with a suitable flow of air (i.e., air classification) and/or contact with an aqueous washing medium (e.g., water). Water washing of the feedstock has been observed to be effective for removal of various impurities (e.g., soil and sand). However, water washing may be undesired since it may provide a relatively moist pretreated feedstock for acid impregnation, which may be undesired because it may hinder dispersion of the acid throughout the feedstock. Again with reference to FIG. 1, milled feedstock 9 is introduced into vessel 13 to form a waste stream 17 and milled and cleaned feedstock 21. In various preferred embodiments, contaminants are removed using a combination of one or more of the above-noted methods (e.g., air classification and magnetic separation).

In accordance with the process depicted in FIG. 1, milled and cleaned corn stover 21 generally has a total solids content of at least about 70 wt %, or at least about 80 wt % (e.g., about 90 wt %). The milled and cleaned corn stover is generally stored and/or processed under relatively mild to warm ambient conditions (e.g., a temperature of approximately 20° C. and atmospheric pressure).

Generally in accordance with the present invention, and with reference to the process depicted in FIG. 1, the solid portion of the cleaned and milled feedstock typically comprises a significant fraction of sugars including, for example, various polysaccharides such as glucan, xylan, arabinan, mannan, and galactan, various monosaccharides such as xylose and glucose, and combinations thereof. For example, in various embodiments, the total glucan content of the milled and cleaned corn stover is typically from about 30 wt % to about 45 wt % (dry weight basis), more typically from about 35 wt % to about 42 wt % and, still more typically, from about 37 wt % to about 40 wt %. In these and various other embodiments, the total xylan content of the milled and cleaned corn stover is typically from about 10 to about 25 wt % (dry weight basis), more typically from about 15 to about 25 wt % and, still more typically, from about 18 to about 22 wt %. Additionally or alternatively, the arabinan content of the milled and cleaned corn stover is typically from about 1 to about 5 wt % (dry weight basis), more typically from about 2 to about 4.0 wt % and, still more typically, from about 2.5 to about 3.5 wt %.

The lignin content of the milled and cleaned corn stover is typically from about 10 to about 25 wt % (dry weight basis), more typically from about 15 to about 25 wt % and, still more typically, from about 18 to about 23 wt %.

An ash portion of the milled and cleaned corn stover typically constitutes from about 2 to about 8 wt % (dry weight basis), more typically from about 3 to about 6 wt % and, still more typically, from about 4 to about 5 wt % of the milled and cleaned corn stover. The cleaned and milled corn stover also typically comprises minor proportions (e.g., from about 5 to about 12 wt %, or about 8 wt %) of various other components (e.g., acetate, uronic acid, and protein).

II. Pretreatment

Various methods for deriving fermentable sugars (e.g., glucose) from lignocellulosic biomass include acid hydrolysis utilizing relatively concentrated acids (e.g., acids having an acid content of up to 70 wt %, or greater) to dissolve and hydrolyze to glucose the cellulose component of the biomass. These methods typically provide suitable glucose yields, but generally suffer from one or more disadvantages. For example, concentrated acids require the use of specialized equipment and precise control of moisture in the system. In addition, sugars produced via the acid-catalyzed hydrolysis are often degraded by the relatively harsh hydrolysis conditions. For example, cellulose may ultimately be hydrolyzed to produce hydroxymethylfurfural rather than glucose, which may be further degraded to produce levulinic acid or formic acid. In addition, xylose produced by hydrolysis of hemicellulose may be degraded to produce furfural, tars and various other degradation products (e.g., condensation compounds associated with and/or derived from lignin).

To avoid one or more of these disadvantages, pretreatment methods have been developed that utilize a relatively dilute acid (e.g., acidic liquid media containing less than 5 wt % acid). Rather than hydrolysis of cellulose and/or hemicellulose to produce fermentable sugars, the primary purpose of dilute acid treatment (often referred to herein as acid impregnation, or pretreatment) is preparation of the feedstock for subsequent enzymatic hydrolysis to produce fermentable sugars. For example, as detailed elsewhere herein, pretreatment protocols combining dilute acid treatment and treatment of the acid-impregnated feedstock at elevated temperature and pressure (referred to elsewhere herein as steam treatment, or steam explosion) degrade, or break down the cellulose-hemicellulose-lignin complex of the biomass. In this manner, the cellulose is more susceptible to enzymatic hydrolysis to produce fermentable sugars. Increasing the susceptibility of cellulose to enzymatic hydrolysis is generally referred to herein as increasing the bioavailability or digestibility of the cellulose. Such pretreatment protocols also typically result in solubilizing at least a portion (e.g., up to or in excess of 50%) of the hemicellulose. Solubilizing hemicellulose increases the availability of cellulose to cellulase enzymes and provides hemicellulose that may be hydrolyzed to produce fermentable sugars. A further advantage of increased cellulose bioavailability is a reduction in the proportion of cellulase enzyme required to provide suitable yields of cellulose-derived fermentable sugars.

A. Acid Impregnation

Again with reference to FIG. 1, milled and cleaned feedstock (corn stover) 21 is introduced into acid impregnation vessel 25. Acid 29 introduced into acid impregnation vessel 25 typically comprises an acid selected from the group consisting of hydrochloric acid, sulfuric acid, sulfurous acid, sulfur dioxide, nitric acid, and combinations thereof. As noted, the primary purpose of acid impregnation is preparation of the feedstock for enzymatic hydrolysis to produce fermentable sugars. That is, the primary purpose of acid impregnation is increasing the bioavailability of the feedstock, rather than hydrolysis of cellulose and/or hemicellulose to produce fermentable sugars. Accordingly, acid 29 is typically in the form of a relatively dilute acid. More particularly, in accordance with the process depicted in FIG. 1, acid 29 is typically in the form of an acidic liquid medium having an acid concentration of less than about 5 wt %, less than about 4 wt %, or less than about 3 wt %. For example, typically the clean milled corn stover is contacted with an acidic liquid medium including an acid at a concentration of from about 0.2 wt % to about 4.5 wt %, preferably from about 0.7 wt % to about 3.5 wt % and, more preferably, from about 1.0 wt % to about 3.0 wt % (e.g., from about 2.0 wt % to about 2.5 wt %). Regardless of the precise composition of the acidic liquid medium, typically the biomass feedstock is contacted with (i.e., the uptake of acid by the feedstock) at least about 0.005 kg acid (e.g., $H_2SO_4$ or HCl) (acid weight basis) per kg feedstock (dry weight basis), or at least about 0.01 kg acid per kg feedstock. Preferably, the acid uptake by the feedstock is from about 0.01 kg to about 0.05 kg acid per kg of feedstock, more preferably from about 0.02 kg to about 0.04 kg acid per kg of feedstock and, still more preferably, from about 0.02 kg to about 0.03 kg acid per kg of feedstock. The solids content of acid-impregnated biomass generally ranges from 25 wt % and 50 wt %, or from about 30 wt % to about 45 wt %.

The precise configuration of acid impregnation vessel 25 is not narrowly critical and may be readily selected from suitable apparatus known in the art. For example, acid impregnation as detailed herein may be conducted in a batch reactor (e.g., a stirred-tank reactor), or a batch mixer (e.g., pug mixer, paddle mixer, ribbon mixer), or may be conducted in a vessel suitable for continuous operation (e.g., a continuous stirred-tank reactor or plug flow reactor), or a continuous mixer (e.g., pug mixer, paddle mixer, ribbon mixer, mixing screw).

The temperature of the acid 29 introduced into acid impregnation vessel 25 and/or the mixture of biomass feedstock and acid is generally at least about 30° C., at least about 40° C., or at least about 50° C. For example, in various embodiments, the temperature of the acid is from about 20° C. about 95° C., or from about 30° C. to about 75° C.

The contact time for contact of the biomass feedstock and acid by spraying or soaking is typically from about 1 minute to about 15 minutes, more typically from about 2 minutes to about 10 minutes and, more typically, from about 3 minutes to about 6 minutes. For contact by spraying, prior to further processing, the acid-sprayed corn stover is typically held in an insulated or heat-jacketed bin for from about 5 minutes to about 60 minutes, from about 10 minutes to about 45 minutes, or from about 15 minutes to about 30 minutes. In the case of feedstock contacted with the acid by soaking, the contact time is typically followed by a draining and dewatering step to remove excess acid solution and to provide an acid-impregnated feedstock of suitable solids content (e.g., from about 30 to about 65 wt %) for introduction into the pretreatment reactor.

The total flow of milled and cleaned corn stover that may be treated by the processes of the present invention and, in particular, the process depicted in FIG. 1 is not narrowly critical. The total flow of milled and cleaned corn stover depends on a variety of factors including, for example, the bulk density of the feedstock and the desired fill factor of the reactor. Generally, the total flow of milled and cleaned corn stover 21 introduced into the acid impregnation vessel (e.g., a continuous acid spray impregnation vessel) is from about 20 to about 90 pounds per hour-ft$^3$ reactor volume (lb/hr-ft$^3$ reactor volume), from about 30 to about 70 lb/hr-ft$^3$ reactor volume, or from about 40 to about 60 lb/hr-ft$^3$ reactor volume. Depending on various factors including, for example, the composition of the acidic liquid medium and/or the cleaned and milled feedstock, the total proportion of acidic liquid medium introduced into the acid impregnation vessel is generally from about 30 to about 60 pounds per hour-ft$^3$ reactor volume (lb/hr-ft$^3$ reactor volume), or from about 40 to about 50 lb/hr-ft$^3$ reactor volume. It is to be understood that the rates of introduction of feedstock and/or acidic liquid medium utilized in the process of the present invention are not narrowly critical. These flows are provided to generally indicate suitable flows, but it is currently believed that the processes of the present invention are likewise suitable for processes utilizing proportions of feedstock outside the specified ranges.

In the case of contact of the feedstock and acid by soaking, the total solids content in the acid impregnation vessel generally depends on various factors including, for example, the composition of the acidic liquid medium, the composition of the cleaned and milled feedstock, and/or the particle size distribution of the feedstock, but is generally from about to about 4 wt % to about 12 wt %, from about 5 wt % to about 10 wt %, or from about 5 wt % to about 7 wt %.

Contacting the biomass feedstock and an acidic liquid medium provides an acid-impregnated feedstock 33 in the form of a slurry comprising biomass solids dispersed throughout the acidic liquid medium. Generally, the temperature of the acid-impregnated corn stover reaches approximately the temperature of the acidic liquid medium contacted with the corn stover. That is, the temperature of the acid-impregnated corn stover is typically from about 20° C. about 95° C., or from about 40° C. to about 80° C. (e.g., about 60° C.). Additionally, the pH of the acid-impregnated corn stover is preferably less than about 4, less than about 3, or less than about 2 (e.g., about 1).

As noted, rather than preparation of fermentable sugars, the primary purpose of acid impregnation is increasing the bioavailability, or pretreatability of the feedstock. Accordingly, the composition of the acid-impregnated feedstock generally corresponds to the composition of the milled and cleaned feedstock, adjusted based on the presence of the acidic liquid medium dispersed throughout the feedstock. For example, the acid-impregnated feedstock 33 generally has a total solids content of at least about 25 wt %, or at least about 30 wt % (e.g., at least about 35 wt %, at least about 40 wt %, or at least about 45 wt %). Typically, the solids content of the acid-impregnated feedstock is from about 30 to about 70 wt %, more typically from about 35 to about 55 wt and, still more typically, from about 40 to about 50 wt %.

Typically, the total glucan content of the acid-impregnated feedstock (e.g., corn stover) is from about 25 to about 50 wt % (dry weight basis), more typically from about 30 to about 45 wt % and, still more typically, from about 35 to about 40 wt %. In these and various other embodiments, the total xylan content is typically from about 10 to about 35 wt % (dry weight basis), more typically from about 15 to about 30 wt % and, still more typically from about 20 to about 25 wt %. Additionally or alternatively, the arabinan content of the acid-impregnated feedstock is typically from about 1 to about 5 wt % (dry weight basis), more typically from about 1.5 to about 4 wt % and, still more typically, from about 2 to about 3.5 wt %.

The lignin content of the acid-impregnated feedstock (e.g., corn stover) is typically from about 10 to about 25 wt % (dry weight basis), more typically from about 10 to about 25 wt % and, still more typically, from about 15 to about 22 wt %.

The ash portion of the acid-impregnated feedstock 33 typically constitutes from about 1 to about 8 wt % (dry weight basis), more typically from about 2 to about 8 wt % and, still more typically, from about 3 to about 6 wt % of the milled and cleaned feedstock (e.g., corn stover). The acid-impregnated feedstock also typically comprises minor proportions of various other components (e.g., from about 1 to about 6 wt % or from about 1 to about 4 wt % protein, from about 1 to about 4 wt % acetyl compounds, and from about 1 to about 4 wt % uronic acids).

As detailed below, the biomass solids may be contacted by soaking in the acidic liquid medium or by spraying liquid medium onto the feedstock. Each manner of contact of the dilute acid and feedstock provides suitable impregnation. But depending on the manner of contact utilized, various strategies may be employed to promote dispersion of the acid throughout the feedstock. For example, as detailed below, when the acid is sprayed onto the feedstock, agitation or mixing may be employed to promote dispersion of the acid throughout the feedstock.

1. Soaking

For soaking of biomass feedstock, an appropriate proportion of an acidic liquid medium having an acid concentration and/or providing an acid to biomass solids ratio noted above is typically selected. The amount of liquid medium utilized may be readily selected by one skilled in the art depending on the acid concentration, amount of feedstock to be treated, etc. For example, typically the feedstock and acid are contacted by soaking the feedstock in at least about 10 kg acidic liquid medium per kg feedstock, or at least about 15 kg acidic liquid medium per kg feedstock. Utilizing a relatively high proportion of acidic liquid medium may allow utilizing dilute acids including the acids at concentrations at or near the above-noted lower limits of acid concentration (e.g., about 1.0 wt %) in view of the relatively high proportion of liquid medium contacted with the feedstock.

Soaking of the feedstock generally occurs for a time that promotes sufficient dispersion of the acid throughout the biomass feedstock solids. The duration of soaking may generally be selected based on the properties of the feedstock, the desired acid content of the resulting slurry and/or moisture content of the resulting slurry. For example, the hold time of contact by soaking (i.e., time of contact between the feedstock and acid prior to any further processing) is typically at least about 1 minute, at least about 5 minutes, or at least about 10 minutes (e.g., at least about 15 minutes, at least about 20 minutes, or at least about 25 minutes). While a suitable hold time is desired to promote impregnation of the feedstock, degradation of the fibers may begin to occur as the hold time and temperature reach certain limits. As used herein, degradation of feedstock fibers generally refers to dissolving or hydrolysis of hemicellulose, rather than break-down of the cellulose-hemicellulose-lignin complex. Thus, excessive fiber degradation reduces fermentable sugar yields and/or improvements in cellulose bioavailability and, accordingly, is preferably minimized. In various preferred embodiments the hold time for soaking contact is typically from about 1 minute to about 60 minutes, more typically from about 3 minutes to about 30 minutes and, still more typically, from about 4 minutes to about 20 minutes.

Soaking of the biomass feedstock may provide a slurry of the feedstock solids in the liquid medium having a relatively high moisture content. As detailed elsewhere herein, in various preferred embodiments, the moisture content of the acid-impregnated feedstock is below certain levels, or within various preferred ranges. Typically, the soaked biomass feedstock is dewatered to reduce its moisture content, if necessary. When contacting the biomass feedstock and acid by soaking, preferably the entire mass of feedstock is submerged in the acidic liquid medium. Submersion of the feedstock promotes bulk movement of the feedstock and/or liquid medium to provide dynamic and continuous contact of the feedstock and acidic liquid medium. To promote dynamic physical contact of the feedstock and acidic liquid medium, the feedstock/acidic liquid medium slurry is typically agitated and preferably agitated continuously. Agitation may be conducted using conventional apparatus known in the art including, for example, agitators, mixers, and mixing conveyors, depending on the acid impregnation vessel being utilized.

2. Spraying

As noted, the feedstock and acid may also be contacted by spraying an acidic liquid medium onto the biomass feedstock. The precise manner of spraying is not narrowly critical and is generally conducted in accordance with means known in the art. As compared to soaking of the feedstock in an acidic liquid medium, reduced proportions of acidic liquid medium are typically used for contact of the feedstock and acidic liquid by spraying. In this manner, material costs are reduced. To compensate for the reduction of proportion of liquid medium, approaches may be taken to promote dispersion of the acid throughout the feedstock.

For example, generally the biomass feedstock is agitated while the acidic liquid medium is sprayed onto the feedstock and/or upon completion of spraying of the acidic liquid medium onto the feedstock. More particularly, the feedstock is agitated to distribute the acidic liquid medium throughout the feedstock and bring particles into contact with other particles. In various preferred embodiments, agitation provides mutually abrading contact of the particles and the resulting rubbing action between the particles promotes distribution of the acidic liquid medium throughout the feedstock. Typically, the feedstock is agitated for a period of from about 1 to about 10 minutes and, more typically, for from about 2 to about 5 minutes. In certain preferred embodiments, the feedstock and acidic liquid medium are contacted in a suitable vessel comprising counter-rotating shafts that provide agitation of the feedstock in a manner that promotes distribution of the medium throughout the feedstock.

As detailed elsewhere herein, acid-impregnated feedstock preferably exhibits moisture contents within various preferred ranges (e.g., less than about 70 wt % or less than about 50 wt %). Soaking of the biomass typically provides a slurry having a moisture content that necessitates dewatering to achieve such often-preferred moisture contents. In contrast, spraying of dilute acid is controlled to prepare acid-impregnated feedstock that typically exhibits a moisture content at the conclusion of the spraying step that falls within these preferred ranges, thereby avoiding the need for dewatering. Accordingly, contact by spraying may be preferred in various embodiments.

As with contact by soaking, the biomass feedstock and acidic liquid medium are generally contacted for a time sufficient to suitably disperse the acid throughout the feedstock. Often, the reduced proportion of liquid medium utilized in contact by spraying may lead to increased contact, or hold times for acid impregnation. For example, the hold time may be at least about 10 minutes, at least about 20 minutes, or at least about 40 minutes. However, preferably the reduced proportion of the acidic liquid medium is compensated for by agitation of the biomass. Accordingly, typically the hold time for spraying contact is no more than about 60 minutes, more typically no more than about 40 minutes and, still more typically, no more than about 20 minutes. In various preferred embodiments, the hold time is from about 2 to about 35 minutes, from about 5 to about 30 minutes, or from about 10 to about 20 minutes.

3. Wetting Agent

Regardless of its precise composition (e.g., moisture content) or its manner of contact with the feedstock (e.g., by soaking or spraying), the acidic liquid medium contacted with the feedstock may include a surfactant, or wetting agent to promote dispersion of the acid throughout the resulting acid-impregnated biomass slurry. More particularly, including a surfactant(s) in the acidic liquid medium may reduce the surface tension of the liquid medium to promote dispersion of the liquid medium and acid contained therein throughout the biomass feedstock. Suitable surfactants are generally biodegradable and non-toxic and generally include commercially available surfactants (e.g., various anionic, cationic, and nonionic surfactants). Based on the lower proportion of acidic liquid medium utilized, use of a wetting agent during acid impregnation is often preferred in those embodiments in which the feedstock is contacted with the acidic liquid medium by spraying.

Suitable anionic surfactants include alkyl sulfate salts, arylalkyl sulphonates, fatty acid salts, and combinations thereof. For example, commercially available anionic surfactants include, for example, DOWFAX and TRITON (Dow Chemicals), BIO-TERGE (Stepan), and OT-A (Cytec). Suitable cationic surfactants include alkyl quaternary ammonium salts including, for example, the commercially available PRAEPAGEN surfactants (Clariant). Suitable nonionic surfactants include alcohol ethoxylates (e.g., alkyl polyethylene oxides), alcohol propoxylates, alcohol ethoxyalte-propoxylates, fatty alcohols, and combinations thereof. Commercially available nonionic surfactants include, for example, TERGITOL 15-S-12 and TRITON DF-16 (Dow Chemicals), SILWET L-77 (Helena Chemical Co.), and Activator 90 (Loveland Products, Inc.). In various embodiments, nonionic surfactants are preferred as their performance is generally unaffected by the presence of an acidic liquid medium.

In addition to the above-noted surfactants, suitable wetting include various alcohols such as, for example, methanol, ethanol, propanol, and butanol. Advantageously, alcohols suitable for use as surfactants may be generated elsewhere in the process and recycled to the acid impregnation vessel.

Additionally or alternatively, in various preferred embodiments the biomass feedstock and surfactant may be contacted prior to contact of the feedstock and acid. For example, feedstock (optionally subjected to milling and/or a cleaning operation) may be contacted with an amount of wetting agent prior to acid impregnation. The feedstock may be contacted with the wetting agent by soaking the feedstock in a suitable proportion of wetting agent or liquid medium comprising a suitable proportion of wetting agent. Preferably, the feedstock and wetting agent are contacted by spraying onto the feedstock a suitable portion of wetting agent or a liquid medium comprising the wetting agent. Although contact of the feedstock and wetting agent disperses wetting agent throughout the feedstock, dispersion of the wetting agent throughout the feedstock occurs primarily during dispersion of the acid throughout the feedstock during acid impregnation.

4. Heating During Acid Impregnation

In various embodiments, heating during contact of the biomass feedstock and dilute acid is employed to promote dispersion of the acid throughout the resulting acid impregnated biomass slurry. Typically, any heating for this purpose involves heating the biomass feedstock/dilute acid mixture to temperatures of at least about 10° C., at least about 20° C., or at least about 40° C. However, solubilization of the hemicellulose component of the biomass feedstock preferably does not occur to any significant degree during acid impregnation but, rather, preferably occurs during subsequent processing (e.g., steam pretreatment and/or enzymatic hydrolysis as detailed elsewhere herein). Accordingly, the temperature during acid impregnation and any heating of the feedstock and dilute acid associated therewith is preferably controlled to minimize, and preferably avoid solubilization of hemicellulose. Based on the foregoing, temperatures of acid impregnation (and any associated heating) are preferably maintained at no more than about 100° C., no more than about 90° C., or no more than about 80° C. Thus, in accordance with the foregoing, preferably the temperature during acid impregnation is from about 10° C. to about 100° C., more preferably from about 30° C. to about 90° C. and, still more preferably, from about 40° C. to about 80° C.

In addition to contributing to solubilization of hemicellulose, contacting the feedstock with moisture prior to contact with acid may be undesired since the moisture may be dispersed throughout the feedstock and inhibit dispersion of acid throughout the biomass feedstock and/or result in relatively uneven acid dispersion throughout the biomass feedstock. Thus, in accordance with those embodiments in which the feedstock is heated during acid impregnation, the feedstock is heated in the presence of a relatively low moisture environment. Generally, the feedstock is heated in the presence of an environment having a relative humidity of less than about 100%, or less than about 80%. In accordance with various preferred embodiments, the feedstock is heated in the presence of air heated to a temperature of at least about 20° C., or at least about 40° C. The feedstock may also be heated by contact with a flue gas at such temperatures.

5. Steaming Prior to Acid Impregnation

Although desired in certain situations including, for example, when the incoming biomass feedstock is stored at relatively low temperatures such as during the winter months, heating of the biomass feedstock is often undesired as it increases energy and operating costs. Thus, rather than heating, in various embodiments the biomass feedstock is contacted with steam prior to contact with acid. That is, in various preferred embodiments is subjected to a pre-steaming operation prior to acid impregnation. Pre-steaming of the biomass feedstock provides various advantages. For example, pre-steaming removes regions throughout the biomass feedstock largely made up of air pockets that during acid impregnation will provide uptake of the acid, but do not contribute to uptake of acid by feedstock particles. Injecting steam throughout the feedstock removes aerified portions of the feedstock and the steam-containing regions of the feedstock are removed when the steam-infused feedstock is contacted with the acidic liquid medium. Removal of these steam pockets upon contact of the feedstock structure with the acidic liquid medium causes the feedstock to collapse and provide a feedstock with a substantial portion, and preferably near all of the air pockets that do not contribute to effective acid impregnation removed. In this manner, pre-steaming provides a biomass feedstock that promotes more effective acid impregnation by removal of regions throughout the biomass feedstock mass that do not contribute to uptake of the acid by feedstock particles. Pre-steaming also allows for use of an acidic liquid medium at lower temperatures as compared to liquid media typically used in the connection with feedstocks that have not been subjected to pre-steaming. Pre-steaming may be conducted in accordance with methods and utilizing apparatus generally known in the art including, for example, as described in U.S. Pat. Nos. 3,383,277 and 4,746,404, the entire contents of which are incorporated by reference for all relevant purposes.

Generally during pre-steaming, the biomass feedstock is contacted with steam in a suitable vessel or reactor. Typically, the biomass feedstock is contacted with steam introduced into the vessel under a steam pressure of about 5 psig and steam temperature of about 110° C., a steam pressure of about 10 psig and a steam temperature of about 115° C., or a steam pressure of about 15 psig and steam temperature of about 120° C. Typically, the biomass feedstock is contacted with steam at a temperature of from about 100 to about 130° C., from about 100 to about 120° C., or from about 100 to about 110° C. Generally, steam is introduced into the vessel at a rate of at least about 10 kg/hour, or from about 10 to about 20 kg/hour. Although not narrowly critical, generally pre-steaming is conducted for a time of from about 5 to about 30 minutes, or from about 10 to about 20 minutes. In various embodiments, a minor portion of the dilute acid may be introduced into the pre-steaming vessel. For example, an acidic liquid medium containing an acid at a concentration of less than about 3 wt %, less than about 2 wt %, less than about 1 wt %, or less than about 0.5 wt % may be introduced into the pre-steaming vessel. The total proportion of acidic liquid medium is not narrowly critical and generally depends on the manner of contact of the feedstock and acidic liquid medium. For example, the acidic liquid medium and feedstock may be contacted at a proportion of from about 0.5 to about 15 g acidic liquid medium per gram feedstock introduced into the pre-steaming vessel.

6. Ash Removal

While acid-impregnation in accordance with the foregoing description has been found to suitably impregnate the feedstock, various treatments prior to impregnation may be employed to improve the efficiency of this operation. For example, ash present in the feedstock may consume the acid (e.g., by reaction to form salts) and, thus, reduce impregnation of the acid throughout the feedstock. As the proportion of ash approaches and/or exceeds the above-noted upper limits of ash concentration, ash removal may be preferred prior to acid impregnation. Removal of ash from the feedstock may be conducted by, for example, washing of the acid-impregnated feedstock as detailed elsewhere herein, or by passing the feedstock over a suitable screen for removal of fines and loose particles (e.g., dirt).

Generally, the ash portion of the biomass feedstock includes various components such as silica, calcium-containing components, magnesium-containing components, sodium-containing components, potassium-containing components, phosphorus-containing components, aluminum-containing components, and combinations thereof. Typically, the ash content of the biomass feedstock is from about 1 wt % to about 10 wt % or from about 3 wt % to about 10 wt % for non-woody biomass, or from about 0.1 wt % to about 5 wt % or from about 0.1 wt % to about 2 wt % for woody biomass. The ash content of biomass feedstock generally includes an acid soluble fraction and an acid insoluble fraction. The acid insoluble ash fraction generally comprises silica. Typically, silica constitutes the major portion of the insoluble fraction and typically constitutes at least about 1 wt %, or at least about 3 wt % of the biomass feedstock. Generally, the acid soluble ash fraction constitutes at least about 30 wt %, or at least about 40 wt % (e.g., from about 40 wt % to about 50 wt % of the ash of the feedstock). The acid insoluble ash fraction typically constitutes at least about 50 wt %, or at least about 60 wt % (e.g., from about 50 wt % to about 60 wt % of the ash of the feedstock).

For example, corn stover typically has an ash content of at least about 3 wt % or from about 3 wt % to about 10 wt %. Additionally or alternatively, corn stover typically has a silica content of at least about 1 wt %, at least about 3 wt %, or at least about 5 wt % (e.g., from about 1 wt % to about 7 wt % or from about 1 wt % to 5 wt %, or from about 3 wt % to 5 wt %). Generally, the acid soluble ash fraction of corn stover constitutes from about 35 to about 45 wt % of the ash and the acid insoluble ash fraction constitutes from about 55 wt % to about 65 wt % of the ash of the feedstock.

Wheat straw typically has an ash content of at least 3 wt % or from about 3 wt % to about 10 wt %. Additionally or alternatively, wheat straw typically has a silica content of at least about 1 wt %, from about 1 wt % to about 7 wt % or from about 1 wt % to 5 wt %. Generally, the acid soluble ash fraction of wheat straw constitutes from about 35 to about 45 wt % of the ash and the acid insoluble ash fraction constitutes from about 55 wt % to about 65 wt % of the ash of the feedstock.

Woody biomass feedstocks generally have an ash content of less than about 5 wt % or less than about 2 wt %. Typically, woody biomass feedstocks have an ash of from about 0.1 wt % to about 5 wt % or more typically from about 0.1 wt % to about 2 wt %. Generally, woody biomass feedstocks have a silica content less than about 0.2 wt % or from about 0.01 wt % to about 0.2 wt %.

7. Dry Cleaning

As noted, the ash portion of biomass feedstocks utilized in accordance with the present invention typically includes one or more inorganic components such as, for example, silica, calcium-containing components, magnesium-containing components, sodium-containing components, potassium-containing components, phosphorus-containing components, aluminum-containing components, and combinations thereof. These inorganic components may interfere with acid impregnation for the purpose of preparation of the feedstock for enzymatic hydrolysis to produce fermentable sugars. More particularly, these components may react with and/or neutralize the acid utilized in acid impregnation, thereby rendering at least a portion of the acid contacted with the biomass feedstock significantly less effective or even ineffective for acid impregnation and preparation of the feedstock for enzymatic hydrolysis to produce fermentable sugars. Compensating for the reduction in effectiveness of the acid for impregnation may require additional acid loading either in the form of a more concentrated acidic liquid medium and/or utilizing additional acidic liquid medium in the acid impregnation step. Utilizing a more concentrated acidic liquid medium is generally undesired based on handling concerns and/or the increased risk of equipment corrosion. Utilizing additional acidic liquid medium likewise raises these concerns and also generation of additional waste liquid that must be handled and disposed. Thus, a need exists for a method for providing a biomass feedstock having a significant portion of the ash fraction removed, thereby preferably avoiding the need for providing additional acid either through use of a more concentrated acidic liquid medium and/or use of additional acidic liquid medium.

Inorganic components of ash, such as, for example, silica, may also negatively affect process equipment by increasing wear, particularly on moving parts. Therefore removal of a significant portion of ash may also beneficially increase the life of process equipment.

In accordance with the present invention, it has been discovered that a significant fraction of the ash portion may be removed from the biomass feedstock by a process in which various fractions are removed from the biomass feedstock prior to acid impregnation. Generally, removal of ash from the biomass feedstock for the purpose of improving the effectiveness of acid impregnation includes removal of a fine particulate fraction from the biomass feedstock prior to acid impregnation. Additionally, the method may include removal of a fraction rich in dense contaminants from the biomass feedstock. This dense contaminant fraction contains various components that are undesired since they do not contribute to fermentable sugar and/or ethanol yield and their presence may inhibit preparation of the feedstock for recovery of fermentable sugars and recovery of fermentable sugars. Removal of these fractions generally proceeds by one or more separation, or classification techniques. As used herein, the terms "classified," "classifying," or "classification" refer to any operation that is capable of separating the solids component of a biomass feedstock into two or more fractions having different particle size ranges. Several classification techniques may be used in accordance with the present invention. For example, suitable classification techniques include air classifying, screen separation, filtration, and sedimentation techniques or by means of a cyclone separator. In various preferred embodiments as detailed herein, separating the solids component of a biomass feedstock into two or more fractions having different particle size ranges is conducted by air classification and/or screen separation.

Removal of the ash portion of the biomass feedstock in accordance with the present invention by a combination of one or more classifying and/or screening operations generally proceeds in the absence of adding moisture to the biomass feedstock by, for example, contacting the biomass feedstock or any fractions removed therefrom with wash water. Accordingly, the methods for removal of the ash fraction from the feedstock detailed herein may conveniently be referred to as "dry cleaning" methods. Avoiding addition of wash water at this stage in the process provides many advantages. The fine particulate fraction of the biomass feedstock is rich in ash content. Water washing methods are known that remove fine particulates. However, in addition to removal of the fine particulate fraction, water washing also dissolves a portion of soluble components of the biomass feedstock including, for example, cellulose, hemicellulose, and starches. Removal of these soluble components at this point in the process reduces fermentable sugar and/or ethanol yields during later processing. In addition, water washing may be undesired since it may provide a relatively moist feedstock for acid impregnation, which may be undesired because it may hinder dispersion of the acid throughout the feedstock. The dry cleaning methods detailed herein provide removal and recovery of the ash fraction in the form of a fine particulate fraction, but without undesired removal of soluble components of the biomass feedstock. Dry cleaning ash removal methods are likewise advantageous since they do not introduce additional liquid loading to the process, which would add to the proportion of wastewater to be disposed of and/or cleaned prior to use. In addition, as noted above and detailed elsewhere herein, removal of a fine particulate fraction rich in ash content contributes to improving the effectiveness of acid impregnation.

As noted, the ash component of the biomass feedstock includes an acid soluble fraction and an acid insoluble fraction. The dry cleaning methods detailed herein are effective for removal of a fine particulate fraction including both acid soluble and acid insoluble ash components and may provide removal of a greater proportion of total ash than provided by water washing, but without the concomitant removal of desired soluble components and problems associated with use of a moist feedstock in acid impregnation. However, since wash water is not utilized typically the remaining ash fraction of biomass feedstocks cleaned in accordance with the present dry cleaning methods may include a greater proportion of acid soluble ash components than remaining after water washing. Thus, the soluble ash fraction of cleaned biomass feedstocks provided by the present invention may constitute a greater proportion of the total ash content of cleaned feedstocks provided by water washing. Thus, cleaned biomass feedstocks provided by the dry cleaning methods detailed herein may provide a cleaned biomass feedstock having a lower ash content than provided by wet cleaning, but an ash content identified by a higher proportion of acid soluble ash components relative to the total ash content of the cleaned biomass feedstock and/or acid insoluble components as compared to water washing methods. In this manner, cleaned biomass feedstocks provided by the present invention are identified, or marked by the proportion of soluble ash components of the ash fraction. Although these ash components are soluble during acid impregnation, such cleaned biomass feedstocks are suitable for acid impregnation because of the low overall ash content.

Figure 1A:
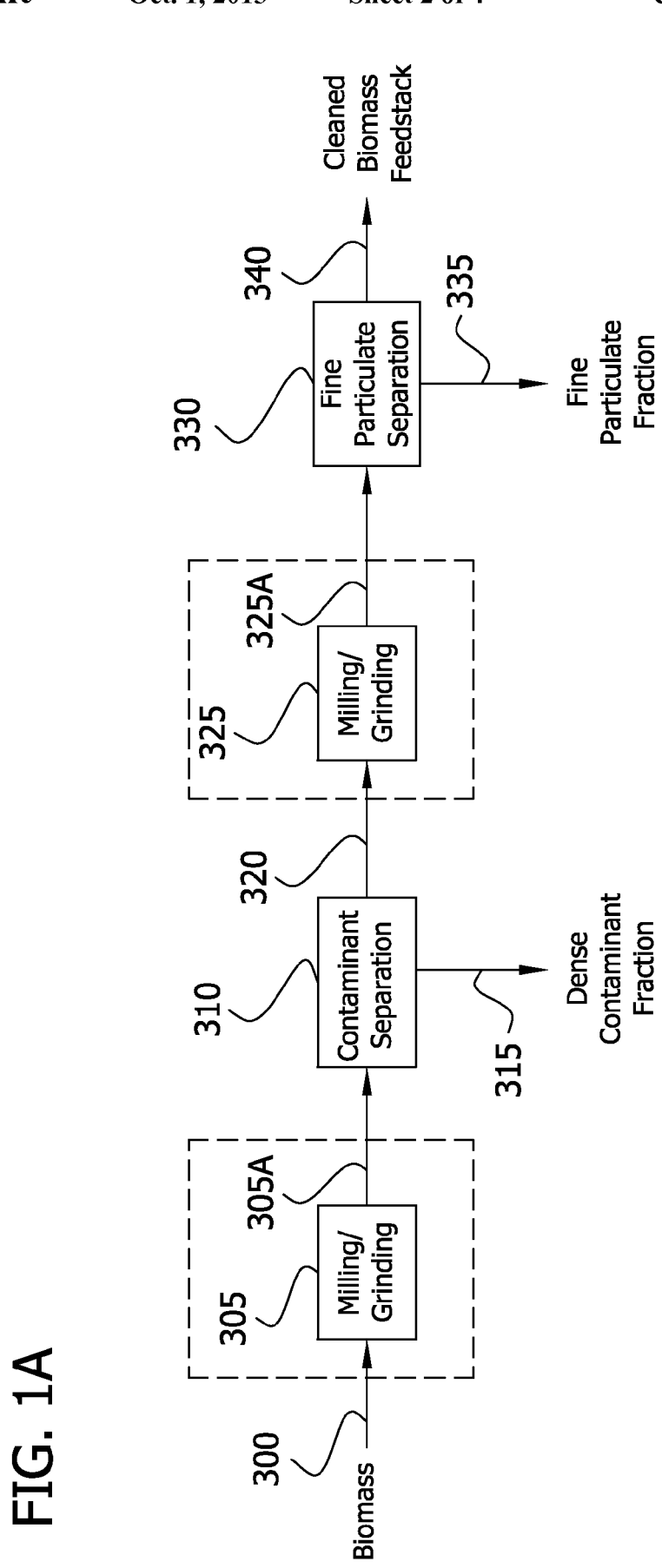
FIG. 1A depicts a dry cleaning method of the present invention.

FIG. 1A depicts a dry cleaning method of the present invention. As shown in FIG. 1A, biomass feedstock 300 is introduced into a contaminant separation system 310 for removal of a dense contaminant fraction 315 from the biomass feedstock to provide a biomass feedstock 320. Additionally, biomass feedstock 320 is introduced into a fine particulate separation zone 330 for removal of a fine particulate fraction 335 from the biomass feedstock to provide a cleaned biomass feedstock 340.

Optionally as shown in FIG. 1A, biomass feedstock 300 may be subjected to a particle size reduction operation (e.g., milling or grinding) in a suitable vessel or zone (i.e., 305 shown in FIG. 1A) to provide biomass feedstock 305A for introduction into contaminant separation zone 310. Additionally or alternatively, biomass feedstock 320 exiting the contaminant separation zone may be subjected to a particle size reduction operation in a suitable zone or vessel (i.e., 325 shown in FIG. 1A) to provide a biomass feedstock 325A for introduction into fine particulate separation zone 330.

In various preferred embodiments, the one or more optional particle size reduction operations provides a biomass feedstock 305A for introduction into the contaminant separation zone 310 and/or a biomass feedstock 325A for introduction into the fine particulate separation zone 330 having a preferred particle size distribution. For example, typically biomass feedstock 305A and/or biomass feedstock 325A is in the form of a particulate biomass feedstock comprising particles having a particle size distribution such that no more than from about 20 to about 40 wt % of the feedstock particles are retained on a screen having openings of about U.S. Sieve No. 5 (4 mm) In various other preferred embodiments, the biomass feedstock is in the form of a particulate biomass feedstock comprising particles having a particle size distribution such that from about 90 to about 95 wt % of the feedstock particles are retained on a screen having openings of about U.S. Sieve No. 60 (250 µm).

(i) Contaminant Separation Zone

Again with reference to FIG. 1A, in accordance with various preferred embodiments, contaminant separation zone 310 comprises one or more air classifier(s) in which the biomass feedstock is contacted with a gas stream (e.g., air) in the air classifier(s). Suitable air classifiers include air density separators, cyclone separators, falling bed aspirators, and turbo air classifiers. Operation of the air classifier generally proceeds in accordance with methods known in the art and depending on the composition of the biomass feedstock introduced into the contaminant separation zone (e.g., the proportion of the feedstock constituted by the dense contaminant fraction to be removed). Generally, the air velocity within the air classifier is maintained (e.g., by adjusting the damper) such that the dense, or heavy contaminants are not carried forward, or through the air classifier with the air flow. In various embodiments of the present invention, the contaminant separation zone includes a series of air classifiers wherein the biomass feedstock is contacted with the gas stream in each of the series of air classifiers, thereby forming a plurality of dense contaminant fractions and a plurality of biomass feedstock fractions depleted in dense contaminants. In these and other embodiments the contaminant separation zone includes at least 2, at least 3, or at least 4 air classifiers.

In various other embodiments, the contaminant separation zone includes at least one classifying screen, thereby recovering the dense contaminant fraction on the at least one classifying screen and the biomass feedstock depleted in dense contaminants having passed through the at least one classifying screen. In these embodiments the at least one classifying screen of the contaminant separation zone typically has openings of a size at least about 0.5 inches (12.7 mm) or from about 0.5 inches (12.7 mm) to about 1 inch (25.4 mm). Typically, dense contaminant fraction 315 removed from the biomass feedstock utilizing the contaminant separation zone comprises one or more components selected from the group consisting of gravel and metal impurities. The dense contaminant fraction also typically contains biomass feedstock particles having a particle size distribution such that at least about 95 wt % of the particles are retained on a screen having openings of a size of about 0.5 inches (12.7 mm).

(ii) Fine Particulate Separation Zone

Again with reference to FIG. 1A, biomass feedstock 320 (or optionally 325A) is introduced into a fine particulate separation zone 330 for removal of a fine particulate fraction 335 and formation of a cleaned biomass feedstock 340. Generally, fine particulate separation zone 330 comprises at least one classifying screen to recover the cleaned biomass feedstock 340 on the at least one classifying screen and the fine particulate fraction 335 having passed through the screen. Various types of screens may be used in the screen classification system including, for example, woven wire screens and/or wedge wire screens.

In various preferred embodiments, the screen separation system includes one screen. Typically, the screen has openings of a size of from about U.S. Sieve No. 100 (150 µm) to about U.S. Sieve No. 20 (840 µm) or from about U.S. Sieve No. 80 (175 µm) to about U.S. Sieve No. 60 (250 µm). For example, typically the screen separation system comprises a screen having openings of a size of about U.S. Sieve No. 20 (840 μm), about U.S. Sieve No. 60 (250 μm), about U.S. Sieve No. 80 (175 μm), or about U.S. Sieve No. 100 (150 μm).

In various other embodiments, the screen separation system comprises two screens. Typically, the first screen has openings of a size of from about 0.5 inches to about 1 inch and the second screen has openings of a size of from about U.S. Sieve No. (840 μm) to about U.S. Sieve No. 100 (150 μm).

In still further embodiments, the screen separation system comprises three screens or four screens including, for example, one or more screens having openings of a size of from about 0.5 inches to about 1 inch and arranged, for example, in series and one or more screens having openings of a size of from about U.S. Sieve No. (840 μm) to about U.S. Sieve No. 100 (150 μm) arranged, for example, in series.

In various preferred embodiments the contaminant separation zone and fine particulate separation zone are combined in a single zone that includes one or more air classifiers equipped with one or more classifying screens. Accordingly, in these embodiments, utilizing one or more air classifiers further comprising one or more classifying screens provides for the recovery of (i) a dense contaminant fraction retained on the at least one classifying screen, (ii) a cleaned biomass feedstock having passed through the at least one classifying screen, and (iii) a fine particulate fraction having been entrained in the gas stream exiting the air classifier. In various embodiments, the at least one classifying screen of the air classifier has openings of a size at least about 0.5 inches (12.7 mm) or from about 0.5 inches (12.7 mm) to about 1 inch (25.4 mm).

The contaminant separation zone and/or fine particulate separation zone may include a magnetic separation system to remove a ferromagnetic fraction from the biomass feedstock prior to removal of the fine particulate fraction therefrom and/or biomass feedstock depleted in dense contaminants. The location or position of the magnetic separation system is not narrowly critical and may be placed at any point in the cleaning process that is effective for removal of such ferromagnetic fraction.

(iii) Fine Particulate Fraction

As noted, it is currently believed that a significant fraction of the ash portion of the biomass feedstock is present in the form of relatively small particulates. Since the ash portion of the biomass feedstock contains various components that impede or interfere with acid impregnation, removal of a fine particulate fraction and the concomitant removal of a significant portion of the ash fraction of the biomass is advantageous since it contributes to improved effectiveness of the acid impregnation. In accordance with the present invention it has been discovered that recovering a fine particulate fraction comprising particles within various preferred size ranges provides for advantageous removal of a significant fraction of the ash portion of the biomass feedstock present in the fines of the biomass feedstock. For example, in accordance with various preferred embodiments, at least about 95 wt % of the fine particulate fraction passes through a screen having openings from about U.S. Sieve No. 100 (150 μm) to about U.S. Sieve No. 20 (840 μm). In various other embodiments, at least about 95 wt % of the fine particulate fraction passes through a screen having openings from about U.S. Sieve No. 80 (175 μm) to about U.S. Sieve No. 60 (250 μm). In still further preferred embodiments, at least about 95 wt % of the fine particulate fraction passes through a screen having openings of about U.S. Sieve No. 60 (250 μm), through a screen having openings of about U.S. Sieve No. 80 (175 μm), or through a screen having openings of about U.S. Sieve No. 100 (150 μm).

In addition to the particle size distribution, ash content of the fine particulate fraction may also indicate effective cleaning of the feedstock. Since a significant fraction of the ash content of the biomass feedstock is present in fine particulates, the fine particulate fraction typically has significantly higher ash content (i.e., weight percent ash) than the biomass feedstock introduced into the particulate size separation system 330. Generally, the fine particulate fraction has an ash content of at least about 30 wt %, at least about 40 wt %, or at least about 50 wt %. Typically, the fine particulate fraction has an ash content of from about 30 wt % to about 80 wt %, more typically from about 40 to about 70 wt % and, still more typically from about 45 to about 60 wt %. Typically, the fine particulate fraction has a silica content of at least about 30 wt %, at least about 40 wt %, or from about 30 wt % to about 50 wt %, or from about 40 wt % to about 50 wt %.

Generally, an acid soluble ash fraction constitutes from about 20 wt % to about 40 wt % of the ash of the fine particulate fraction. Typically, potassium constitutes at least about 30 wt % or from about 35 wt % to about 45 wt % of the acid soluble fraction. An acid insoluble fraction generally constitutes from about 60 wt % to about 80 wt % of the ash of the fine particulate fraction. Typically, silica constitutes at least about 90 wt % or at least about 95 wt % (e.g., from about 95 to about 99 wt %) of the acid insoluble fraction.

In addition to the absolute proportion of ash content of the fine particulate fraction, the proportion of ash present in the fine particulate fraction relative to the ash content of the biomass feedstock is an indicator of effective ash removal. For example, generally the ratio of the ash content (wt % ash) of the fine particulate fraction to the ash content of biomass feedstock is at least about 3:1, at least about 4:1, at least about 5:1, at least about 6:1, at least about 7:1, or at least about 8:1. For example, in various preferred embodiments in which the ash content of the biomass feedstock is from about 8 wt % to about 12 wt %, the ash content of the fine particulate fraction is at least about 40 wt %, at least about 50 wt %, at least about 60 wt %, from about 40 wt % to about 90 wt %, from about 40 wt % to about 80 wt %, or from about 50 wt % to about 80 wt %.

Generally, the fine particulate fraction has a moisture content of less than about 20 wt %, less than about 15 wt %, or less than about 10 wt %. Typically, the fine particulate fraction has a moisture content of from about 1 wt % to about 20 wt %, more typically from about 1 to about 15 wt % and, still more typically, from about 1 wt % to about 10 wt %. Generally, the fine particulate fraction has a cellulose content of from about 10 wt % to about 40 wt %, a hemicellulose content of from about 10 wt % to about 30 wt %, and/or a lignin content of from about 5 wt % to about 25 wt %.

(iv) Cleaned Biomass Feedstock

As noted, removal of various fractions from the biomass feedstock in accordance with the present invention as depicted in FIG. 1A provides a cleaned biomass feedstock having various contaminants removed therefrom including, for example, various dense contaminants and a fine particulate fraction rich in ash content.

Generally, the cleaned biomass feedstock has an ash content of less than about 10 wt %, less than about 9 wt %, less than about 8 wt %, less than about 7 wt %, less than about 6 wt %, less than about 5 wt %, less than about 4 wt %, less than about 3 wt %, less than about 2 wt %, or less than about 1 wt %. For example, typically the ash content of the cleaned biomass feedstock is from about 0.1 wt % to about 10 wt %, from about 0.1 wt % to about 8 wt %, or from about 0.1 wt % to about 7 wt %, from about 0.1 wt % to about 6 wt %, or from about 0.1 wt % to about 5 wt %.

In addition to a low proportion of total ash content, removal of a significant fraction of the ash component of the biomass feedstock may also be indicated by the proportion of ash content of the cleaned biomass feedstock as compared to the starting ash content of the feedstock. For example, in various embodiments, the ash content of the cleaned biomass feedstock (i.e., wt % ash) is no more than about 75%, no more than about 70%, no more than about 65%, no more than about 60%, no more than about 55%, of the ash content of the biomass feedstock (dry weight basis). Typically, the ash content of the cleaned biomass feedstock is no more than about 50%, no more than about 45%, or no more than about 40% of the ash content of the biomass feedstock (dry weight basis).

As noted, the ash portion of the biomass feedstock and fractions removed therefrom includes soluble and insoluble components. Generally, the ash content of the cleaned biomass feedstock indicates removal of a significant fraction of the ash of the biomass feedstock. However, as compared to water washing methods, the ash content of the cleaned biomass feedstock provided by the present dry cleaning methods typically includes a higher fraction of acid soluble ash components. For example, typically the acid soluble ash fraction constitutes at least about 30 wt %, at least about 35 wt %, or at least about 40 wt % (e.g., from about 35 wt % to about 45 wt % or from about 40 wt % to about 45 wt %) of the cleaned biomass feedstock ash content. Retention of an acid soluble ash fraction in cleaned biomass feedstocks in accordance with the present invention thus represents removal of undesired ash from the biomass feedstock, but without the attendant disadvantages of water washing (e.g., removal of other desired soluble components of the biomass feedstock such as cellulose, hemicellulose, and other starches).

Effective cleaning methods may also be indicated by the relative proportions of the ash content of the fine particulate fraction and cleaned biomass feedstock. For example, typically the ratio of the ash content of the fine particulate fraction (wt % ash) to the ash content of the cleaned biomass feedstock is at least about 3:1, at least about 4:1, or at least about 5:1. In accordance with various preferred embodiments, the ratio of the ash content of the fine particulate fraction (wt % ash) to the ash content of the cleaned biomass feedstock is at least about 6:1, at least about 7:1, at least about 8:1, at least about 9:1, at least about 10:1, at least about 11:1, at least about 12:1, at least about 13:1, at least about 14:1, or at least about 15:1.

Generally, the cleaned biomass feedstock has a moisture content of less than about 20 wt %, less than about 15 wt %, or less than about 10 wt %. Typically, the cleaned biomass feedstock has a moisture content of from about 1 wt % to about 20 wt %, more typically from about 3 to about 15 wt % and, still more typically, from about 5 wt % to about 10 wt %. As noted, the dry cleaning methods detailed herein are advantageously conducted in the absence of addition of liquid, or wash water for the purpose of removing contaminants. Accordingly, the moisture content of the feedstock and fractions removed therefrom are relatively constant. For example, generally the moisture content of one or more and preferably each of the biomass feedstock, dense contaminant fraction, biomass feedstock depleted in dense contaminants, cleaned biomass feedstock, and fine particulate fraction vary by no more than about 10 wt %, no more than about 5 wt %, or no more than about 3 wt %. Typically, the moisture content of one or more and preferably each of the biomass feedstock, dense contaminant fraction, biomass feedstock depleted in dense contaminants, cleaned biomass feedstock, and fine particulate fraction vary by no more than about 1 wt %.

Generally, the cleaned biomass feedstock has a cellulose content of at least about 30 wt % or from about 30 wt % to about 60 wt %. Generally, the cleaned biomass feedstock has a hemicellulose content of at least about 20 wt % or from about 20 wt % to about 40 wt %. Generally, cleaned biomass feedstock has a lignin content of at least about 10 wt % or from about 10 wt % to about 25 wt %.

Typically, the cleaned biomass feedstock has a particle size distribution such that at least about 95 wt % of the particles are retained on a screen having openings of a size of about U.S. Sieve No. 60 (250 µm). Typically, the cleaned biomass feedstock has a particle size distribution such that from about 95 to about 99 wt % of the biomass feedstock is retained on a screen having openings of about U.S. Sieve No. 60 (250 µm).

8. Power Requirements

Preferably, acid impregnation is conducted in a manner that balances effective impregnation with power consumption, and the costs associated therewith. It is currently believed that many factors affect the required power to provide effective acid impregnation including, for example, the composition of the feedstock and/or acidic liquid medium. Additionally or alternatively, the conditions of contact including, for example, contact time, contact temperature, and manner of contact (e.g., by spraying or soaking). Generally in accordance with the present invention (and as detailed in Example 2), it has been observed that power inputs of less than about 10 kilowatt hours per ton corn stover (kWh/ton), or less than about 8 kWh/ton provide effective acid impregnation. Typically, the power input ranges from about 1 to about 8 kWh/ton or from about 3 to about 6 kWh/ton.

9. Acid-Impregnated Feedstock

Contact of the feedstock and acidic liquid medium generally provides an acid-impregnated feedstock (33 in FIG. 1) in the form of a slurry or cake of particulate biomass dispersed throughout a liquid medium.

Relatively low moisture content of the acid-impregnated feedstock generally reduces the energy required during subsequent heating. Accordingly, in various preferred embodiments the acid-impregnated feedstock generally has a moisture content of less than about 70 wt %, typically less than about 60 wt %, more typically less than about 55 wt % and, still more typically, less than about 50 wt %. Such moisture contents may be achieved by spraying an acidic liquid medium onto the feedstock, soaking the feedstock in an appropriate proportion of acidic liquid medium and/or soaking the feedstock followed by dewatering.

In addition to promoting dispersion of the acid throughout the feedstock, a certain proportion of moisture in the acid-impregnated feedstock is preferred in order to significantly minimize, and preferably substantially avoid the risk of pyrolysis of the feedstock during subsequent treatment at elevated temperature and pressure (e.g., steam treatment as detailed elsewhere herein). Thus, typically the moisture content of the acid-impregnated feedstock is at least about 20 wt %, more typically at least about 30 wt % and, still more typically, at least about 40 wt %.

Accordingly, in various preferred embodiments, the moisture content of the slurry is typically from about 20 wt % to about 70 wt % or from about 30 wt % to about 60 wt %, preferably from about 35 wt % to about 55 wt % and, more preferably, from about 40 wt % to about 50 wt %.

Regardless of the manner of contact of the feedstock and acid (e.g., soaking, soaking followed by dewatering, or spraying), generally the acid-impregnated biomass slurry exhibits a solids content of at least about 0.25 g solids per g slurry. Typically, the acid-impregnated feedstock exhibits a solids content of at least about 0.30 g solids per g slurry and, more typically, at least about 0.35 g solids per g slurry. For example, in various embodiments, the acid impregnated biomass slurry exhibits a total solids content of from about 0.35 to about 0.65 g solids per g wet mixture, or from about 0.45 to about 0.55 g solids per g wet mixture.

10. Washing

In addition to impregnation of the feedstock to facilitate further treatment, acid impregnation may be utilized in a method that removes one or more impurities from the feedstock. For example, field-harvested feedstock may comprise one or more impurities (e.g., ash, sand, soil, rock, and tramp metals). In addition, contact of the feedstock and an acidic liquid medium may generate one or more impurities such as, for example, phenolic compounds derived from the lignin portion of the complex. These impurities may inhibit subsequent enzymatic hydrolysis of pretreated feedstock. Accordingly, in various preferred embodiments, acid-impregnated feedstock is subjected to a washing operation (not shown in FIG. 1) prior to further processing. More particularly, an aqueous liquid fraction may typically be removed from the acid-impregnated feedstock to form an acid-impregnated feedstock having a reduced content of one or more impurities.

Generally, washing of the feedstock may be conducted by counter-current contact of the feedstock and a liquid washing medium. Typically, the washing medium is an aqueous medium (e.g., process water) and the washing is conducted utilizing a suitable vessel or reactor known in the art.

The goal of washing is removal of impurities that may impact further processing. However, preferably the washing operation does not degrade the biomass feedstock fibers to a degree that substantially inhibits or prevents deriving fermentable sugars from the feedstock. Generally, the solid phase biomass comprises a fibrous solid phase that may be countercurrently contacted with the washing liquid in a mixing zone. In various preferred embodiments, the mixing zone comprises counter-rotating shafts (generally in parallel arrangement) having flights for agitation of the biomass. The conditions of countercurrent contact and agitation of the biomass are controlled to provide contact that increases the bioavailability of cellulose without excessive degradation of the fibers of the solid phase. For example, typically the washing does not degrade the fibers by more than 5%, more typically no more than about 3% and, still more typically, no more than about 2%, as measured by the average length of the fibers after the washing as compared to the average length of the fibers before washing.

Figure 2:
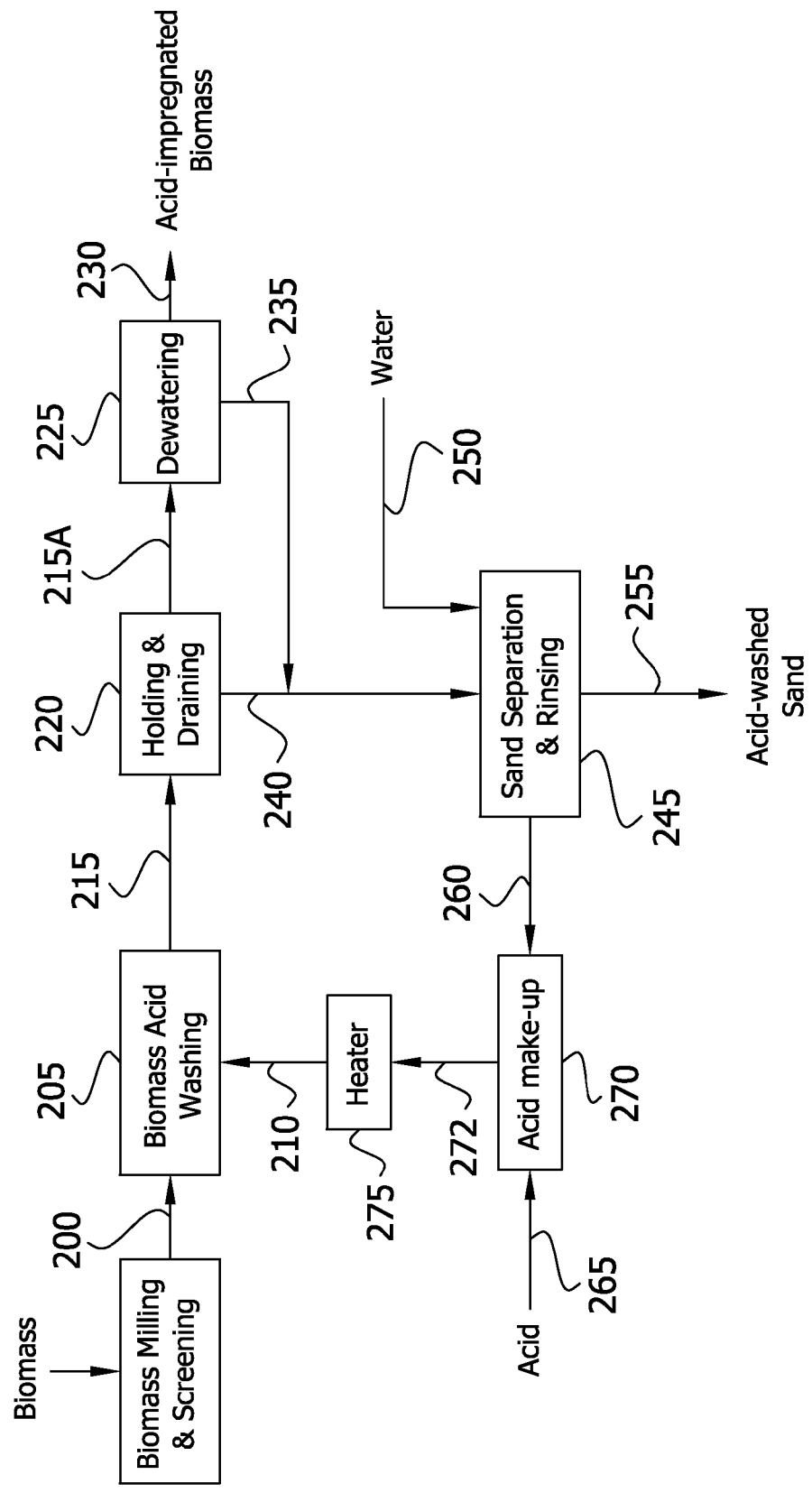
FIG. 2 depicts a pretreatment process of the present invention.

FIG. 2 depicts a method that combines washing and dilute acid impregnation of biomass. As shown in FIG. 2, milled and cleaned feedstock 200 (i.e., 21 shown in connection with the process of FIG. 1) is introduced into vessel 205 to which is also introduced acid stream 210. The milled/cleaned feedstock and acid are typically contacted within the vessel at a temperature of from about 20° C. to about 90° C. and, more typically, from about 30° C. to about 80° C. The contact time within vessel 205 is typically from about 0.1 to about 20 minutes and, more typically, from about 0.5 to about 10 minutes. Generally, the proportion of acidic liquid medium introduced into vessel 205 is suitable to provide a slurry in the vessel having a solids concentration in the vessel of from about 4 to about 10 wt %. To loosen impurities such as sand and soil from the feedstock, typically the slurry is agitated using a suitable agitator or mixer known in the art.

Again with reference to FIG. 2, acid-impregnated feedstock 215 is removed from vessel 205 and introduced into vessel 220 and held within the vessel for a time that promotes dispersion of acid throughout the particles of the acid-impregnated feedstock and to allow heavy contaminants such as gravel, sand, and metal to disengage from the feedstock fibers and settle to the bottom of the vessel. Generally, the acid-impregnated feedstock is held in vessel 220 for from about 1 to about 60 minutes, or from about 1 to about 30 minutes. The temperature of the feedstock within vessel 220 is typically from about 20° C. to about 90° C. and, more typically, from about 30° C. to about 80° C. As the solids content of the acid-impregnated feedstock decreases, solubilization of sugars may increase, which is undesired since this may reduce the ultimate fermentable sugar yield. If necessary, the solids content of the acid-impregnated feedstock may be controlled by controlling the amount of acid solution added to the feedstock and/or removal of excess acid solution using solid/liquid separators. Preferably, the solids content of the acid-impregnated biomass feedstock is from about 5 wt % to about 15 wt %, more preferably from about 5 to about 10 wt % and, still more preferably, from about 5 wt % to about 7 wt %.

Again with reference to FIG. 2, acid-impregnated feedstock 215A is introduced into a solids/liquid separator 225 comprising a draining screw conveyor, screen, filter, centrifuge, settler, dewatering screw press, or other solid/liquid separation instrumentality for removal of liquid (e.g., water). The manner of liquid removal is not narrowly critical and generally proceeds in accordance with suitable methods known in the art. Removal of liquid from the acid-impregnated feedstock provides acid-impregnated feedstock 230. It is to be understood that the acid-impregnated feedstock of the process of FIG. 1 (i.e., 33 in FIG. 1) may be prepared by the process depicted in FIG. 2. Contact of the feedstock and acid may proceed by soaking of the feedstock in an acidic liquid medium and/or spraying of the acidic liquid medium onto the feedstock, as detailed elsewhere herein. Acidic washing is generally believed to promote distribution of acid throughout the biomass particles while also removing a portion (preferably a significant portion) of the contaminants present in the feedstock (e.g., dirt, sand, and gravel). Removal of contaminants is advantageous as these may interfere or impact downstream processing by, for example, wear and/or damage to equipment utilized.

Again with reference to FIG. 2, dewatering acid-contacted feedstock 215A produces aqueous waste stream 235. In addition to promoting dispersion of the acid throughout the feedstock particles, holding acid-contacted feedstock 215 within vessel 220 allows for removal of impurities from the acid-washed feedstock and removal of water from the feedstock that could interfere with subsequent dewatering of the feedstock. In accordance with the process depicted in FIG. 2, vessel 220 is equipped with suitable apparatus (e.g., a screen) by or through which various fine particulate impurities are removed from the acid-washed feedstock. Further in accordance with the process of FIG. 2, impurities 240 are removed from vessel 220 and combined with aqueous waste stream 235 and introduced into another solid/liquid separator 245, e.g., a screen, filter, centrifuge, settler, hydrocyclone or flotation vessel. Also introduced into solid/liquid separator 245 is water stream 250. Separator 245 may be equipped for recovery of a variety of relatively fine impurities that have been separated from the acid-washed feedstock. The manner of recovery of fraction 255 from separator 245 is not narrowly critical and advantageously may be accomplished by incorporating a screen sized for recovery of the desired particles. In accordance with the process depicted in FIG. 2, impurities 255 are in the form of an sand-rich product (e.g., an acid-washed sand fraction). Recovery of fraction 255 from separator 245 yields a spent acid stream 260 in the form of an acidic aqueous liquid fraction. As shown in FIG. 2, spent acid stream 260 is recycled and combined with fresh acid 265 in vessel 270 to form a treatment acid stream 272 that is heated in vessel 275 to form heated treatment acid stream 210 that is contacted with the cleaned/milled feedstock. Although shown in FIG. 2, recovery of an impurity fraction (e.g., acid-washed sand) is not required. That is, the process of FIG. 2 may be utilized simply for the purpose of acid impregnation and removal of impurities from the feedstock as described above.

(i) Neutralization Capacity

Without being bound by theory, it is currently believed that during acid impregnation, typically only a portion of the acidic liquid medium contributes in any significant degree to preparation of the feedstock for enzymatic hydrolysis to produce fermentable sugars. Fine particulates of the biomass feedstock are generally high in inorganics components, including, for example, silica, calcium-containing components, magnesium-containing components, sodium-containing components, potassium-containing components, phosphorus-containing components, aluminum-containing components, and combinations thereof. These components of the biomass feedstock may neutralize the acid during acid impregnation. Consumption or neutralization of a significant fraction of the acidic liquid medium by the fine particulate fraction (e.g., as a result of the presence of alkaline compounds) is undesired as it generally does not provide acid impregnation that contributes in any significant degree to preparation of the feedstock for enzymatic hydrolysis to produce fermentable sugars. Various methods for cleaning the biomass feedstock detailed above (e.g., dry cleaning) remove a significant portion of the fine particulate fraction of the biomass feedstock, in particular, a fine particulate fraction rich in ash content.

The presence of components that may neutralize the acid during acid impregnation may be indicated by an acid neutralization capacity of the feedstock determined in accordance with methods known in the art. In particular, the acid neutralization capacity of biomass feedstocks and fractions removed and derived therefrom (e.g., fine particulate fractions and cleaned biomass feedstocks) may be determined in accordance with Protocol A as detailed in Example 8. Preferably in accordance with the present invention, the dry cleaning methods detailed herein provide cleaned biomass feedstocks having a lower acid neutralization capacity than achieved by other methods (e.g., water washing). For example, typically cleaned biomass feedstocks prepared in accordance with the present invention have an acid neutralization capacity as determined in accordance with Protocol A of less than about 0.01, more typically less than about 0.009 and still more typically, less than about 0.008, or less than about 0.007 (grams of acid/gram of dry biomass). In various embodiments, cleaned biomass feedstocks have an acid neutralization capacity of from about 0.0001 to about 0.01, from about 0.001 to about 0.01, from about 0.002 to about 0.01, from about 0.003 to about 0.01, from about 0.0001 to about 0.009, or from about 0.0001 to about 0.008.

Additionally or alternatively, an effective cleaning method may be indicated by a reduced acid neutralization capacity of the cleaned feedstock as compared to the starting biomass feedstock. For example, typically the acid neutralization capacity of the cleaned particulate biomass feedstock is no more than about 90% of the acid neutralization capacity of the starting feedstock, no more than about 85% of the acid neutralization of the starting feedstock, no more than about 80% of the acid neutralization capacity of the starting feedstock, no more than about 75%, no more than about 70%, no more than 65% no more than about 60%, no more than about 55%, no more than about 50%, or no more than about 45% of the acid neutralization capacity of the biomass feedstock. In various embodiments, the acid neutralization capacity of the cleaned particulate biomass feedstock is from about 10% to about 95%, from about 10% to about 90%, from about 10% to about 80%, from about 20% to about 95%, from about 20% to about 90%, from about 20% to about 80%, from about 30% to about 95%, from about 30% to about 90%, from about 30% to about 80%, from about 40% to about 95%, from about 40% to about 90%, from about 40% to about 80%, from about 50% to about 95%, from about 50% to about 90%, from about 50% to about 80%, from about 60% to about 95%, from about 60% to about 90%, from about 60% to about 80%, from about 70% to about 95%, from about 70% to about 90%, or from about 70% to about 80%, of the acid neutralization capacity of the biomass feedstock. Effective cleaning methods may be indicated by either or both these measures of acid neutralization capacity. That is, cleaned biomass feedstocks may exhibit an acid neutralization capacity within the above-noted limits and ranges and/or that exhibit a reduction in acid neutralization capacity as compared to the acid neutralization capacity of the starting feedstock.

Additionally or alternatively, effective cleaning methods may also be indicated by the acid neutralization capacity of the fine particulate fraction. For example, typically the fine particulate fraction has an acid neutralization capacity as determined in accordance with Protocol A of at least about 0.001, at least about 0.005, at least about 0.008, at least about 0.01, at least about 0.012, at least about 0.02, at least about 0.03, at least about 0.04, or at least about 0.05. Since a significant fraction of the neutralizing components of the ash of the feedstock are present in the fine particulate fraction, the relative acid neutralization capacities of fine particulate fraction and the cleaned biomass feedstock and/or starting biomass feedstock may also indicate an effective cleaning method. For example, typically the ratio of the acid neutralization capacity of the fine particulate to the acid neutralization capacity of the cleaned biomass feedstock is at least about 0.5:1, at least about 0.7:1, at least about 0.9:1, at least about 1.1:1, at least about 1.3:1, at least about 1.5:1, or at least about 2:1.

(ii) Acid Consumption

Effective cleaning methods of the present invention may also be indicated by the effectiveness of the acid consumed by the feedstock during acid impregnation. In particular, effective acid consumption may be indicated by the effectiveness of acid impregnation for deriving fermentable sugars (e.g., hemicellulose-derived sugars) and/or providing a feedstock that during subsequent enzymatic hydrolysis for the purpose of deriving fermentable sugars provides advantageous fermentable sugar yields. Derivation of xylose during pretreatment and providing a pretreated feedstock having a cellulose digestibility effective for subsequent enzymatic hydrolysis may be determined in accordance with methods known in the art including, for example, as described in Examples 10 and 11, respectively. For example, effective cleaning methods may be indicated by either or both of these measures in combination with use of a relatively low proportion of acid during acid impregnation. That is, since the feedstock has been cleaned and a significant fraction of the feedstock that consumes the acid but does not contribute to effective acid impregnation has been removed, lower amounts of acid (e.g., a relatively proportion of acid diluted in a liquid medium to the total proportion of biomass feedstock solids) may be utilized during acid impregnation that nonetheless provide effective acid impregnation.

For example, in accordance with various preferred embodiments, the weight ratio of acid (i.e., mass of acid) to solids fraction of the cleaned particulate biomass feedstock introduced into the acid impregnation zone is less than about 0.1:1, less than about 0.05:1, less than about 0.045:1, less than about 0.04:1, less than about 0.035:1, less than about 0.03:1, less than about 0.025:1 (e.g., less than about 0.02:1 or less than about 0.01:1).

In various embodiments, the weight ratio of acid to solids fraction of the cleaned particulate biomass feedstock introduced into the acid impregnation zone is from about 0.01:1 to about 0.05:1, from about 0.01:1 to about 0.045:1, from about 0.01:1 to about 0.04:1, from about 0.02:1 to about 0.04:1, from about 0.02:1 to about 0.04:1, from about 0.01:1 about 0.035:1, from about 0.02:1 to about 0.035:1, from about 0.01:1 to about 0.03:1, from about 0.02:1 to about 0.03:1, from about 0.01:1 to about 0.025:1, or from about 0.01:1 to about 0.02:1. Advantageously, as determined in accordance with Protocol B as described in Example 10, the xylose content of the liquid fraction of a pretreated biomass feedstock represents a xylose yield of at least about 70%, at least about 75%, at least about 80%, at least about 85%, or at least about 90% (based hemicellulose content of the particulate biomass feedstock). In these and other embodiments, the liquid fraction of the pretreated biomass feedstock prepared from the acid-impregnated feedstock has a xylose content representing a xylose yield of from about 70% to about 95%, from about 70% to about 90%, from about 70% to about 85%, from about 75% to about 95%, from about 75% to about 90%, from about 75% to about 85%, from about 80% to about 95%, from about 80% to about 95% or from about 85% to about 95% (based hemicellulose content of the particulate biomass feedstock).

Additionally or alternatively, acid impregnated feedstocks provided by a relatively low proportion of acid to biomass solids (e.g., a ratio of less than about 0.01:1) may be utilized in a process that provides a cellulose-containing solids fraction indicating advantageous cellulose digestibility and thus a pretreated feedstock suitable for effective enzymatic hydrolysis. For example, in various preferred embodiments, the cellulose digestibility of the pretreated biomass feedstock, as determined in accordance with Protocol C as described in Example 11, is at least about 60%, at least about 70%, at least about 80%, or at least about 90%. Typically, the cellulose-derived fermentable sugar content of the cellulose hydrolyzate slurry represents a yield of from about 60% to about 95%, from about 60% to about 90% from about 70% to about 95%; from about 70% to about 90%, from about 80% to about 95%, from about 80% to about 90%, from about 85% to about 95%, or from about 90% to about 95%.

Effective acid impregnation in combination with the dry cleaning methods may be provided under various combinations of amount of acid utilized, amount of acidic liquid medium utilized, solids content of the biomass feedstock, etc.

The acid content of the acidic liquid medium is not narrowly critical and the desired amount of acid contacted with the cellulosic biomass feedstock may be controlled by the total amount of acidic liquid medium contacted with the biomass feedstock. For example, at higher acid concentrations, less acidic liquid medium may be utilized. However, generally the acidic liquid medium contacted with the biomass feedstock has an acid concentration of less than about 5 wt %, less than about 4 wt %, less than about 3 wt %, less than about 2 wt %, less than about 1 wt %, less than about 0.75 wt %, or less than about 0.5 wt %. Typically, the acidic liquid medium has an acid concentration from about 0.1 wt % to about 4 wt %, from about 0.1 wt % to about 3 wt %, from about 0.2 wt % to about 4.5 wt %, from about 0.5 wt % to about 2 wt %, or from about 0.5 wt % to about 1 wt %, from about 0.7 wt % to about 3.5 wt %, from about 0.5 wt % to about 3 wt %, from about 1.0 wt % to about 3.0 wt %, or from about 2.0 wt % to about 2.5 wt %.

Generally, the cellulosic biomass feedstock and acidic liquid medium are contacted at a temperature of at least about 75° C., at least about 100° C., at least about 125° C., at least about 150° C., at least about 175° C. or at least about 200° C. Typically, the cellulosic biomass feedstock and acidic liquid medium are contacted at a temperature of from about 100° C. to about 200° C. and more typically from about 125° C. to about 175° C.

Although not narrowly critical and generally selected to provide suitable acid uptake, generally the biomass feedstock and acidic liquid medium are generally contacted for a time of at least about 1 minute, at least about 2 minutes, at least about 3 minutes, at least about 5 minutes, at least about 10 minutes, or at least about 15 minutes. Typically, the biomass feedstock and acidic liquid medium are contacted for a time of from about 1 minute to about 120 minutes, from about 1 minute to about 60 minutes, from about 2 minutes to about 30 minutes, from about 5 minutes to about 30 minutes, or from about 10 minutes to about 20 minutes.

Further in accordance with these and various other embodiments, utilizing a relatively low proportion of acid may represent utilizing a relatively low proportion of acidic liquid medium. Thus, typically the acid-impregnated biomass feedstock has a total solids content greater than typically provided by various conventional methods that include soaking of the biomass feedstock in a large amount of acidic liquid medium. Generally, the total solids content of the acid-impregnated feedstock is at least about 25 wt %, at least about 30 wt %, at least about 40 wt %, or at least about 50 wt %, at least about 60 wt %, at least about 70 wt %, and at least about 80 wt %. Typically, the total solids content of the acid-impregnated biomass feedstock is from about 25 wt % to about 90 wt %, from about 25 wt % to about 80 wt %, from about 30 wt % to about 90 wt %, from about 30 wt % to about 80 wt %, from about 40 wt % to about 90 wt %, from about 40 wt % to about 80 wt %, from about 50 wt % to about 90 wt %, from about 50 wt % to about 80 wt %, from about 60 wt % to about 90 wt %, or from about 60 wt % to about 80 wt %.

Advantageously, suitable acid uptake is achieved for high solids biomass feedstocks while utilizing relatively dilute acids. For example, typically the acid concentration of the acidic liquid medium is less than about 4 wt %, less than about 3 wt %, or less than about 2 wt %. Additionally or alternatively, suitable acid uptake may be achieved by contacting relatively low proportions of dilute acidic liquid media. For example, the weight ratio of acidic liquid medium to solids content of the biomass feedstock contacted in the acid-impregnation vessel is no more than about 3:1, no more than about 2:1, no more than about 1:1, or no more that about 0.5:1. In various embodiments, the weight ratio of acidic liquid medium to solids content of the biomass feedstock contacted in the acid-impregnation vessel is from about 0.5:1 to about 4:1, from about 0.5:1 to about 3:1, from 1:1 to about 3:1, from about 0.5:1 to about 2:1. Accordingly, in various embodiments, the weight ratio of acidic liquid medium to solids content of the biomass feedstock introduced into the acid-impregnation zone is no more than about 1.1:1 and the acidic liquid medium has an acid concentration of less than about 4 wt %.

Generally, these embodiments provide an acid-impregnated feedstock having a relatively high solids content and a relatively low acid concentration. For example, in various embodiments, the solids content of the acid-impregnated feedstock is at least about 25 wt % and the acid concentration of the acid-impregnated feedstock is less than about 4 wt %.

In various embodiments, an acid-impregnated biomass feedstock having a total solids content of at least 20 wt % is formed by contacting a biomass feedstock having a total solids content of at least about 80 wt % with an acidic liquid medium having an acid concentration of less than about 4 wt % in an acid-impregnation zone, wherein the weight ratio of acid to solids of the biomass feedstock is no more than about 0.04:1.

B. Steam Treatment

Pretreatment of cellulosic biomass feedstock typically comprises subjecting the acid-impregnated feedstock to conditions comprising elevated temperature and pressure to break down the cellulose-hemicellulose-lignin complex. Generally, and again with reference to FIG. 1, acid-impregnated feedstock 33 is subjected to elevated steam pressure and temperature in the presence of $H_2O$ (e.g., steam) in a suitable reactor, or vessel 37 as shown in FIG. 1. After a period of contact with $H_2O$ under the elevated steam pressure and temperature conditions, the pretreated feedstock is discharged to an environment of reduced pressure. The abrupt change in pressure breaks down the biomass fiber structure including, for example, the cellulose-hemicellulose-lignin complex (e.g., breaks bonds between lignin and hemicellulose and/or cellulose).

Steam treatment typically dissociates cellulose from the hemicellulose and lignin and, thus, provides cellulose available for enzymatic hydrolysis to produce fermentable sugars. Steam treatment also typically dissociates hemicellulose from the complex, generally in the form of hemicellulose solubilized within a liquid phase of the treated feedstock. For example, in various embodiments, at least about 60 wt %, at least about 70 wt %, at least about 80 wt %, or up to 90 wt % of the hemicellulose is solubilized within a liquid phase of the treated feedstock. In this manner, steam treatment provides hemicellulose available for hydrolysis to produce fermentable sugars. As described herein, treatment of acid-impregnated feedstock at elevated temperature and pressure generally corresponds to treatment known in the art commonly referred to as "steam explosion." Steam explosion methods are generally described in, for example, U.S. Pat. No. 1,824, 221, U.S. Pat. No. 4,461,648, and Canadian Patent No. 1 096 374, the entire contents of which are incorporated herein by reference for all relevant purposes.

As shown in FIG. 1, acid-impregnated feedstock 33 is generally introduced into a vessel 37 comprising a contact zone for steam treatment. The acid-impregnated feedstock is typically in the form of a slurry, or cake. For example, an acid-impregnated slurry may be pressed to form a cake, or plug of pretreated solids for introduction into the steam treatment vessel. The precise form and configuration of the vessel is not narrowly critical and may be selected by one skilled in the art depending on the particular circumstances (e.g., properties of the feedstock and operating conditions). Generally, the vessel includes an inlet for introduction of the feedstock and one or more outlets, or exits for releasing treated feedstock and/or various components generated during the steam treatment. Once the feedstock is contained in the vessel, the vessel is pressurized and the feedstock heated. Typically, the feedstock is maintained at a target temperature for a time sufficient to provide suitable heating of the feedstock. After a period of pressurizing the vessel and heating the feedstock, the feedstock is released from the vessel, or contact zone. As noted, the abrupt decrease in pressure during this release promotes break down of the cellulose-hemicellulose-lignin complex. That is, the abrupt decrease in pressure causes an explosive effect by virtue of a rapid increase in volume of the steam and gases trapped inside the biomass pore structure that causes high instantaneous incident gas velocities and/or instant vaporization of heated water that has either occupied or been forced into the fiber structure so that it becomes literally explosive when it expands.

Generally, the proportion of steam utilized depends on the initial moisture content, temperature, and/or void volume of the feedstock. Typically, the ratio of the total mass of $H_2O$ (i.e., steam) to acid-impregnated corn stover introduced into the vessel and/or contact zone is at least about 0.1:1, more typically at least about 0.15:1 and, still more typically, at least about 0.2:1. For example, in various preferred embodiments, the mass ratio of $H_2O$ to acid-impregnated feedstock is from about 0.1:1 to about 0.5:1 and, more preferably, from about 0.2:1 to about 0.4:1, resulting in condensation of superatmospheric water vapor which intermingles with and penetrates the fiber.

1. Pressure

Generally, and in accordance with the process depicted in FIG. 1, steam (typically saturated) 39 is introduced into vessel 37 under a pressure of at least about 75 psig, at least about 125 psig, or at least about 150 psig. Typically, acid-impregnated feedstock and $H_2O$ are contacted within the vessel (e.g., within a contact zone comprising an inlet comprising a receiving zone for pretreated feedstock and an outlet for removal of feedstock from the contact zone) under a pressure of from about 75 to about 250 psig, more typically from about 90 to about 210 psig and, still more typically, from about 150 to about 200 psig. Additionally or alternatively, the acid-impregnated feedstock and $H_2O$ are typically contacted within a contact zone comprising a vapor phase in which the partial pressure of water is at least about 55 psig. Typically, the partial pressure of water vapor in the contact zone is at least about 150 psig and, more typically, at least about 175 psig.

2. Pressure Change

As noted, the abrupt change in pressure provided by withdrawing, or removing pretreated feedstock from a contact zone into a receiving zone or vessel of reduced pressure degrades the lignin-hemicellulose-cellulose complex. Typically, the pretreated biomass feedstock is released from the contact zone to an environment of atmospheric pressure. Pressure changes associated with such treatment may typically be at least about 100, at least about 120, or at least about 150 psig. Releasing pretreated feedstock from the contact zone in this manner may be utilized in suitable pretreatment, but may raise one or more issues. For example, abrupt pressure changes to atmospheric pressure may release one or more volatile components (e.g., acetic acid, furfural, and hydroxymethyl furfural) and may promote fiber degradation. Optionally, the volatile components may be removed and recovered during, for example, water washing, lignin extraction, hydrolysis, and/or fermentation. Accordingly, in various preferred embodiments, pretreated feedstock is removed from the contact zone into a suitable receiving zone or vessel comprising an inlet at which the pressure is above atmospheric pressure. More particularly, in various preferred embodiments, to maintain adequate and preferably rapid depressurization to provide effective degradation of the fiber structure and release of one or more volatile components, the pressure at the outlet, or exit of the steam contact zone and the inlet of the receiving zone typically differs by less than about 100 psig, more typically less than about 75 psig and, still more typically, less than about 50 psig.

Generally, as the pressure within the contact zone increases, degradation of feedstock fibers increases upon release of pressure. Degraded fibers may introduce issues in subsequent processing. For example, degraded fibers may be more difficult to filter after subsequent washing. Thus, in various preferred embodiments, the pressure within the contact zone is controlled to preferably avoid substantial degradation of the feedstock fibers.

At a given partial pressure of water vapor, total pressure in the contact zone may increase based on the presence of non-condensable components of the feedstock (e.g., air). Thus, in various preferred embodiments, as shown in FIG. 1, the pressure within the contact zone may be controlled by release of at least a portion of a vapor phase present within the contact zone of steam treatment vessel 37 in the form of a flash steam 41. Generally, the mass ratio of flash stream removed from the pretreatment vessel to the total proportion of steam introduced into the vessel is at least about 0.1:1, at least about 0.15:1, or at least about 0.20:1. Typically, the mass ratio of flash steam 41 removed from the vessel to the steam introduced thereto is from about 0.15:1 to about 0.5:1 and, more typically, from about 0.2:1 to about 0.4:1.

3. Temperature

The temperature of steam introduced into the vessel and/or the temperature within the vessel and/or contact zone is typically from about 160° C. to about 220° C., more typically from about 170° C. to about 210° C. and, still more typically, from about 180° C. to about 200° C.

In various preferred embodiments, distribution of the moisture (e.g., water vapor of steam treatment) throughout the acid-impregnated feedstock is generally uniform and, more preferably, substantially uniform. Uniform moisture distribution is currently believed to promote relatively uniform temperature throughout the contact zone and relatively uniform temperature of the feedstock. Thus, typically the feedstock is brought to a target temperature within the contact zone by distribution of steam throughout the feedstock such that the average temperature of a significant portion of the feedstock does not vary from a target temperature to any significant degree. For example, in various preferred embodiments, the average temperature of a region of the biomass feedstock (e.g., a portion of the feedstock constituting at least about 5% by weight, at least about 25% by weight, or at least about 50% by weight of the feedstock) does not differ by more than 5° C. from the target temperature. By way of further example, the average temperature of a region of the biomass constituting at least about 60% by weight, or at least about 75% by weight of the feedstock does not differ by more than 5° C. or no more than 3° C. from the target temperature. To promote even temperature distribution throughout the vessel and/or contact zone, various controls are utilized. For example, preferably the total solids content of the feedstock introduced into the vessel and/or contact zone is maintained at from about 30 wt % to about 70 wt % (e.g., from about 40 wt % to about 60 wt %). Having a feedstock of total solids content within this range promotes even heating of the acid-impregnated feedstock by direct steam injection as higher moisture content feedstocks can result in formation of a large amount of condensate on the feedstock that hinders steam penetration and heat transfer throughout the feedstock. If necessary, the feedstock may be dewatered by removing excess acidic liquid medium using a mechanical solid/liquid separation device such as a dewatering screw press. Plug screw feeders commonly used in connection with pretreatment digesters (e.g., continuous pretreatment digesters) may be utilized as the dewatering device. In addition, multiple steam nozzles may be utilized to promote relatively quick injection of steam into the pretreatment vessel. For example, in connection with batch pretreatment digesters preferably multiple steam nozzles are placed at lower portions of the digester and others are placed at the height of the reactor such that when the valves are opened initially there will be direct contact between steam and feedstock mass settled in the vessel. It is currently believed that venting of non-condensable gases contributes to maintaining the vapor temperature near the temperature of the input steam, thereby contributing to even temperature distribution throughout the biomass feedstock.

The temperature within the pretreatment vessel may also be controlled to contribute to venting of one or more volatile components generated during the abrupt pressure changes of the acid-impregnated feedstock to atmospheric pressure. For example, furfural has been reported to remain volatile and therefore able to be removed by venting at temperatures in excess of 110° C. (e.g., greater than about 120° C.). Thus, in various preferred embodiments the temperature of the steam treatment vessel is maintained above this level to promote venting of furfural and noncondensable gas.

4. Residence Time

As the residence time of the acid-impregnated feedstock in the vessel for steam treatment increases, degradation of cellulose and/or hemicellulose to undesired products may be observed. For example, in the case of cellulose, degradation products such as hydroxymethyl furfural may be formed during periods of prolonged treatment. Accordingly, the residence time within the reactor is typically selected to provide an increase in cellulose bioavailability and/or solubilizing hemicellulose without resulting in product degradation.

Generally, the acid-impregnated feedstock and $H_2O$ (i.e., steam) are contacted for between about 1 and about 60 minutes, more generally between about 1 and about 30 minutes and, still more generally, between about 1 and about 20 minutes. Typically, the acid-impregnated feedstock and $H_2O$ are contacted for between about 1 and about 10 minutes, more typically between about 2 and about 6 minutes and, still more typically, between about 3 and about 5 minutes.

5. Particle Size

In addition to impacting acid impregnation, the size of the particulate solids may impact the effectiveness of steam pretreatment. For example, as particle size increases, the bulk density of biomass solids to be treated tends to decrease. Accordingly, the payload and/or cost effectiveness of the steam pretreatment operation may suffer. In addition, an increase in solids particle size and the concomitant decrease in exposed solids surface area may negatively impact distribution of the acid present in the acid-impregnated feedstock, and likewise hinder distribution of steam throughout the acid impregnated feedstock. Additionally or alternatively, it is currently believed that as the size of particulates that make up the biomass generally decreases, the void fraction throughout the acid-impregnated biomass feedstock generally increases, which promotes distribution of the stream throughout the feedstock particles. Thus, acid-pretreated feedstock containing a significant fraction of particles within the above-noted preferred particle size ranges provides advantages during subsequent steam treatment. While the void fraction throughout the feedstock particles generally promotes distribution of steam throughout, it is currently believed that an uneven distribution of the void fraction may provide relatively large portions of void fraction that effectively trap a portion of the steam introduced into the reactor and that the steam trapped throughout this void fraction does not contribute to any significant degree to pretreatment of the biomass. It is currently believed that uneven distribution of the void fraction may occur in connection with feedstock comprising a significant fraction of relatively large particles or a significant fraction of relatively small particles. Accordingly, acid-pretreated feedstock likewise preferably contains a significant fraction of particles within the above-noted preferred particle size ranges to preferably avoid an excessively uneven distribution of void fraction.

In addition, steam treatment of the acid-impregnated feedstock typically reduces the size of the particulate solids of the acid-impregnated feedstock. During subsequent hydrolysis (e.g., enzymatic hydrolysis of cellulose using a cellulase enzyme), particulate solids of reduced size may provide an increase in exposed surface area of cellulose and/or hemicellulose that would otherwise be provided by the particulate solids of the feedstock prior to steam treatment.

6. Equipment

The form of the vessel, or reactor utilized for steam treatment is not narrowly critical and may be selected by one skilled in the art depending on the intended process conditions. Steam treatment may be practiced on a batch or continuous basis. For example, in the case of batch operations, the vessel may be in the form of a stirred or non-stirred tank reactor. In the case of continuous steam treatment operations, the vessel may be in the form of a continuous horizontal screw-fed mixer or a vertical vessel. Continuous operation may provide one or more advantages including, for example, avoiding the need to de-pressurize and re-pressurize the contact zone between batches, which result in the requirement of larger reactor volumes. Generally, acid-impregnated feedstock is introduced into the steam treatment vessel using conventional apparatus known in the art including, for example, a feeder such as a plug screw feeder.

7. Two-Stage Pretreatment

Further in accordance with the present invention and, more particularly, the process depicted in FIG. 1, the conditions of elevated temperature and pressure to which the acid-impregnated feedstock is subjected may be controlled to promote advantageous dispersion of acid throughout the feedstock. More particularly, the elevated temperature and pressure conditions may comprise a plurality of intervals, or stages of varying conditions and, in various preferred embodiments, include two stages of differing temperature and pressure. For example, in various preferred embodiments, acid-impregnated feedstock and steam (i.e., $H_2O$) are contacted within a suitable vessel as described above under a first set of conditions (i.e., an "initial steaming period") for purposes of breakdown of the cellulose-hemicellulose-lignin complex and hydrolysis of xylan. This first set of conditions is generally within the range of pretreatment conditions provided elsewhere herein and typically provides rapid heating of the acid-impregnated feedstock. More particularly, in accordance with various preferred embodiments, the temperature of the steam treatment vessel is typically maintained at from about 150° C. to about 240° C. and, more typically, at from about 160° C. to about 230° C. Typically, the acid-impregnated feedstock is subjected to a saturated steam pressure of from about 55 to about 470 psig and, more typically, from about 75 to about 380 psig during this initial period. To provide a vessel or contact zone under these conditions, typically steam under a pressure of at least about 75 psig, or at least about 100 psig is introduced into the vessel while air is purged from the vessel by, for example, venting of the vessel. After purging of air from the vessel is complete, any outlets of the vessel are closed and introduction of the pressurized steam into the vessel continues to achieve the desired conditions. In various embodiments (e.g., when the pretreated feedstock is subjected to relatively low) the contact time of acid-impregnated feedstock and steam under the first set of conditions including additional steam introduction and purging of the vessel is typically from about 1 to about 45 minutes and, more typically, from about 1 to about 30 minutes.

For batch pretreatment, once the first stage of steam treatment is completed, introduction of pressurized steam to the vessel is discontinued and the pressure within the vessel, or contact zone is reduced, and the second-stage of pretreatment is conducted at reduced pressure and temperature before the contents of the pretreatment vessel are explosively discharged into a collection vessel upon completion of the second stage of pretreatment. For continuous pretreatment, once the first stage of steam pretreatment is completed, the partially pretreated feedstock is transferred into a second-stage vessel in which the partially pretreated feedstock is subjected to reduced pressure/temperature conditions. Regardless of whether pretreatment is conducted as a batch or continuous process, upon completion of the second-stage of pretreatment, the pretreated feedstock is explosively discharged into a collection vessel. Generally, the pressure within the collection vessel is maintained at slightly above atmospheric pressure to prevent ingestion of contaminants from outside the vessel under ambient pressure by opening one or more outlets, or vents of the vessel, or by quenching the flash steam with water spray, or by a combination of venting and water spray. Typically, during the second stage of pretreatment conditions, the pressure within the vessel, or contact zone represents a reduction in pressure of at least about 30 psig and, more typically, at least about 50 psig (e.g., about 75 psig or greater) as compared to the pressure within the vessel or contact zone during the first stage. For example, preferably the saturated steam pressure within the vessel or contact zone during the second stage is from about 25 psig to about 150 psig and, more preferably, from about 50 psig to about 100 psig. Additionally or alternatively, the temperature within the vessel or contact zone of the second stage is preferably from about 130 to about 185° C. and, more preferably, from about 145 to about 170° C. The purpose of the second stage (i.e., venting the steam or cooling the pretreated feedstock by adding lower temperature water or other liquids or solutions) is further hydrolysis of xylan. This stage is typically conducted over a period of from about 0.1 to about 5 minutes and, more typically, conducted over a period of from about 0.3 to about 3 minutes. Once the second stage is complete, pretreated feedstock is expelled from the vessel (i.e., as described above and in connection with the process depicted in FIG. 1.).

Regardless of batch or continuous operation, the primary purpose of the second lower temperature and pressure stage of pretreatment is hydrolysis of oligomeric sugars generated during the first stage of pretreatment. During batch two-stage pretreatment, the period of venting or pressure reduction of the vessel releases volatiles such as furfural, hydroxymethyl furfural and acetic acid.

Two-stage pretreatment in accordance with the present invention may also be conducted by the following method. In the first stage, acid-impregnated feedstock is subjected to conditions within a contact zone effective for solubilizing hemicellulose and producing a stream treated feedstock. In particular, the conditions within the first stage are effective for providing a liquid fraction within the first stage, or contact zone comprising xylose. Generally, acid-impregnated feedstock is contacted with saturated steam at pressures ranging from about 75 psig to about 250 psig or from about 100 psig to about 200 psig. Typically in the first stage, the acid-impregnated feedstock is contacted with saturated steam at a pressure of from about 140 psig to about 170 psig. The temperatures to which the acid-impregnated feedstock are subjected in the first stage of pretreatment are generally from about 140° C. to about 230° C. or from about 160° C. to about 200° C. Generally, the first stage of elevated temperature/ pressure conditions is conducted for from about 1 to about 15 minutes, and typically for from about 2 to about 10 minutes.

During the first stage of pretreatment, non-condensable vapor components (e.g., air entrained in the acid-impregnated feedstock) and volatile components generated during the steam treatment (e.g., acetic acid and furfural) may be continuously removed from the vessel by venting of the vessel combined with introduction of fresh steam to maintain the pressure within the vessel substantially constant. Generally, the vent nozzles are located to provide venting of vapor components without venting of feedstock fibers.

Upon completion of the first stage of pretreatment, the steam treated feedstock is then subjected to further conditions in a second zone effective for additional solubilizing of hemicellulose, hydrolyzing of oligosaccharides, and producing a volatilized fraction of the steam treated feedstock. The pressures to which the steam treated feedstock is subjected in this second zone are lower than the pressure within the contact zone of the first stage. For example, typically the steam treated feedstock is subjected to pressures of from about 5 to about 50 psig, from about 5 psig to about 40 psig, or from about 10 to about 15 psig during this second stage of pretreatment. In this manner, the second stage of pretreatment may be described as conducted in a depressurization zone. The pressures during the second stage and within the depressurization zone generally correspond to temperatures of from about 110° C. to about 150° C., more typically from about 110° C. to about 140° C. (e.g., from about 110° C. to about 120° C.).

In accordance with the two-stage method of pretreatment, a volatilized fraction of the steam treated feedstock is removed from the depressurization zone. The volatilized fraction generally comprises furfural, acetic acid, steam, or a combination thereof. Releasing the volatilized fraction controls the pressure and temperature within the depressurization zone. Release of the volatilized fraction and pressure/temperature control may be conducted using a pressure control valve or damper on the exhaust gas line.

The conditions within the depressurization zone are effective for solubilizing hemicellulose and, thus, provide a liquid fraction within the depressurization zone containing xylose. The conditions within the depressurization zone are controlled to provide continued solubilization of hemicellulose, but without excessive degradation of cellulose and sugars. Typically, the conditions of the depressurization zone are controlled to provide a xylose content of the liquid fraction that represents a xylose yield of at least about 60%, at least about 70%, or at least about 80% based on the hemicellulose content of the cellulosic biomass feedstock. Additionally or alternatively, the conditions of the depressurization zone provide a xylose content of the liquid fraction in the depressurization zone that is typically at least 5%, 10%, 20%, or 30% higher than the xylose content of the liquid fraction in the contact zone.

Temperature control within the depressurization zone allows for venting of volatile components such as, for example, steam, acetic acid, and furfural. Venting of furfural in the vapor phase avoids reaction of furfural in the liquid phase with sugars and/or formation of inhibitors of enzymatic hydrolysis. Thus, preferably the conditions within the depressurization zone maintain furfural in the vapor phase. Since furfural is known to exist in the vapor phase at temperatures in excess of 110° C., preferably the conditions within the second stage vessel maintain the temperature above 110° C. to allow for venting of the furfural volatile component. Although preferably maintained above 110° C. to maintain the furfural component in a volatile state, temperatures at or within the lower of the above-noted ranges (e.g., from about 110° C. to about 115° C.) are often preferred in order to maximize the temperature difference between the fibers and feedstock and the heat absorbing liquid, which may serve to increase the rate at which the fibers are cooled.

Advantageously, the control of pressure and temperature within the depressurization may be conducted only through releasing of a portion of the volatilized fraction and preferably is conducted only through releasing a portion of the volatilized fraction. That is, the two-stage pretreatment method of the present invention does not utilize any additional liquid media for temperature control and/or pH adjustment.

This two-stage pretreatment is preferably conducted in a continuous manner. That is, preferably the acid impregnated feedstock is continuously subjected to the above-noted conditions within a contact zone for the first stage of pretreatment while steam treated feedstock provided by the first stage of pretreatment is continuously subjected to the above-noted conditions within the depressurization zone and a volatilized fraction is released from the depressurization zone. The two-stage process may utilize a single or multiple vessels. That is, in various embodiments the contact zone for the first stage of pretreatment and the depressurization zone for the second stage of pretreatment are contained in a single vessel. In various other embodiments, the contact zone and depressurization zone are contained in separate vessels. For example, in various embodiments the first stage is conducted in a vertical or horizontal pretreatment digester and the second stage is conducted in a suitable vessel such as, for example, a blow tank.

Upon completion of the second stage of pretreatment, the feedstock is continuously discharged from the vessel (e.g., utilizing a screw conveyor feeding a blow valve) and introduced into the vessel for the second stage of pretreatment. The second step of steam treatment is conducted in a suitable vessel such as, for example, a blow tank.

Utilizing a high pressure blow tank is currently believed to provide additional hydrolysis of xylan to xylose and dissipation of heat from the fibers. In addition, generally there is a period of time after discharge of pretreated feedstock from the reactor before the temperatures of the solid and liquid fractions reach equilibrium. Typically, the solids fraction is cooled as heat is transferred by convection and/or conduction to the liquid fraction. Thus, as the solids fraction is cooled, the liquid fraction is heated. During high pressure discharge, a significant fraction, and preferably substantially all the heat is released from the liquid fraction by evaporation and therefore as heat is transferred from the solids to liquid fraction the heat recovered by the liquid fraction is release through this evaporation. After a suitable period to time, the pretreated material is then subjected to further treatment including, for example, conditioning as detailed elsewhere herein.

C. Pretreated Feedstock

Again with reference to FIG. 1, pretreated feedstock 45 is in the form of a mixture comprising feedstock fibers and including a solids fraction and a liquid fraction. Typically, the pretreated feedstock is in the form of a slurry comprising insoluble fibers, water, and soluble materials and having a moisture content of from about 40 wt % to about 80 wt %, more typically from about 50 wt % to about 70 wt %. The temperature of the pretreated feedstock exiting the steam treatment zone is not narrowly critical, but is typically from about 80° C. to about 120° C. and, more typically, from about 90° C. to about 110° C. The pH of the pretreated feedstock is typically less than about 4, less than about 3.5, or less than about 3 (e.g., from about 1 to about 2.5).

1. Solids Fraction

The water-insoluble solids fraction of the pretreated feedstock generally comprises those solids of the acid-impregnated feedstock that are not solubilized during acid and steam treatment. The solids fraction of the pretreated feedstock generally comprises cellulose, unsolubilized lignin, unsolubilized hemicellulose, and unsolubilized ash, and generally constitutes at least about 30 wt %, at least about 40 wt %, or at least about 50 wt % of the pretreated feedstock. For example, typically the water-insoluble solids fraction constitutes from about 40 wt % to about 80 wt % of the pretreated feedstock, more typically from about 50 wt % to about 75 wt % and, still more typically, from about 60 wt % to about 75 wt % of the pretreated feedstock. The composition of the solids fraction of the pretreated feedstock generally corresponds to the composition of the acid-impregnated feedstock, adjusted for break-down of the cellulose-hemicellulose-lignin complex. For example, in various embodiments at least about 10%, at least about 20%, at least about 30%, or at least about 40% of the polysaccharide content of the pretreated feedstock is solubilized and can be found in the liquid fraction of the pretreated feedstock.

Generally, cellulose constitutes at least about 30 wt %, at least about 40 wt %, or at least about 50 wt % of the water-insoluble solids fraction. Typically, cellulose constitutes from about 35 wt % to about 65 wt %, more typically from about 40 wt % to about 60 wt % and, still more typically, from about 45 wt % to about 55 wt % of the solids fraction. Cellulose contents of the solids of the pretreated feedstock may be determined by conventional means known to one skilled in the art including, for example, concentrated acid hydrolysis of cellulose to glucose and determining the glucose released by High Performance Liquid Chromatography (HPLC).

One indicator of effective pretreatment (i.e., effective break down of the cellulose-hemicellulose-lignin complex to provide cellulose available for preparation of fermentable sugars) is a solids fraction that includes a significant fraction of the initial cellulose content of the feedstock. Accordingly, additionally or alternatively, in various preferred embodiments the pretreated feedstock solids fraction typically comprises at least about 40 wt %, more typically at least about 45 wt % and, still more typically, at least about 50 wt % of the initial cellulose content of the feedstock. As detailed in the working examples and mass balances provided herein, such recoveries of cellulose in pretreated feedstocks may be provided by a variety of combinations of pretreatment parameters.

The water-insoluble solids fraction also typically comprises lignin. For example, typically lignin constitutes at least about 20 wt %, at least about 25 wt %, or at least about 30 wt % of the water-insoluble solids fraction. Additionally or alternatively, the water-insoluble solids fraction of the pretreated feedstock typically comprises up to about 75 wt % or up to about 95 wt % of the initial lignin content of the feedstock.

As detailed below, pretreatment generally solubilizes a significant fraction of hemicellulose, but a fraction of hemicellulose may be present in the water-insoluble solids fraction of the pretreated feedstock. For example, hemicellulose may constitute up to about 4 wt %, up to about 6 wt %, or up to about 8 wt % of the water-insoluble solids fraction. More particularly, up to about 6 wt %, up to about 10 wt %, up to about 20 wt %, or up to about 25 wt % of the initial hemicellulose content of the feedstock may be present in the water-insoluble solids fraction of the pretreated feedstock.

2. Liquid Fraction

The liquid fraction of the pretreated feedstock typically comprises solubilized hemicellulose, solubilized cellulose, and solubilized components provided by degradation of lignin. Pretreatment preferably increases the bioavailability of the feedstock which may be indicated by, for example, degradation of the cellulose-hemicellulose-lignin complex and/or break down of cellulose and/or hemicellulose into fermentable sugars. For example, in accordance with the process depicted in FIG. 1, lignin and/or various soluble fermentable sugars are typically present in the liquid fraction of the pretreated feedstock. More particularly, fermentable sugars (e.g., glucose, xylose, arabinose, mannose, galactose, and various oligomers thereof) generally constitute at least about 30 wt %, at least about 50 wt %, or at least about 75 wt % of the water-soluble fraction of pretreated feedstock. Typically, fermentable sugars constitute from about 50 to about 95 wt % and, more typically, from about 60 to about 90 wt % of the water-soluble fraction of the pretreated feedstock. Additionally or alternatively, preferably fermentable sugars (e.g., xylose) solubilized in the liquor portion of the pretreated feedstock represent a yield (basis fermentable sugar content of the feedstock) of at least about 70%, at least about 80%, or at least about 90%.

Lignin typically constitutes at least about 0.5 wt %, more typically at least about 1 wt % and, still more typically, at least about 4 wt % of the water-soluble fraction of the pretreated feedstock. Additionally or alternatively, as noted, the liquid fraction may also comprise soluble lignin-derived components. For example, the liquid fraction may comprise water-soluble lignin-derived phenolic components and relatively low molecular weight lignin degradation products.

III. Conditioning

Again with reference to FIG. 1, pretreated feedstock 45 is introduced into conditioning vessel 49 along with conditioning stream 53. Pretreated feedstock may comprise one or more components that will inhibit hydrolysis of hemicellulose and/or cellulose. These components may also inhibit fermentation of sugars derived from hemicellulose and/or cellulose. For example, lignin is often broken down into water-soluble phenolic compounds during pretreatment. Pretreated feedstock may also comprise degradation products of hemicellulose and/or cellulose hydrolysis. For example, during pretreatment hemicellulose and/or cellulose may be hydrolyzed to form a sugar that may be degraded to form one or more of hydroxymethyl furfural (HMF), furfural, and/or acetic acid. In accordance with the present invention, advantageously conditioning for inhibitor removal is conducted prior to enzymatic hydrolysis for the primary purpose of hydrolysis of either hemicellulose or cellulose to provide fermentable sugars. It is currently believed that conditioning in this manner contributes to maximum fermentable sugar and ethanol yields on both hemicellulose and cellulose.

Generally, the pretreated feedstock is contacted with material suitable for absorbing and/or forming a complex with one or more of the inhibitors and/or neutralization of one or more inhibitors. In various embodiments in which the feedstock comprises water-soluble phenolic compounds, the process comprises contact of the feedstock with material that adsorbs and/or forms a complex with one or more phenolic compounds. For example, the pretreated feedstock or its liquor portion may be contacted with an alkali metal hydroxide or oxide that forms a phenate salt. Suitable alkali sources include sodium hydroxide, calcium hydroxide, ammonium hydroxide, calcium oxide (lime), and combinations thereof. The phenate salts thus formed may be removed from the pretreated feedstock in accordance with means known in the art including, for example, filtration. By way of further example, the feedstock may be contacted with protein-containing material that will absorb the phenolic compounds and/or form a complex and/or adduct with the phenolic compounds. Various protein-containing materials (e.g., enzymes, yeast cells and fermentation broths generated during enzyme production) are suitable for this purpose. Enzymes (e.g., lacase) may provide degradation of phenolic compounds. In addition, protein-containing material derived at other process stages may be utilized. For example, thin stillage and cereal mash produced as described elsewhere herein may be used for this purpose. Metal salts and/or protein-containing materials may also be used in treatment for the purpose of complexing and/or absorbing hemicellulose and/or cellulose degradation products. Suitable metal salts (e.g., ferrous sulfate and magnesium sulfate) may be introduced into the liquor fraction of the pretreated feedstock at a concentration of from about 0.05 to about 1 millimole/L (mmol/L).

Typically, pretreated feedstock is conditioned without any intermediate steps between steam treatment and addition of conditioning agents. However, since further degradation products may form in the pretreated feedstock at elevated temperature, the temperature of the feedstock prior to conditioning is preferably maintained at no more than about 140° C., or no more than about 120° C. If necessary, the pretreated feedstock may be cooled prior to conditioning to bring its temperature within these ranges.

Conditioning stream 53 is typically in the form of an aqueous liquid medium comprising one or more of the above-noted components. Typically, one or more components are present in the stream at a proportion of from about 0.25 to about 2.5 wt % and, more typically, at a proportion of from about 0.5 to about 1 wt %. Generally, the mass ratio of stream 53 to pretreated feedstock 45 introduced into conditioning vessel 49 is at least about 0.05:1, or at least about 0.1:1. For example, typically the mass ratio of stream 53 to pretreated feedstock 45 introduced into the conditioning vessel is from about 0.05:1 to about 0.25:1 and, more typically from about 0.1:1 to about 0.2:1. Contact of the pretreated feedstock with the conditioning stream within the conditioning vessel forms a conditioned feedstock 57. With respect to the principal components of value, i.e., cellulose, hemicellulose, and sugars, the composition of the conditioned feedstock generally corresponds to that of the pretreated feedstock, with the proportions of the components reduced based on dilution of the pretreated feedstock by mixing with the conditioning stream within the conditioning vessel. It is currently believed that conditioning has little, if any, impact on, for example, the cellulose, hemicellulose, solubilized sugar and/or lignin composition of the pretreated feedstock. Lignin degradation products may be removed from the pretreated feedstock by virtue of complexing or reaction with a component of the conditioning stream. For example, generally the conditioned feedstock 57 is in the form of a slurry comprising a solids fraction and a liquid fraction, and having a total solids content of at least about 10 wt %, at least about 20 wt %, or at least about 30 wt %. For example, typically the solids content of the conditioned feedstock is from about 10 wt % to about 50 wt % and, still more typically, from about 20 wt % to about 40 wt %.

IV. Enzymatic Hydrolysis

Again with reference to FIG. 1, conditioned feedstock 57 is introduced into vessel 61 and contacted with an enzyme-containing stream 65 for enzymatic hydrolysis to yield glucose and hemicellulose-derived fermentable sugars. Suitable enzymes include various hemicellulase and cellulase enzymes generally produced by fermenting a microorganism of the *Trichoderma* genus, including, for example, xylanase, β-xylosidase, acetyl esterase, and α-glucuronidase, endo- and exo-glucannase, cellobiase, and combinations thereof. These enzymes may be isolated from enzyme solutions by fractionation techniques known in the art including, for example, ammonium sulfate precipitation and ultrafiltration, or recovered from whole enzyme production broth.

Hemicellulose is primarily composed of polysaccharides comprising five and six carbon sugars including, for example, glucose, xylose, mannose, galactose, rhamnose, and arabinose. The hemicellulose portion of lignocellulosic biomass is typically primarily composed of xylose (a monosaccharide containing five carbon atoms and including an aldehyde functional group). Accordingly, the pretreated feedstock is typically contacted with a xylanase enzyme (enzyme stream 65 in FIG. 1). Xylanases are a class of enzymes that degrade the linear polysaccharide β-1,4-xylan into xylose. Hemicellulose also typically comprises arabinose, also a monosaccharide containing five carbon atoms and including an aldehyde functional group.

Enzyme stream 65 generally comprises an enzyme dispersed throughout and/or dissolved in a suitable liquid medium (e.g., water). Typically, the enzyme stream is in the form of a slurry having a solids content of from about 1 to about 20 wt % and, still more typically, a solids content of from about 5 to about 15 wt %. The mass ratio of enzyme stream to conditioned feedstock is generally from about 0.005:1 to about 0.1:1, typically from about 0.005:1 to about 0.1:1 and, still more typically, from about 0.007:1 to about 0.05:1.

The configuration of the vessel for contact of the enzyme and pretreated feedstock is not narrowly critical and may be readily selected by one skilled in the art. For example, in various embodiments, the hydrolysis is conducted continuously utilizing a plug flow reactor. Enzymatic hydrolysis of hemicellulose may also be conducted as a batch process utilizing a stirred tank reactor. Regardless of the precise nature of the process (e.g., batch or continuous), preferably the mixture of pretreated feedstock and enzyme is agitated to promote contact and, therefore, promote hydrolysis of hemicellulose to simple sugars that may be fermented to produce ethanol.

The precise conditions of hydrolysis are not narrowly critical, but generally are selected and controlled to provide suitable sugar yields. Typically, the enzyme loading in the contact zone is at least about 1 Filter Paper Unit (FPU) (i.e., International Units of filter paper activity in micromoles of glucose per minute) per g glucan or cellulose, more typically at least about 2 FPU per g glucan or cellulose and, still more typically, at least about 5 FPU of enzyme per g glucan or cellulose. In various preferred embodiments, the enzyme loading within the reactor is from about 2 to about 40 FPU per g glucan or cellulose, from about 4 to about 20 FPU per g glucan or cellulose, or from about 5 to about 15 FPU per g glucan or cellulose. The temperature at which the hydrolysis reaction is conducted is not narrowly critical, but typically is from about 30° C. to about 70° C. (e.g., about 50° C.). Additionally or alternatively, the hydrolysis is typically conducted at a pH of from about 4 to about 6 and, more typically, from about 4.5 to about 5.5.

Contact of the pretreated feedstock and the hemicellulase enzyme generally provides a pretreated hydrolyzate 69 comprising a liquid phase comprising solubilized hemicellulose-derived fermentable sugars and a solid phase comprising cellulose and lignin. For example, typically the solubilized hemicellulose constitutes from about 10 wt % to about 80 wt % oligomeric sugars. Enzymatic hydrolysis of hemicellulose typically has little effect, if any, on the cellulose and lignin portions of the solids fraction of the pretreated feedstock. Typically, the pretreated hydrolyzate contains solubilized hemicellulose at a concentration of at least about 8 wt %, preferably at least about 10 wt % and, more preferably, at least about 12 wt %. Preferably, enzymatic hydrolysis provides a hemicellulose-derived sugar yield (e.g., xylose) of at least about 70%, more preferably at least about 80% and, still more preferably, at least about 90% (basis hemicellulose content of the pretreated feedstock).

V. Sugar Recovery

Hemicellulose-derived fermentable sugars may be fermented to produce ethanol. As shown in FIG. 1, an aqueous fraction comprising one or more hemicellulose-derived sugars (e.g., $C_5$ sugar(s)) is removed, or separated from the pretreated hydrolyzate 69 to provide fermentable sugars that may be utilized for fermentation to ethanol as detailed elsewhere herein. For removal of the $C_5$ sugar fraction, pretreated hydrolyzate 69 is introduced into sugar recovery vessel or device 73 which comprises a solids/liquid separation instrumentality such as, e.g., a screen, filter, centrifuge, settler, percolator, extraction column, flotation vessel, or combination thereof. The aqueous fraction comprising hemicellulose-derived fermentable sugars is combined with a liquid medium (e.g., water) 77 to form a hemicellulose-derived sugar fraction 81. The precise composition of the liquid medium is not narrowly critical. However, in various preferred embodiments, the washing liquid is supplied by recycle from elsewhere in the process. For example, the liquid medium (e.g., water) may be provided by thin stillage produced as detailed elsewhere herein. In various preferred embodiments, washing for sugar recovery includes counter-current contact of the washing liquid and aqueous fraction in a suitable apparatus.

Hemicellulose-derived sugar fraction 81 is typically in the form of a slurry, or filtered liquor having a dissolved solids content of at least about 5 wt %, or at least about 6 wt %. Typically, the solids content of the hemicellulose-derived sugar fraction is from about 5 to about 10 wt % and, more typically, from about 7 to about 9 wt %. The total sugar content (e.g., glucose, xylose, arabinose, mannose, and galactose) of the hemicellulose-derived sugar-rich fraction 81 is generally at least about 5 wt %, or at least about 6 wt % (basis total fraction weight). Typically, the sugar content of the hemicellulose-derived sugar-rich fraction is from about 5 to about 10 wt % and, more typically, from about 6 to about 9 wt %. Generally, the xylose content of the hemicellulose-derived sugar-rich fraction is at least about 2.5 wt %, or at least about 4 wt % (basis total fraction weight). Typically, the xylose content of the hemicellulose-derived sugar-rich fraction is from about 2.5 to about 9 wt % and, still more typically, from about 5 to about 7 wt % (basis total fraction weight). Recovery of the hemicellulose-derived sugar fraction 81 from the pretreated hydrolyzate 69 generally provides a residual thickened fraction 85 that typically comprises a cake, or slurry comprising a solid phase comprising cellulose and lignin, and a residual liquid phase comprising hemicellulose-derived fermentable sugars. Preferably, the solids/liquid separation is conducted in accordance with conventional methods known in the art utilizing, for example, a screen, filter, centrifuge, settler, vacuum belt washer, pressure filter, membrane filter, extraction column, flotation vessel, countercurrent screw extractor, or screw press. Preferably, sugars are recovered from the pretreated hydrolyzate utilizing a vacuum belt filter or countercurrent screw extractor or extraction column. Additionally or alternatively, recovery of a hemicellulose-derived sugar fraction from the pretreated hydrolyzate may comprise contacting the hydrolyzate with a suitable extraction medium.

VI. $C_5$ Sugar Fermentation

In accordance with the present invention and, more particularly, in accordance with the process depicted in FIG. 1, hemicellulose-derived fermentable sugars (i.e., $C_5$ sugars) may be fermented to produce ethanol. In particular, these sugars may be converted to ethanol in parallel with fermentation of cellulose-derived sugars (as detailed elsewhere herein). In this manner, the process depicted in FIG. 1 provides improved ethanol yield as compared to processes that rely solely on cellulose-derived sugars for ethanol production.

Again with reference to FIG. 1, a portion of the hemicellulose-derived (i.e., $C_5$) sugar fraction 81 is introduced into a yeast adaptation vessel 89 for production of yeast for fermentation of $C_5$ sugars. Typically, the portion of the sugar fraction 81 introduced into yeast adaptation vessel 89 constitutes from about 0.5 to about 10 wt % and, more typically, from about 2 to about 6 wt % of the entire $C_5$ sugar fraction present in enzyme treatment vessel 73.

Along with a portion of the $C_5$ sugar fraction, yeast culture 93 is introduced into yeast adaptation vessel 89 to grow yeast for fermentation of the $C_5$ sugars and/or transform and adapt the yeast to be effective in fermentation of $C_5$ sugars.

Suitable yeast include those generally known in the art. In various preferred embodiments, the yeast is *Pichia stipitis*, but various other species of yeast may be utilized. The method of yeast adaptation is not narrowly critical and generally proceeds in accordance with conventional methods known in the art including, for example, as described in Keller et al. "Yeast Adaptation on Softwood Prehydrolysate," Applied Biochemistry and Biotechnology, 1998, Pages 137-148, Volume 70-72, which the entire contents of is incorporated herein by reference for all relevant purposes. Generally, the mass ratio of yeast and $C_5$ sugar fraction introduced into the yeast adaptation vessel is at least about 0.05:1, or at least about 0.1:1. For example, typically the mass ratio of yeast and $C_5$ sugar fraction is from about 0.05:1 to about 0.25:1 and, more typically, from about 0.1:to about 0.2:1. Yeast 93 is typically in the form of a solution or slurry of yeast dissolved in or dispersed throughout a suitable liquid medium. For example, in various embodiments yeast 93 has a total solids content of from about 1 to about 20 wt %, or from about 5 wt % to about 15 wt %. Typically, the yeast-containing liquid medium contains the yeast at a concentration of from about 0.60 to about 150 g/L, or from about 0.80 to about 120 g/L.

Although the foregoing and following discussion focuses on use of yeast in fermentation of $C_5$ sugars, it is to be understood that any organism (e.g., yeast or bacteria) suitable for metabolizing $C_5$ sugars may be utilized in the process of the invention.

Combining yeast and the $C_5$ sugar fraction provides a yeast inoculum 97 for use in fermentation of $C_5$ sugars. Yeast inoculum is generally in the form of a slurry comprising the yeast recovered from yeast adaptation vessel. More particularly, yeast inoculum is typically in the form of a slurry of yeast dissolved in and/or dispersed throughout a liquid medium. Typically, yeast inoculum has a yeast concentration of from about 15 g/L to about 25 g/L and, more typically, a yeast concentration of from about 17 g/L to about 22 g/L. Additionally or alternatively, typically the yeast inoculum slurry a total solids content of from about 1 wt % to about 10 wt % and, more typically, a total solids content of from about 2 wt % to about 6 wt %.

As shown in FIG. 1, along with yeast 93, supplement 91 is introduced into yeast adaptation vessel 89. The supplement is generally in the form of a solution and comprises syrup, cane molasses, beet molasses, water, urea, commercial yeast nutrients, or a combination thereof. Although shown in FIG. 1, it is to be understood that use of supplement in yeast adaptation vessel is not required in accordance with the present invention. Also, in various preferred embodiments, to promote yeast cell growth and adaptation to inhibitors, filtered air is supplied to the adaptation vessel (not shown in FIG. 1) to provide advantageous oxygen transfer required for yeast growth.

Yeast inoculum 97 is introduced into fermentation vessel 101 along with $C_5$ sugar fraction 81 recovered from the enzyme treatment vessel but not introduced into the yeast adaptation vessel. The relative proportions of yeast inoculum and $C_5$ sugar fraction introduced into the fermentation vessel are not narrowly critical and depend on a variety of factors including, for example, the composition of each stream. For example, as the proportion of yeast in the inoculum increases and/or the proportion of $C_5$ sugars in the sugar fraction increases, reduced proportions of inoculum may be required to obtain suitable yields of ethanol on $C_5$ sugars. Typically, however, the mass ratio of yeast solids to $C_5$ sugar fraction is from about 0.01:1 to about 1:1 and, more typically, from about 0.05:1 to about 0.5:1 (e.g., from about 0.05:1 to about 0.1:1). Typically, the concentration of yeast in the yeast inoculum is from about 0.15 to about 30 g/L and, more typically, from about 15 to about 25 g/L.

The configuration of the fermentation vessel is not narrowly critical and may be readily selected from conventional apparatus by one skilled in the art. The conditions of the contact of the $C_5$ sugar fraction with the yeast inoculum are likewise not narrowly critical. Typically, however, the $C_5$ sugar fraction and yeast inoculum are contacted at a temperature of from about 20° C. to about 60° C. and, more typically, at a temperature of from about 25° C. to about 40° C.

Again with reference to FIG. 1, contacting the $C_5$ sugar fraction and yeast inoculum forms a $C_5$ fermentate 101. Generally, $C_5$ fermentate is an aqueous mixture of water, ethanol, and unconverted sugars of the $C_5$ sugar fraction. Typically, the concentration of ethanol in the $C_5$ fermentate is at least about 1 wt %, at least about 2 wt %, or at least about 4 wt %. However, the composition of the $C_5$ fermentate generally varies depending on, for example, the composition of the sugar fraction introduced into the fermentation vessel and the relative proportions of yeast inoculum and $C_5$ sugar fraction introduced into the vessel. Preferably, the composition of the $C_5$ fermentate represents suitable ethanol yields based on the fermentable sugar content of the $C_5$ sugar fraction. For example, generally the ethanol yield of the $C_5$ fermentate is at least about 50%, at least about 60%, or at least about 70%. It is currently believed that ethanol yields satisfying these limits, and higher, are achieved in accordance with the process depicted in FIG. 1. The residual sugar content of the $C_5$ fermentate depends on the composition of the $C_5$ sugar fraction and the ethanol yields achieved, but preferably constitutes no more than about 40 wt % and, more preferably, no more than about 30 wt % of the fermentable sugar content of the $C_5$ sugar fraction. Unfermented sugars may be converted to biogas in an aerobic digestion step, which may be incorporated into the wastewater treatment system.

VII. Lignin Extraction

As noted, recovery of $C_5$ sugar fraction 81 from enzymatic hydrolyzate 69 yields a residual thickened fraction 85 in the form of a cake or concentrated slurry comprising solid phase cellulose and lignin (i.e., cellulose/lignin residual fraction). The solids content of the cellulose/lignin residual fraction is typically from about 15 to about 45 wt % and, more typically, from about 25 to about 35 wt %. The cellulose content of the solids fraction is generally from about 35 to about 55 wt %, and typically from about 40 to about 50 wt %. The solids fraction of the cellulose/lignin residual fraction typically comprises various sugars including, for example, polysaccharides such as glucan, xylan, arabinan, mannan, and galactan, monosaccharides such as xylose, arabinose, and combinations thereof. For example, in various embodiments, the total glucan content of the residual fraction is typically from about 35 to about 55 wt %, and more typically from about 40 to about 50 wt %. The total xylan content of the residual fraction is typically from about 1 to about 7 wt %, and more typically from about 1 to about 3 wt %. Additionally or alternatively, the arabinan content of the residual fraction is typically less than about 1.5 wt % and, more typically, less than about 1 wt %. The residual fraction also typically comprises various other fermentable sugars (e.g., mannose and galactose) in a proportion of less than about 1 wt %, and more typically less than about 0.5 wt %.

The lignin content of the cellulose/lignin residual fraction is generally from about 20 to about 40 wt %, and typically from about 25 to about 40 wt %. The lignin content of the solids fraction of the residual fraction is typically from about 25 to about 35 wt %, and more typically from about 30 to about 33 wt %.

As shown in FIG. 1, cellulose/lignin residual fraction 85 is introduced into lignin extraction vessel or device 105. As noted, effective pretreatment of the biomass breaks down the cellulose-hemicellulose-lignin complex (e.g., breaks bonds between lignin and hemicellulose and/or cellulose). In this manner, and as detailed elsewhere herein, hemicellulose and cellulose are available for enzymatic hydrolysis to produce fermentable sugars. Similarly, pretreatment provides lignin available for recovery as a further product of the process. Lignin-rich products are suitable for use in a variety of applications including, for example, as a phenol formaldehyde resin extender in the manufacture of particle board and plywood, manufacture of molding compounds, urethane and epoxy resins, antioxidants, feeds, fuels, pelletizing aids, drilling mud stabilizers, and cement additives. In the process depicted in FIG. 1, lignin is recovered prior to conversion of cellulose to fermentable sugars, and conversion of the cellulose-derived fermentable sugars to ethanol.

The solids fraction of the cellulose/lignin residual fraction 85 typically comprises various sugars (e.g., cellulose-derived sugars) including, for example, polysaccharides such as glucan, xylan, and arabinan, monosaccharides such as xylose and arabinose, and combinations thereof. For example, generally the total sugar content of the solids fraction is no more than about 60 wt %, no more than about 55 wt %, or no more than about 50 wt %. Typically, the total sugar content of the solids fraction is from about 40 to about 70 wt % and, more typically, from about 50 to about 65 wt %. More particularly, the total glucan content of the cellulose/lignin residual fraction is typically from about 40 to about 60 wt %, and more typically from about 45 to about 55 wt %. The total xylan content is typically from about 1 to about 10 wt %, and more typically from about 1 to about 5 wt % (e.g., from about 1 to about 3 wt %). Additionally or alternatively, the arabinan content of the cellulose/lignin residual fraction is typically from about 0.5 to about 3 wt %, and more typically from about 1 to about 2 wt %.

The lignin content of the cellulose/lignin fraction is typically from about 25 to about 45 wt %, more typically from about 28 to about 42 wt % and, still more typically, from about 30 to about 40 wt %.

Again with reference to FIG. 1, an extraction solvent 109 is introduced into lignin extraction vessel or device 105 along with the cellulose/lignin residual fraction 85. The extraction solvent may be in the form of an organic solvent comprising methanol, ethanol, butanol, acetone, and combinations thereof. The extraction solvent may also comprise an alkali metal hydroxide, e.g., sodium hydroxide, potassium hydroxide, ammonium hydroxide, or a combination thereof. In various preferred embodiments, the extraction solvent comprises sodium hydroxide dissolved in water and, more particularly, is in the form of an aqueous solution of sodium hydroxide containing sodium hydroxide at a concentration of from about 0.5 to about 2 wt %, or from about 0.5 to about 1 wt %. Neither the conditions of nor the manner of contact of the cellulose/lignin fraction with the extraction solvent are narrowly critical and are generally conducted in accordance with conventional methods known in the art. See, for example, Canadian Patent Nos. 1 267 407 and 1 322 366 and U.S. Pat. Nos. 3,817,826; 4,470,851; 4,764,596; 4,908,099; and 4,966,650, the entire contents of which are incorporated herein by reference for all relevant purposes. For example, in accordance with the embodiment depicted in FIG. 1, the extraction solvent is an alkaline aqueous medium having a pH of from about 10 to about 14 (e.g., about 13). Additionally or alternatively, the temperature of the extraction solvent is typically from about 30° C. to about 60° C., and more typically from about 40° C. to about 50° C. (e.g., about 45° C.).

Mixing the cellulose/lignin residual fraction and extraction solvent within an extraction zone of the extraction vessel forms an extraction mixture comprising a liquid fraction comprising lignin (e.g., lignin dissolved in the extraction solvent) and a solid phase comprising cellulose and depleted in lignin relative to the cellulose/lignin residual fraction. A lignin fraction 113 is separated from the extraction mixture. Lignin typically constitutes at least about 1 wt %, more typically at least about 2 wt % and, still more typically, at least about 3 wt % of the lignin fraction. For example, lignin generally constitutes from about 1 to about 10 wt %, or from about 2 to about 6 wt % of the lignin fraction. Generally at least about 60 wt %, at least about 70 wt %, at least 80 wt %, or at least about 90 wt % of the lignin is soluble in the lignin fraction.

As shown in FIG. 1, lignin extract 113 is introduced into vessel 113A for recovery of a lignin-rich product from the extract. Recovery of the lignin-rich product from the lignin extract generally proceeds in accordance with conventional methods known in the art (e.g., precipitation) as described, for example, in U.S. Pat. No. 4,966,650 to Delong et al., the entire contents of which are incorporated herein by reference for all relevant purposes. As shown in FIG. 1, acid 114 is introduced into vessel 113A for precipitation of the lignin-rich solids from the lignin extract. In various preferred embodiments, including the embodiment shown in FIG. 1, acid 114 is in the form of a relatively concentrated acid. For example, acid 114 may be in the form of a sulfuric acid solution containing at least about 50 wt % sulfuric acid, at least about 80 wt % sulfuric acid, or at least about 90 wt % sulfuric acid.

Contacting acid 114 and lignin extract 113 within vessel 113A generally forms a lignin product mixture 114A comprising lignin precipitates that is introduced into vessel 115 for removal of moisture from the liqnin product mixture (e.g., a vessel including a filter and dryer) to form a lignin powder product 116 and a waste stream 116A. Removal of moisture from the lignin product mixture generally proceeds in accordance with conventional methods known in the art including, for example, by heating the mixture to temperatures in excess of about 70° C., or in excess of about 90° C.

Lignin product 116 is typically in the form a particulate (e.g., powder) product having a moisture content of no more than about 20 wt %, more typically no more than about 15 wt %, and preferably no more than about 10 wt %. Generally, the lignin content of lignin product 113 is at least about 75 wt %, or at least about 80 wt %. Preferably, the lignin content of the lignin product is at least about 85 wt % and, more preferably, at least about 90 wt %. One advantage of recovery of a lignin product as shown in FIG. 1 (i.e., prior to recovery and fermentation of cellulose-derived sugars) is allowing for utilizing less reactors during enzymatic hydrolysis of cellulose and/or reactors of reduced reactor volume during enzymatic hydrolysis than typically required in conventional processes.

Again with reference to FIG. 1, a wet cake 117 comprising solid phase cellulose fibers is removed from lignin extraction vessel 105. The solids content of the wet cake is typically at least about 10 wt %, more typically at least about 20 wt % and, still more typically, at least about 30 wt %. The solids fraction of the wet cake 117 generally comprises glucan, xylan, arabinan, mannan, galactan, lignin, ash, and combinations thereof. Solid phase cellulose fibers are generally recovered by solids/liquid separation conducted in accordance with conventional methods known in the art including, for example, utilizing a screen, filter, centrifuge, settler, screw press or belt press. In certain preferred embodiments, solid phase cellulose fibers are recovered by filtration of the wet cake.

VIII. Cellulose Hydrolysis and Fermentation

Generally in accordance with the present invention, cellulose is subjected to enzymatic hydrolysis for the primary purpose of hydrolysis of cellulose to produce fermentable sugars. In accordance with the foregoing, cellulose hydrolysis and fermentation feedstock may be provided by various treatment protocols, and combinations thereof. For example, feedstock may comprise biomass that has been subjected to pretreatment, conditioning, and xylan hydrolysis in accordance with the foregoing discussion. In various embodiments, the feedstock comprises biomass that has been subjected to pretreatment and directly thereafter subjected to enzymatic hydrolysis of cellulose without intermediate conditioning and/or xylanase treatment. That is, pretreated feedstock 45 shown in FIG. 1 is subjected to enzymatic hydrolysis for the primary purpose of hydrolysis of cellulose to fermentable sugars. Regardless of the precise combination of stages prior to enzymatic hydrolysis of cellulose, the feedstock is generally in the form of a slurry, or cake comprising a solid fraction or phase comprising cellulose or lignin.

In accordance with the process of FIG. 1, for enzymatic hydrolysis of cellulose, wet cake 117 is generally contacted with a cellulase enzyme and a liquid medium (e.g., water). Cellulases are a class of enzymes produced chiefly by fungi, bacteria, and protozoans that catalyze the hydrolysis of cellulose (cellulolysis) into glucose, cellobiose, cellotriose, cellotetrose, and longer chain cellodextrins. Cellulase includes both exohydrolysase and endohydrolysases that are capable of recognizing cellulose, or cellodextrins, as substrates. Cellulase enzymes may include endoglucanases, cellobiohydrolysases, beta-glucosidases, alone or in combination.

Conversion of cellulose to fermentable sugars (e.g., six-carbon sugars such as glucose) by enzymatic hydrolysis is referred to as saccharification. Sugars produced by saccharification are then fermented to produce ethanol by contact of the fermentable sugars and yeast or other suitable fermenting organism(s). In accordance with the present invention, enzymatic hydrolysis of cellulose may be conducted in accordance with methods known in the art. For example, the time, temperature, and pH of the saccharification are not narrowly critical and may generally fall within well-recognized limits. Typically, enzymatic hydrolysis of cellulose is conducted under ambient pressure conditions and at a temperature of from about 20° C. to about 80° C. and, more typically, from about 30° C. to about 60° C.

As shown in FIG. 1, wet cake 117 and enzyme 121 are introduced into cellulose hydrolysis vessel 125 along with water stream 129. The cellulose content of the cake is typically from about 55 to about 80 wt % (dry weight basis), more typically from about 60 to about 80 wt % and, still more typically, from about 65 to about 75 wt %. The initial solids loading introduced into the cellulose hydrolysis vessel is generally at least about 10 wt %, at least about 15 wt %, or at least about 20 wt %. Typically, the initial solids loading introduced into the reactor is from about 10 wt % to about 30 wt % and, more typically, from about 15 wt % to about 25 wt %.

Generally, the mass ratio of water to wet cake solids introduced into the hydrolysis vessel and/or a hydrolysis zone therein is at least about 1.5:1, at least about 1.8:1, or at least about 2.1:1. Typically, the mass ratio of water to wet cake introduced into the hydrolysis vessel and/or a hydrolysis zone is from about 1.5:1 to about 3:1, more typically from about 1.8:1 to about 2.7:1 and, even more typically, from about 2:1 to about 2.5:1.

One measure of the effectiveness of pretreatment is the proportion of enzyme required to provide suitable fermentable sugar yields. Due to the cost of the enzyme, preferably pretreatment increases the bioavailability of cellulose in a manner that allows for use of a relatively low proportion of enzyme. In accordance with the present invention, enzymatic hydrolysis of cellulose may be conducted at enzyme loadings of no more than about 40 FPU per g cellulose, no more than about 30 FPU per g cellulose, or no more than about 25 FPU per g cellulose. Typically, the enzyme loading is within the range of from about 2 to about 20 FPU per g cellulose, more typically from about 4 to about 15 FPU per g cellulose and, still more typically, from about 5 to about 10 FPU per g cellulose. Generally, the mass ratio of enzyme to dry cake introduced into the hydrolysis vessel and/or a hydrolysis zone is at least about 0.005, at least about 0.01, or at least about 0.02. Typically, the mass ratio of enzyme to wet cake is from about 0.007 to about 0.1, more typically from about 0.008 to about 0.08 and, still more typically, from about 0.01 to about 0.05.

Wet cake (i.e., cellulose), cellulase enzyme, and water are generally contacted within the hydrolysis vessel and/or a hydrolysis zone at a temperature of from about 25° C. to about 65° C., or from about 35° C. to about 50° C. The duration of contact is typically from about 12 to about 168 hours, more typically from about 24 to about 120 hours and, still more typically, from about 48 to about 96 hours.

Contacting cellulose, cellulase enzyme, and water yields a cellulose hydrolyzate comprising cellulose-derived sugars (i.e., a $C_6$ hydrolyzate). These include, for example, glucose, dextrose, fructose, and levulose. Generally, the total yield of $C_6$ sugars in the hydrolyzate (based on the total polysaccharide content of the wet cake introduced into the hydrolysis vessel) is at least about 50%, at least about 60%, or at least about 70%. Preferably, the total yield of $C_6$ sugars is at least about 80% and, more preferably, at least about 90% (e.g., about 95%). Typically, the total solids content of the hydrolyzate is from about 10 wt % to about 40 wt % and, more typically, from about 20 wt % to about 30 wt %. Typically, the mass ratio of soluble solids to insoluble solids (e.g., cellulose, glycan, and cellulase enzyme) is from about 0.8:1 to about 1.2:1 and, more typically, from about 0.9:1 to about 1.1:1 (e.g., about 1:1).

Glucose and other fermentable sugars produced by saccharification may then be fermented to produce ethanol in accordance with methods known in the art. Again with reference to FIG. 1, cellulose hydrolyzate 133 is removed from hydrolysis vessel 125 and is introduced into simultaneous saccharification and fermentation (SSF) vessel 137 for further sugar formation and conversion of sugars to ethanol. SSF is generally conducted in accordance with conventional methods known in the art including, for example, as described in Dowe et al., "SSF Experimental Protocols—Lignocellulosic Biomass Hydrolysis And Fermentation", National Renewable Energy Laboratory, 2001, 18 pages, the entire contents of which are incorporated herein by reference for all relevant purposes. The configuration of the SSF reactor is not narrowly critical and may be readily selected by one skilled in the art. Preferably, the SSF reactors are suitable for batch or continuous operation (e.g., individual or a series of continuous stirred-tank reactors).

Further in accordance with the present invention, conversion of cellulose to fermentable sugars is conducted solely via SSF. In accordance with such embodiments, wet cake 117 is introduced into SSF vessel 137 for conversion of cellulose to fermentable sugars. Operation of the process in this manner without a separate cellulose hydrolysis step provides a process of reduced cost. However, while utilizing SSF alone for generation of fermentable sugars may provide improvements in process economies, it is to be understood that the process depicted in FIG. 1 can be practiced in an economical manner.

Along with cellulose (i.e., $C_6$) hydrolyzate 133, yeast inoculum 141 is introduced into SSF vessel 137. Suitable yeast include those noted above and, in various preferred embodiments, the yeast is *Sacchromyces cerevisiae*. Yeast inoculum 141 introduced into the SSF vessel comprises the yeast dispersed throughout an aqueous medium. Typically, the yeast content of the yeast inoculum is from about 0.1 to about 5 wt % and, more typically, from about 1 to about 2.5 wt %. The relative proportions of yeast inoculum and cellulose hydrolyzate introduced into the SSF vessel depend on a variety of factors including, for example, the composition of each stream. Generally, however, the mass ratio of yeast inoculum to hydrolyzate introduced into the SSF vessel is from about 0.01:1 to about 0.25:1, or from about 0.02:1 to about 0.1:1. Although not narrowly critical, preferably saccharification and fermentation are complete after a period of operation of no more than about 168 hours, no more than about 144 hours, or no more than about 96 hours. Contacting cellulose hydrolyzate 133 and yeast inoculum 141 within SSF vessel 137 yields a $C_6$ fermentate 145. Generally, the $C_6$ fermentate is a mixture of water, ethanol, and unconverted sugars and fibers (e.g., carbohydrate, lignin, and ash) of the enzymatic hydrolyzate. The overall composition of the $C_6$ fermentate generally varies depending on, for example, the composition of the enzymatic hydrolyzate, yeast inoculum, and the relative proportions introduced into the SSF vessel. Preferably, the composition of the $C_6$ fermentate represents suitable yields of ethanol based on the fermentable sugar content of the enzymatic hydrolyzate. For example, generally the ethanol yield of the $C_6$ fermentate is at least about 20%, at least about 30%, or at least about 40%. It is currently believed that ethanol yields satisfying these limits, and higher, are achieved in accordance with the process depicted in FIG. 1. Typically, the concentration of ethanol in the $C_6$ fermentate is at least about 2 wt %, more typically at least about 4 wt % and, still more typically, at least about 5 wt %. The residual fermentable sugar content of the $C_6$ fermentate also depends on a variety of factors including, for example, the composition of the enzymatic hydrolyzate and ethanol yield achieved. Typically, however, the residual fermentable sugar content of the $C_6$ fermentate is less than about 5 g/L, more typically less than about 3 g/L and, still more typically less than about 2 g/L. Unconverted $C_6$ sugars may be converted to biogas during the anaerobic digestion step of wastewater treatment and/or concentrated and combusted in a biomass boiler.

IX. Ethanol Recovery

Again with reference to FIG. 1, $C_6$ fermentate 145 is introduced into a still 149 into which steam 155 is introduced wherein the fermentate is distilled to produce a high wines fraction 153 derived from C6 sugars (or C6 and C5 sugars) and a bottoms product 157. Distillation generally proceeds in accordance with conventional methods known in the art using conventional apparatus as described, for example, in Distillation Technology, GEA Wiegand, 16 pages and Bioethanol Technology, GEA Wiegand, 16 pages, the entire contents of which are incorporated herein by reference for all relevant purposes. The high wines fraction may then be dehydrated to produce ethanol product. Generally, conventional distillation apparatus known in the art are suitable for use in accordance with the present invention. These include, for example, distillation columns including dual flow and cross flow trays. However, because of the high suspended solids content of the fermentate, or beer stream, generally dual flow sieve trays or cross-flow valve trays are preferred. In various preferred embodiments, columns including cross flow valve trays are preferred because of the higher turn down ratio and higher efficiency often provided by cross flow valve trays. Suitable valve trays include, for example, NORPRO PROVALVE trays.

As detailed herein, various strategies of the present invention preferably maximize ethanol yields. For example, in various preferred embodiments of the present invention ethanol yields of at least about 70%, at least about 75%, or at least about 80% (basis total cellulose and hemicellulose content of feedstock) may be achieved.

X. Ethanol Co-Products

Ethanol distillation bottoms product 157 is generally in the form of a slurry, or cake comprising solid remnants of the feedstock. The bottoms product may be separated (e.g., by centrifugation) to produce high solids distiller's grains 161 and thin stillage 165.

The distiller's grains 161 may be dried to produce a solid protein product. For example, dried distiller's grains having a protein content of at least about 10 wt %, at least about 15 wt %, or at least about 20 wt % may be prepared upon drying of the distiller's grains.

Thin stillage 165 is generally in the form of an aqueous waste stream having total solids content of no more than about 2 wt %, and preferably no more than about 1 wt %. Accordingly, thin stillage may be subjected to treatment prior to disposal (not shown in FIG. 1) and/or may be utilized as process water (also not shown in FIG. 1). For example, as noted, thin stillage may provide at least a portion of the process water utilized during conditioning and/or sugar extraction as detailed elsewhere herein.

XI. Integrated Cellulase Generation

Further in accordance with the present invention, enzyme for use in enzymatic hydrolysis may be prepared utilizing a portion of feedstock. As shown in FIG. 1, a portion of the wet cake 117 is introduced into vessel 118 along with supplement stream 119 for production of enzyme.

Supplement 119 generally comprises an aqueous biosynthesis medium, nitrogen and/or nutrient source, and a microbe that is effective to express a cellulase enzyme.

Suitable biosynthesis media include water, sugars, nutrients, and combinations thereof. In various preferred embodiments, the biosynthesis medium is water. Suitable sugar, nitrogen and/or nutrient sources include corn syrup, molasses, cereal mash and distiller's dried grains remaining after recovery of ethanol. Nutrients present in the supplement include, for example, calcium, phosphorus, potassium, magnesium, iron, manganese, zinc, and combinations thereof. Suitable microbes include *Trichoderma reseei, Aspergilus*, and combinations thereof. Supplement 119 also typically comprises glucose that can be utilized by the microbe for formation thereof.

Typically, the glucose content of supplement 119 is from about 10 wt % to about 50 wt % and, more typically, from about 20 wt % to about 40 wt %. The nitrogen and/or nutrient source typically constitutes from about 1 wt % to about 20 wt % and, more typically, from about 5 wt % to about 15 wt % of the supplement. However, the precise composition of the supplement is not narrowly critical. Substrates suitable for enzyme production are detailed in Example 4. Generally, the substrates provide a carbon source, nitrogen source, and nutrients for growing the enzyme-producing microorganisms. For example, suitable carbon sources include glucose syrups (e.g., having a glucose content of 75% or greater), pretreated (and preferably washed) biomass, cereal mash, and distiller's dry grains with solubles (recovered as detailed elsewhere herein). In various preferred embodiments the substrates comprise from about 45 to about 65 wt % (preferably about 55 wt %) corn syrup, from about 10 to about 20 wt % (preferably 15 wt %) washed and pretreated biomass, from about 10 to about 20 wt % (preferably about 15 wt %) cereal mash, and from about 10 to about 20 wt % (preferably about 15 wt %) distiller's dry grains with solubles. Suitable nitrogen sources include urea, ammonium hydroxide, ammonium sulfate, and combinations thereof. Suitable nutrients include corn syrup liquor, inorganic salts (e.g., containing magnesium, potassium, calcium, phosphate, iron, and manganese) and combinations thereof.

Vessel 118 generally comprises a microbe proliferation zone in which glucose, cellulose, the nitrogen and/or nutrient source, and the microbe are contacted. The mass ratio of supplement to the portion of the wet cake introduced into the vessel and/or contacted within the microbe proliferation zone is typically from about 1:1 to about 10:1 and, more typically, from about 2:1 to about 8:1. Generally, from about 0.1 to about 5 wt %, or from about 0.5 to about 2.5 wt % of the wet cake is introduced into the vessel and/or contacted with the supplement within microbe proliferation zone. Generally, the portion of the aqueous wet cake and the supplement are contacted at a temperature of from about 20° C. to about 60° C. and, more typically, at a temperature of from about 30° C. to about 50° C.

Contacting glucose, cellulose, the nitrogen/nutrient source, and the microbe within the proliferation zone of vessel 118 yields an enzyme slurry comprising a solid enzyme fraction and a liquid fraction. The solid enzyme fraction typically constitutes from about 1 to about 15 wt % and, more typically, from about 5 to about 10 wt % of the enzyme slurry. The remainder of the enzyme slurry generally comprises water. As shown in FIG. 1, enzyme 121 is introduced into cellulose hydrolysis vessel 125 along with wet cake 117.

XII. Yeast Preparation

Again with reference to FIG. 1, yeast inoculum 141 is prepared in yeast propagation vessel 138 by combining yeast supplement 139 and yeast 140. As noted, suitable yeast for use in the simultaneous saccharification and fermentation include *Sacchromyces cerivisiae*. Yeast supplement 139 generally comprises *Sacchromyces cerivisiae*, and in accordance with the embodiment depicted in FIG. 1, is a glucose syrup, or slurry, comprising glucose dispersed throughout an aqueous medium (e.g., water). More particularly, and in accordance with various preferred embodiments, yeast supplement 139 is typically a glucose syrup containing glucose in a proportion of at least about 5 wt % glucose, more typically at least about 10 wt % glucose. The conditions of yeast propagation are not narrowly critical and propagation is generally conducted in accordance with conventional methods known in the art including, for example, Scott Laboratories, Yeast Rehydration Protocol, 1 page and Propax Yeast Propagation Technology, Meura, 2 pages, the entire contents of which are incorporated herein by reference for all relevant purposes.

XIII. FIG. 3

Figure 3:
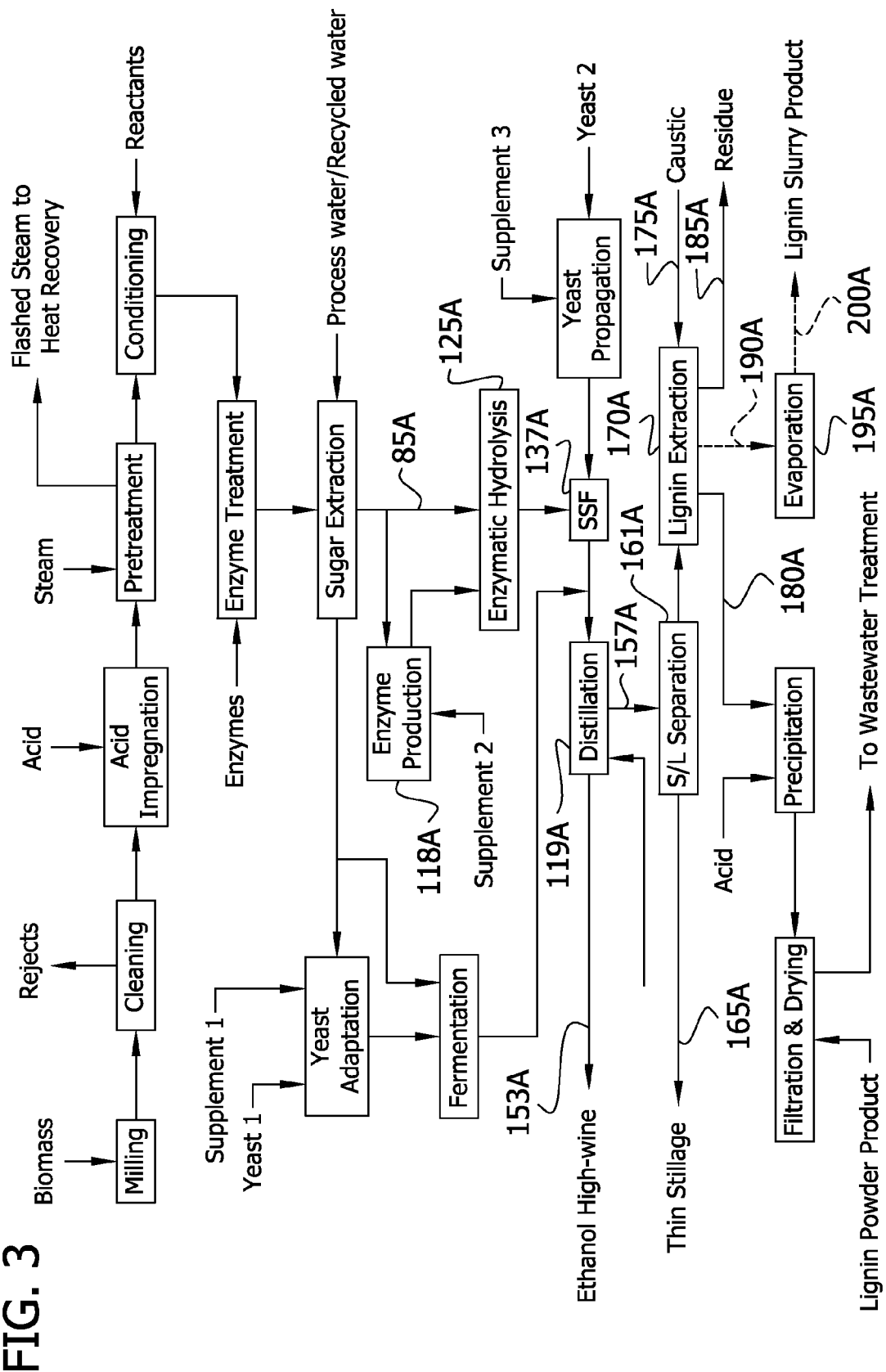
FIG. 3 depicts a process flow of another embodiment of an ethanol production process of the present invention.

FIG. 3 depicts another embodiment of a process of the present invention. Generally, preparation of pretreated feedstock, and preparation and recovery of a $C_5$ hemicellulose-derived sugar fraction proceeds in accordance with the discussion above regarding FIG. 1. Accordingly, the description of these steps of the process depicted in FIG. 3 will not be repeated. With reference to FIG. 3, recovery of a $C_5$ sugar fraction yields a residual thickened fraction 85A in the form of a cake or concentrated slurry comprising solid phase cellulose and lignin (i.e., cellulose/lignin residual fraction). Contrary to the process depicted in FIG. 1, residual thickened fraction 85A is not introduced into a vessel for extraction of lignin but, rather, a portion of the residual thickened fraction 85A is introduced into enzyme production vessel 118A while another portion is introduced into cellulose hydrolysis vessel 125A. Typically, a minor portion (e.g., less than about 5 wt %, less than about 2 wt %, or less than about 1 wt %) of the residual thickened fraction 85A is introduced into enzyme production vessel 118A. The composition of residual thickened fraction 85A generally corresponds to the composition of residual thickened fraction 85 discussed above in connection with FIG. 1.

Again with reference to FIG. 3, cellulose hydrolysis within cellulose hydrolysis vessel 125A, SSF within vessel 137A, and distillation within still 149A generally proceed in accordance with the discussion set forth above regarding the process of FIG. 1. However, certain adjustments may be made based on the varied composition of the cellulose/lignin residual fraction introduced into cellulose hydrolysis vessel 125A. For example, generally in accordance with the process of FIG. 3 an increased proportion of residual fraction is introduced into the cellulose hydrolysis vessel as compared to the process of FIG. 1. Thus, an increased proportion of water is typically introduced into the cellulose hydrolysis vessel.

Further in accordance with the process depicted in FIG. 3, distillation yields a high wines fraction 153A derived from C6 sugars (or C6 and C5 sugars) and a bottoms product 157A. Bottoms product 157A is separated (e.g., by centrifugation) to produce high solids distiller's grains 161A and thin stillage 165A.

As noted above in connection with the process depicted in FIG. 1, the distiller's grains are generally rich in protein derived from the initial protein content of the biomass and based on protein generated during the process (e.g., during integrated enzyme generation). In addition, in accordance with the process depicted in FIG. 3, a significant fraction of lignin remains in the distillation bottoms product since lignin fractionation does not occur prior to derivation of fermentable sugars by enzymatic hydrolysis of hemicellulose and cellulose and fermentation of the sugars. The lignin content of the distiller's grains 161A is generally from about 30 to about 60 wt %, and typically from about 40 to about 60 wt %.

Contrary to the process depicted in FIG. 1, in accordance with the process depicted in FIG. 3, a lignin-rich product is not recovered prior to enzymatic hydrolysis of cellulose to fermentable sugars or production of ethanol therefrom. Instead, insoluble lignin and lignin products remain in the distiller's solid residue or cake (i.e., dry grains) 161A. As shown in FIG. 3, distiller's solid residue 161A is introduced into lignin extraction vessel 170A along with an extraction solvent 175A. The composition of the extraction solvent is not narrowly critical, but generally is in the form of the extraction solvents described above. In various preferred embodiments, the extraction solvent is in the form of an aqueous solution of sodium hydroxide. Typically, the distiller's solid residue and extraction solvent are contacted at a temperature of from about 30° C. to about 60° C. and, more typically, from about 40° C. to about 50° C. (e.g., about 45° C.).

Mixing the distiller's solid residue and extraction solvent within an extraction zone of the extraction vessel forms an extraction mixture comprising an extract comprising lignin and a wet cake. Again with reference to FIG. 3, lignin extract 180A and lignin wet cake 185A are removed from the lignin extraction vessel.

The lignin extract comprises a solids fraction and a liquid fraction and typically has a total solids content of from about 1 to about 15 wt %, and more typically from about 2.5 to about 10 wt %. Lignin typically constitutes at least about 1 wt %, more typically at least about 2 wt % and, still more typically, at least about 3 wt % of the lignin extract. For example, lignin generally constitutes from about 1 to about 10 wt %, or from about 2 to about 6 wt % of the lignin extract. Lignin wet cake is generally in the form of a slurry containing up to 25 wt % or up to 30 wt % solids content and various impurities. Preferably, and in accordance with the embodiment depicted in FIG. 3, the wet cake does not contain lignin for recovery and, accordingly, is generally removed from the process as a waste stream.

A lignin-rich product may be recovered from lignin extract 180A generally as described above in connection with lignin extraction vessel 113A utilized in the process of FIG. 1. The lignin-rich product (typically in the form of a powder) generally exhibits any or all of the properties noted above in connection with the lignin-rich product provided by the process of FIG. 1.

Optionally (as indicated by the dashed line in FIG. 3), a lignin extract portion 190A may be recovered from lignin extraction vessel 170A and introduced into evaporator 195A for removal of moisture to form a lignin-rich product 200A. Lignin-rich product prepared by evaporation is generally in the form of a slurry of lignin-rich solids having a total solids content of from about 20 wt % to about 50 wt %, or from about 20 wt % to about 40 wt %. The lignin-rich slurry product may be utilized as-is in a variety of applications (e.g., wood composite adhesive) or may be further processed to provide a lignin-rich product of greater purity, or a dry powder comprising lignin monomers or other degradation products (not shown).

As further shown in FIG. 3, lignin extract 180A may be introduced into a precipitation vessel 181A where it is contacted with an acid 182A suitable for forming lignin precipitate 183A. Lignin precipitate 183A is filtered and dried in a suitable vessel 184A to form a lignin powder product 186A and lignin waste stream 187A. Lignin waste stream 187A may be removed as a waste water stream and sent for wastewater treatment.

XIV. Recovery of Heat Values

Further in accordance with the present invention, one or more process streams or residues may be introduced into a biomass boiler for recovery of heat values from organic components of the stream, or residue. The heat values thus recovered may be utilized for steam generation. In particular, heat values may be recovered from carbohydrates (e.g., unconverted $C_5$ and $C_6$ sugars) by combustion in a biomass boiler. For example, and again with reference to FIG. 1, distillation bottoms product 157 may be sent to a biomass boiler for combustion and recovery of heat values therefrom. Again with reference to FIG. 1, the distiller's solid residue 161 typically has a solids content of from about 30 to about 40 wt % (e.g., from about 32 wt % to about 38 wt % or from about 34 wt % to about 36 wt %). Thus, various alternative embodiments include sending the distiller's solid residue to a biomass boiler for recovery of heat values. The heat value (energy content) of the solid residue is typically from about 7,000 to about 8,500 British Thermal Units (BTU) per pound (lb) (dry weight basis) (BTU/lb). Additionally or alternatively, thin stillage 165 may be utilized for recovery of heat values from its organic components. As noted, typically thin stillage 165 has a total solids content of no more than about 5 wt % (e.g., no more than about 2 wt %). Accordingly, prior to introduction into the biomass boiler, the thin stillage may be subjected to evaporation to provide a feed for the biomass boiler having a suitable solids content (e.g., from about 50 to about 70 wt %). The heat value (energy content) of the concentrated thin stillage is typically from about 5,000 to about 6,500 BTU/lb.

Further in accordance with the present invention and with reference to FIG. 3, thin stillage 165A and/or lignin waste stream 187A may subjected to evaporation to provide a feed for the biomass boiler having a suitable solids content (e.g., from about 50 to about 70 wt %). The typical heat content of such a concentrated waste stream is typically from about 5,000 to about 6,500 BTU/lb.

The present invention is illustrated by the following examples which are merely for the purpose of illustration and not to be regarded as limiting the scope of the invention or the manner in which it may be practiced.

Example 1

This example details acid impregnation of corn stover (CS) harvested near Hugoton, Kans. A bale of corn stover weighing approximately 700 pounds was manually de-stringed and introduced into a tub grinder (Vermeer Corporation, Pella, Iowa, U.S.A., Model TG 7000) including a screen having openings of approximately 3 inches to provide coarsely milled feedstock. The coarsely milled corn stover was then milled through a 0.5-inch screen using a hammer mill (Bliss Industrial Inc., Ponca City, Okla. U.S.A., Model ER-2215-TF. The milled corn stover had a moisture content of approximately 11 wt %.

Following milling, 20 lb batches of the 0.5 inch milled corn stover were impregnated with sulfuric acid. For acid impregnation, the batches of corn stover were tumbled in a 70° C. jacketed double-shaft mixer while approximately 20 lb of a 3% (w/w) solution of sulfuric acid at a temperature of 70° C. was sprayed onto the milled feedstock for a period of 2 minutes. After spraying was complete, the acid-feedstock mixture was mixed for an additional 6 minutes. The resulting acid-impregnated corn stover was then held in a 70° C. jacketed surge bin before pretreatment for a hold time of from approximately 20 minutes.

Acid-impregnated corn stover was then introduced into a pre-heated batch digester having a total volume of approximately 100 liters (l). Steam under a pressure of 200 psig was introduced into the digester for heating of the corn stover for approximately 10 to 30 seconds. During the first 5 to 10 seconds of the steam injection period, a 0.5 inch vent valve on top of the digester was opened to purge air from the digester. After steam injection was completed, the acid-impregnated feedstock was held in the digester under a steam pressure of approximately 200 psig for approximately 130 seconds after which time the feedstock was discharged from the digester under a pressure of 200 psig. Discharge of the feedstock occurred over a vent time of approximately 20 seconds.

For comparison purposes, pretreatment was tested in which the feedstock was discharged under pressures below 200 psig in which the pressure was reduced to pressures of approximately 150 psig, 120 psig, and 100 psig by venting of the digester for approximately 20 seconds. For comparison purposes, pretreatment was tested in which the feedstock was subjected to first and second stages of different pressure conditions. The first stage occurred over a period of approximately 1 to 5 minutes during which time the feedstock was subjected to pressures of from approximately 150 to approximately 230 psig. After the first stage was completed, the digester was vented for approximately 10 to 30 seconds to reduce the pressure in the digester by approximately 50 to 150 psig or approximately 75 to 120 psig. The duration of the second stage pretreatment was approximately 0.2 to 5 minutes or approximately 0.5 to 3 minutes.

Samples from each batch of pretreated corn stover (PCS) were analyzed for chemical composition.

Table 1 provides the composition of the liquor in samples of corn stover pretreated at the various pressures. The moisture content of the PCS samples are not the same, with variations up to 10%. The sugar concentrations in the liquors are normalized to the moisture content as the PCS sample of the full pressure pretreatment (i.e., single-step, 200 psig pretreatment) for direct comparison.

TABLE 1

| | Discharge Pressure | | | | | | | |
|---|---|---|---|---|---|---|---|---|
| | 200 psi | | 150 psi | | 120 psi | | 100 psi | |
| Concentration in liquor, g/L | Before acid hydrolysis | After 4% acid hydrolysis | Before acid hydrolysis | After 4% acid hydrolysis | Before acid hydrolysis | After 4% acid hydrolysis | Before acid hydrolysis | After 4% acid hydrolysis |
| Glucose | 20.2 | 24.16 | 19.94 | 23.23 | 20.18 | 23.67 | 23.96 | 27.85 |
| Xylose | 79.99 | 88.79 | 85.10 | 91.66 | 89.44 | 97.63 | 92.63 | 101.60 |
| Galactose | 6.6 | 8.06 | 8.46 | 9.52 | 6.91 | 8.30 | 5.51 | 7.31 |
| Arabinose | 10.69 | 12.68 | 11.37 | 13.57 | 10.75 | 13.20 | 9.31 | 12.05 |
| Mannose | 2.23 | 2.84 | 2.01 | 2.71 | 1.81 | 2.57 | 1.54 | 2.51 |
| Cellobiose | 1.79 | — | 2.68 | — | 1.92 | — | 2.07 | — |
| Acetic Acid | 4.77 | — | 4.73 | — | 5.78 | — | 5.23 | — |
| Furfural | 1.54 | — | 1.82 | — | 2.03 | — | 2.47 | — |
| HMF | 0.87 | — | 0.90 | — | 0.71 | — | 1.05 | — |
| Total soluble sugars | 121.5 | 136.53 | 129.55 | 140.67 | 131.00 | 145.38 | 135.03 | 151.32 |

Table 2 shows the composition of washed corn stover pretreated at the various pressures.

Table 3 shows the results of enzymatic hydrolysis of washed and pretreated samples.

Table 4 shows the particle size analysis of washed PCS.

TABLE 2

| Component, wt % | Discharge pressure | | | |
|---|---|---|---|---|
| | 200 psi | 150 psi | 120 psi | 100 psi |
| Glucan | 55.96 | 56.32 | 56.47 | 55.47 |
| Xylan | 4.03 | 3.64 | 2.94 | 2.8 |
| Galactan | 0.3 | 0.3 | 0 | 0 |
| Arabinan | 0.86 | 0.88 | 0.77 | 0.67 |
| Mannan | 0.35 | 0.33 | 0 | 0 |
| Klason Lignin | 26.82 | 27.7 | 28.94 | 29.82 |
| Acid soluble lignin | 1.13 | 1.08 | 1.06 | 0.99 |
| Ash | 9.28 | 10.26 | 10.18 | 11.03 |
| Acetic acid | 0.77 | 0 | 0 | 0 |
| Mass balance | 99.50 | 100.52 | 100.35 | 100.78 |

TABLE 3

| Enzyme hydrolysis | Discharge pressure | | | |
|---|---|---|---|---|
| time, hr | 200 psi | 150 psi | 120 psi | 100 psi |
| 0 | 0.0 | 0.0 | 0.0 | 0.0 |
| 12 | 45.2 | 42.8 | 43.0 | 44.7 |
| 24 | 64.9 | 61.8 | 62.9 | 62.9 |
| 48 | 85.1 | 81.9 | 84.7 | 83.8 |
| 72 | 90.5 | 90.2 | 93.5 | 88.8 |
| 96 | 92.9 | 92.9 | 95.8 | 91.2 |

TABLE 4

| Discharge Pressure, psi | Arithmetic length (μm) | Weighted length (μm) | Width (μm) | Fine elements (% in length) | Fine elements (% in area) | Coarseness (mg/m) |
|---|---|---|---|---|---|---|
| 200 | 181 | 303 | 23.3 | 41.3 | 2.87 | 0.2283 |
| 150 | 179 | 291 | 23.4 | 41.4 | 2.73 | 0.2476 |
| 150 (unwashed PCS) | 177 | 291 | 23.3 | 41.3 | 2.71 | 0.2421 |
| 100 | 159 | 248 | 23.8 | 50.3 | 3.22 | 0.2455 |

These results indicate that two-step pretreatment provided an increase of up to approximately 11% in soluble sugar yield in comparison with the single-step pretreatment. It is believed that a significant portion, if not most of the increase can be attributable to additional xylan conversion as evidenced by the increase in xylose concentration in the liquor and reduction in xylan content of washed pretreated corn stover. It is currently believed that venting furfural during pretreatment prevents furfural from condensing on xylose, thereby leading to higher solubilized xylose yield. It is further currently believed that advantageous ethanol yield is provided by virtue of recovery and fermentation of $C_5$ sugars. Particle size and cellulose digestibility varied little between corn stover pretreated by one and two step methods.

Example 2

This example details power input required during acid impregnation carried out as described in Example 1.

Power input ranged from 1.7 to 8.5 kWh/ton of corn stover for 2 to 10 minutes mixing time. (Mixing power input=mixing power with straw and acid minus mixing power without corn stover) Acid impregnation mixing time ranged from 4 to 6 minutes, which corresponds to a power input of from 3.4 to 5.1 kWh/ton corn stover (dry weight basis). The moisture content of the milled corn stover was 12 wt % and the moisture content of the acid-impregnated corn stover was approximately 55 wt %. Tables 5 and 6 provide the results for the power input testing.

TABLE 5

Estimation of acid impregnation power consumption

| | Operation | | | | | | | | | | |
|---|---|---|---|---|---|---|---|---|---|---|---|
| | Voltage, V | Current, Amp | Run time, min | CS input as is, lb | TS of CS | Dry wt CS, lb | kVA | kW | Power consumed per batch, kWh | Power input per batch of CS, kWh | Power input per ton CS, kWh |
| Empty | 460 | 1.49 | 6 | 20 | 0.88 | 17.6 | 1.1871 | 0.9497 | 0.0950 | 0.0000 | N/A |
| CS only | 460 | 1.85 | 6 | 20 | 0.88 | 17.6 | 1.4739 | 1.1791 | 0.1179 | 0.0229 | 2.607 |
| CS plus acid solution | 460 | 2.19 | 6 | 20 | 0.88 | 17.6 | 1.7448 | 1.3959 | 0.1396 | 0.0446 | 5.070 | kVA = V * A * 1.732/1000 (Note: 1.732 is square root of 3)
kW = kVA * Power Factor (Note: Power factor (PF) for motors 1-5 HP PF = 0.75, 5-50 HP motors PF = 0.8, 50-100 HP PF = 0.85, >100 HP PF = 0.9)
Weight of CS per batch (20 lb)

| Impregnator run time, min | kWh for wet CS |
|---|---|
| 2 | 1.69 |
| 3 | 2.53 |
| 4 | 3.38 |

TABLE 5-continued

Estimation of acid impregnation power consumption

| | |
|---|---|
| 5 | 4.225 |
| 6 | 5.07 |
| 7 | 5.915 |
| 8 | 6.76 |
| 9 | 7.605 |
| 10 | 8.45 |

Normal run = 6 min

Example 3

This example provides results of particle size analysis of corn stover pretreated by a variety of combinations of conditions.

Table 6 provides the results of particle size analysis of milled corn stover using the specified U.S. Standard Sieves. Generally, the particle size distribution of pretreated corn stover is narrower than that of milled corn stover.

TABLE 6

| Sieve | Opening, mm/μm | Average retained % | Cumulative, % | Standard Deviation |
|---|---|---|---|---|
| Tray 0.265" | 6.73 mm | 0.0 | na | 0.0 |
| Tray #5 | 4 mm | 10.8 | 100 | 0.7 |
| Tray #10 | 1.68 mm | 29.2 | 89.2 | 1.5 |
| Tray #20 | 841 μm | 27.7 | 60 | 1.4 |
| Tray #40 | 420 μm | 14.6 | 32.3 | 0.6 |
| Tray #60 | 250 μm | 4.9 | 17.7 | 0.8 |
| Bottom | <250 μm | 12.8 | 12.8 | 1.1 |

Particle size analysis was conducted for (a) corn stover pretreated at various pressures; (b) water washed corn stover, and (c) fiber recovered from pretreated corn stover stillage. Generally, as described below, at reduced-pressure blow (100 psig vs full-pressure blow at 200 psig), the coarseness increases slightly. Accurately measuring the fiber length for small particles using the Fiber Quality Analyzer proved to be difficult.

Particle size data were collected using a Fiber Quality Analyzer (FQA)-MorFi OL-01 commercially available from Techpap (France). Fiber Length and Fiber Width measurements were taken. For comparison purposes, particle size analysis of wheat straw was also conducted. Results are provided in Table 6.

Fiber Length: Arithmetic average fiber length and length weighted average fiber length. Arithmetic average fiber length is the sum of all the individual fiber lengths divided by the total number of fibers measured; Length weighted average fiber length is calculated as the sum of individual fiber lengths squared divided by the sum of the individual fiber length. The data in Table 6 indicate (a) as pretreatment pressure increases fiber length increases; (b) water washing does not affect the fiber length; (c) fiber length of pretreated corn stover stillage and pretreated wheat straw are similar.

Fiber Width: measurement of length across the fiber. The results listed in Table 6 indicate (a) higher pretreatment pressure generally provides shorter fiber width up to 150 psig, after which no effect on fiber width was observed; (b) water washing does not affect fiber width; (c) the fiber width from pretreated corn stover stillage is larger than one from pretreated wheat straw stillage.

Coarseness: milligrams of fiber per meter of fiber length. The results in Table 6 indicate (a) a maximum value for coarseness (0.2476) at pretreatment pressure of 150 psig; (b) water washing process increases the fiber coarseness; (c) the coarseness from pretreated corn stover stillage is much bigger than the one from pretreated wheat straw stillage.

Fines: particles below 7 microns (above 7 microns a "fiber"). The percentage of fines on an arithmetic basis is the number of fines divided by the total number of fibers (fines included) multiplied by 100%; the percentage of fines on a length weighted basis is the sum of fines length divided by the total length of fibers and fines in the sample.

The results in Table 7 indicate (a) higher pretreatment pressure generally results in less fines up to 150 psig pressure, but above 150 psig pressure does not affect the proportion of fines on a length weighted basis; based on the number of fines (2.73) there is a minimum at a pressure of 150 psig; (b) water washing does not affect fine content; (c) pretreated corn stover stillage provides a higher proportion of fines than pretreated wheat straw stillage; (d) stillage (particularly from pretreated corn stover) includes a relatively high proportion of fines (e.g., over 95%), which raises issues during filtering during water washing.

TABLE 7

Tabel 1. Fiber properties from seven (7) samples by FQA

| | Arithmetic Length (μm) | | | Weighted Length (μm) | | | Width (μm) | | | Fine Elements (% in length) | | | Percentage of fine elts (% in area) | | | Coarseness (mg/m) | | |
|---|---|---|---|---|---|---|---|---|---|---|---|---|---|---|---|---|---|---|
| Sample | 1 | 2 | Ave. | 1 | 2 | Ave. | 1 | 2 | Ave. | 1 | 2 | Ave. | 1 | 2 | Ave. | 1 | 2 | Ave. |
| WW-PCS-200 Pisg | 180 | 182 | 181 | 300 | 305 | 302.5 | 23.2 | 23.4 | 23.3 | 41.3 | 40.5 | 41.3 | 2.94 | 2.79 | 2.865 | 0.2336 | 0.223 | 0.2283 |
| WW-PCS-150 Pisg | 178 | 179 | 178.5 | 290 | 291 | 290.5 | 23.5 | 23.3 | 23.4 | 41.4 | 40.4 | 41.4 | 2.79 | 2.67 | 2.73 | 0.236 | 0.2591 | 0.2476 |
| WW-PCS-100 Pisg | 160 | 158 | 159 | 246 | 249 | 247.5 | 23.9 | 23.7 | 23.8 | 50.3 | 50.1 | 50.3 | 3.17 | 3.27 | 3.22 | 0.2385 | 0.2524 | 0.2455 |
| WW-PCS-150 Pisg | 178 | 179 | 178.5 | 290 | 291 | 290.5 | 23.5 | 23.3 | 23.4 | 41.4 | 40.4 | 41.4 | 2.79 | 2.67 | 2.73 | 0.236 | 0.2591 | 0.2476 |
| PCS-150 Pisg | 175 | 179 | 177 | 289 | 292 | 290.5 | 23.4 | 23.2 | 23.3 | 41.3 | 40.5 | 41.3 | 2.73 | 2.68 | 2.705 | 0.2423 | 0.2418 | 0.2421 |

TABLE 7-continued

Tabel 1. Fiber properties from seven (7) samples by FQA

| Sample | Arithmetic Length (μm) | | | Weighted Length (μm) | | | Width (μm) | | | Fine Elements (% in length) | | | Percentage of fine elts (% in area) | | | Coarseness (mg/m) | | |
|---|---|---|---|---|---|---|---|---|---|---|---|---|---|---|---|---|---|---|
| | 1 | 2 | Ave. | 1 | 2 | Ave. | 1 | 2 | Ave. | 1 | 2 | Ave. | 1 | 2 | Ave. | 1 | 2 | Ave. |
| PCS-Stillage | 110 | 111 | 110.5 | 130 | 132 | 131 | 23 | 23.4 | 23.2 | 95.8 | 95.6 | 95.8 | 11.21 | 11.1 | 11.15 | 0.9574 | 0.9656 | 0.9615 |
| PCS-SSF residue | 114 | 114 | 114 | 134 | 132 | 133 | 24.3 | 24.4 | 24.35 | 93.8 | 93.8 | 93.8 | 9.66 | 9.65 | 9.655 | 1.3279 | 1.3262 | 1.3271 |
| PCS-Stillage | 110 | 111 | 110.5 | 130 | 132 | 131 | 23 | 23.4 | 23.2 | 95.8 | 95.6 | 95.8 | 11.21 | 11.1 | 11.15 | 0.9574 | 0.9656 | 0.9615 |
| PWS-Stillage | 111 | 112 | 111.5 | 128 | 131 | 129.5 | 21.3 | 21.5 | 21.4 | 87.2 | 86.8 | 87.2 | 7.35 | 7.12 | 7.235 | 0.4955 | 0.4874 | 0.4915 |

Example 4

This example details a suitable method for preparation of a cellulase enzyme. Produce enzymes for the saccharification of pretreated biomass by a genetically modified microorganism expressing high levels of the main enzymatic activities required for cellulose hydrolysis. Grow the microorganism from laboratory cultures through bioreactors of increasing volume (pre-seed and seed propagation fermentors) in order to prepare an inoculum of approximately 10% of the volume of the production fermentor in the scheduled time of approximately 144 hours.

Enzyme production generally includes (1) media preparation and (2) fermentation. Media preparation includes substrate preparation and nutrient preparation steps.

Utilize 75% glucose syrup, washed pretreated biomass, cereal mash and distiller's dry grain with solubles as substrates. These substrates generally provide a carbon source for growing the enzyme-producing microorganisms. The glucose syrup provides a high concentration of glucose that can be readily utilized by the microorganism without hindering mass transfer in the fermentation process. The washed pretreated biomass is a source of cellulose that enhances the cellulose activity of the enzymes produced towards the substrate to be hydrolyzed in the saccharification step. Hydrolyzed cereal mash and distiller's dry grain with solubles (DGS) are low-cost substrates, which are readily available in facilities including biomass ethanol production and cereal biomass ethanol production. The cereal mash and DGS also provide supplemental nitrogen source and other nutrients (e.g., Ca, P, K, Mg, Fe, Mn, and Zn). Enzyme protein yields of approximately 0.33 g protein per g of glucan and glucose available in the combined substrates may be achieved. Table 8 provides the composition of a suitable substrate.

TABLE 8

| Substrate | % dry weight of total combined substrates (dry weight basis) |
|---|---|
| Corn syrup | 55 ± 10 |
| Hydrolyzed cereal mash | 15 ± 5 |
| DGS | 15 ± 5 |
| Washed pretreated biomass | 15 ± 5 |

Blend the substrates together or slurry with the nutrient solutions before adding to the seed and production fermentors. The initial concentration (dry weight basis) of the combined substrates in the fermentors will typically be about 7% to achieve a C:N ratio of about 4:1. Through fed-batch fermentation (e.g., including stepwise introduction of substrates to the vessel), the effective substrate loading can be as high as 30% (total initial insoluble and soluble solids).

In addition to substrates described above, the microorganism requires nitrogen and nutrients for growth and enzyme protein production. The major nutrient requirements are nitrogen sources (organic and inorganic). Organic nitrogen is provided from protein contents of mash, DGS, supplemental protein sources such as soybean meal, soy protein concentrate, and Pharmamedia (a finely ground yellow flour prepared from the embryo of cottonseed; the principle component is nonhydrolyzed globular protein). The initial crude protein concentration from organic source in the fermentation step may be about 15 g/L. Inorganic nitrogen may be supplied at an initial concentration of about 12 g/L via addition of ammonium sulfate ($(NH_4)_2SO_4$). Suitable additional nutrient sources, and their concentration in the fermentors, are listed in Table 9.

TABLE 9

| Component[1] | Initial concentration in fermentors |
|---|---|
| Lactose[2] | 10-20 |
| $KH_2PO_4$ | 3 |
| $MgSO_4 \cdot 7H_2O$ | 0.3 |
| $CaCl_2 \cdot 2H_2O$ | 0.4 |
| $FeSO_4 \cdot 7H_2O$ | 0.005 |
| $MnSO_4 \cdot H_2O$ | 0.002 |
| $ZnSO_4 \cdot H_2O$ | 0.0014 |
| Yeast extract | 0.16 |

[1]Note: elements may be partially or fully fulfilled by addition of the substrates (such as mash and DGS)
[2]Lactose is added primarily as an enzyme inducer Combine all nutrients in sterilized make-up process water and store for use.

Conduct fermentation in successive batch fermentors. Grow enzyme cultures of the microorganism in lab fermentors or flasks and transfer aseptically into pre-seed fermentors. The pre-seed and seed fermentors provide a 10% inoculum for the production fermentors. Each cycle of transfer and fermentation time may be about 144 hours. Carry out fermentation in fed-batch mode to achieve high enzyme protein concentration in the final broth under conditions of: 32±2° C., pH 4.5, air sparging rate of 0.5 vvm (volume of air per volume of broth per minute), over the course of 144 hours (including feeding and removal of fermentation broth). Once fermentation is complete, transfer the culture broth containing the active enzymatic mixture and store in enzyme storage tank(s) which are cooled (at less than approximately 25° C.) utilizing a chilled water jacket.

Example 5

This example provides a mass balance (Table 10) for an ethanol production process of the present invention prepared using corn stover and generally corresponding to the process depicted in FIG. 1.

TABLE 10

| | Milled & cleaned CS 1 | Dilute Acid 2 | Acidified CS 3 | Pretreatment steam 4 | Pretreatment flash steam 5 | PCS 6 | Reactants 7 | Conditioned PCS slurry 8 | Enzyme 9 | PCS feed to sugar extraction 10 | Wash water 11 |
|---|---|---|---|---|---|---|---|---|---|---|---|
| Component & Units | | | | | | | | | | | |
| Total Flow kg/hr | 46.30 | 48.38 | 94.68 | 27.46 | 13.61 | 106.06 | 16.17 | 122.23 | 0.95 | 123.18 | 80.83 |
| Dry total solids, kg/h | 41.67 | | | | | 40.42 | 1.62 | 42.03 | 0.07 | 42.11 | |
| Total Solids, wt fraction | 0.90 | | | | | 0.38 | 0.10 | 0.34 | 0.08 | 0.34 | |
| Moisture, wt fraction | 0.10 | | | | | 0.62 | 0.90 | 0.66 | 0.92 | 0.66 | |
| Insoluble, wt fraction | 1.00 | | | | | 0.65 | 0.36 | 0.64 | | 0.22 | |
| Soluble solids, wt fraction | 0.00 | | | | | 0.35 | 0.54 | 0.36 | | 0.12 | |
| Insoluble, kg/hr | | | | | | 26.27 | 0.58 | 26.85 | 0.07 | 26.93 | |
| Soluble solids, kg/hr | | | | | | 14.15 | 1.03 | 15.18 | | 15.18 | |
| Temperature ° C. | 20.0 | 60.0 | 60.0 | 192.0 | | 100.0 | 50.0 | 60.0 | 20.0 | 60.0 | 70.0 |
| pH | | | 1.10 | | | 1.80 | 4.50 | 4.50 | 4.50 | 4.50 | 6.80 |
| Pressure, psig | 14.7 | | | 175.0 | | | | | | | |
| Steam, kg/hr | | | | 27.46 | 13.61 | | | | | | |
| Water kg/hr | 4.63 | 47.44 | 52.07 | | | 65.64 | 14.55 | 80.19 | 0.88 | 81.07 | 80.83 |
| Ethanol kg/hr | | | | | | | | | | | |
| Glucose + oligomers (SS) kg/hr | | | | | | 1.78 | | | | | |
| Xylose + oligomers (SS) kg/hr | | | | | | 9.22 | | | | | |
| Arabinose + oligomers (SS) kg/hr | | | | | | 1.30 | | | | | |
| Non-glucose C6 Sugar + oligomers (SS) kg/hr | | | | | | 1.10 | | | | | |
| Lignin (SS) kg/hr | | | | | | 0.48 | | | | | |
| Inorganic Salts (SS) kg/hr | | | | | | 0.38 | | | | | |
| Volatile organics (acetic acid + furfural + HMF) kg/hr | | | | | | 1.02 | | | | | |
| Lactic Acid kg/hr | | | | | | | | | | | |
| Uronic Acid kg/hr | | | | | | 0.64 | | | | | |
| Ammonia (NH3) kg/hr | | | | | | | | | | | |
| NaOH kg/h | | | | | | | | | | | |
| Sulfuric acid kg/hr | | 0.94 | 0.94 | | | 0.94 | | | | | |
| Carbon Dioxide kg/hr | | | | | | | | | | | |
| Oxygen kg/hr | | | | | | | | | | | |
| Nitrogen kg/hr | | | | | | | | | | | |
| Starch (IS) kg/hr | | | | | | | | | | | |
| Glucan (IS) kg/hr | 16.08 | | 16.08 | | | 14.47 | | | | | |
| Xylan (IS) kg/hr | 9.02 | | 9.02 | | | 0.90 | | | | | |
| Arabinan (IS) kg/hr | 1.45 | | 1.45 | | | 0.30 | | | | | |
| Non-glucose C6 Solid (IS) kg/hr | 1.22 | | 1.22 | | | 0.23 | | | | | |
| Lignin (IS) kg/hr | 8.00 | | 8.00 | | | 7.52 | | | | | |
| Acetate (IS) kg/hr | 0.83 | | 0.83 | | | 0.04 | | | | | |
| Uronic Acid (IS) kg/hr | 1.29 | | 1.29 | | | 0.64 | | | | | |
| Ash (IS) kg/hr | 1.88 | | 1.88 | | | 1.50 | | | | | |
| Protein kg/hr | 1.50 | | 1.50 | | | | | | | 0.07 | |
| Yeast (IS) kg/h | | | | | | | | | | | |
| Enzyme (IS) kg/hr | | | | | | | | | | | |
| Unknown (IS) kg/hr | 0.40 | | 0.40 | | | 0.40 | | | | | |
| Unknown (SS) kg/hr | | | | | | | | | | | |
| Corn mash (35% TS), kg/hr | | | | | | | | | | | |
| 75% glucose syrup | | | | | | | | | | | |
| Nutrients, kg/hr | | | | | | | | | | | |

| | Sugar extract 12 | Sugar extract to xylose ferm 13 | Suplement 1 to xylose yeast prop 14 | Xylose yeast slurry 15 | Xylose yeast inoculum 16 | Wet cake from sugar extraction 17 | Caustic to lignin extraction 18 | Lignin extract 19 | Caustic insol fibers 20 |
|---|---|---|---|---|---|---|---|---|---|
| Component & Units | | 116.2 | | 0.31 | | | | | |
| Total Flow kg/hr | 118.49 | 14.40 | | 0.03 | 8.29 | 84.45 | 68.36 | 132.30 | 57.05 |
| Dry total solids, kg/h | 14.69 | 0.12 | | 0.10 | 0.37 | 27.34 | 0.68 | 6.78 | 19.97 |
| Total Solids, wt fraction | 0.12 | 0.88 | | 0.90 | 0.04 | 0.32 | 0.01 | 0.05 | 0.35 |
| Moisture, wt fraction | 0.88 | 0.00 | | 0.10 | 0.96 | 0.68 | 0.99 | 0.95 | 0.65 |
| Insoluble, wt fraction | 0.00 | 0.12 | | 0.00 | 0.01 | 0.32 | 0.00 | 0.00 | 0.35 |

TABLE 10-continued

| | | | | | | | | |
|---|---|---|---|---|---|---|---|---|
| Soluble solids, wt fraction | 0.12 | 0.26 | | 0.03 | 0.03 | 0.01 | 0.01 | 0.04 | 0.00 |
| Insoluble, kg/hr | 0.27 | 14.13 | | 0.00 | 0.10 | 26.58 | 0.00 | 0.27 | 19.95 |
| Soluble solids, kg/hr | 14.42 | 32.0 | | 40.0 | 0.27 | 0.76 | 0.68 | 5.70 | 0.01 |
| Temperature ° C. | 65.0 | 5.00 | | 6.80 | | 65.0 | 45.0 | 45.0 | 45.0 |
| pH | 2.50 | | | | | 3.70 | 13.00 | 12.00 | 8.00 |
| Pressure, psig | | | | | | | | | |
| Steam, kg/hr | | | | | | | | | |
| Water kg/hr | 103.80 | 101.72 | | 0.27 | 7.27 | 58.10 | 67.67 | 125.78 | 37.08 |
| Ethanol kg/hr | | | | | | | | | |
| Glucose + oligomers (SS) kg/hr | 1.70 | 1.66 | | | 0.03 | 0.09 | | 0.14 | |
| Xylose + oligomers (SS) kg/hr | 8.76 | 8.59 | | | 0.18 | 0.46 | | 0.18 | |
| Arabinose + oligomers (SS) kg/hr | 1.23 | 1.21 | | | 0.02 | 0.06 | | 0.06 | |
| Non-glucose C6 Sugar + oligomers (SS) kg/hr | 1.04 | 1.02 | | | 0.02 | 0.05 | | 0.05 | |
| Inorganic Salts (SS) kg/hr | 0.36 | 0.35 | | | 0.01 | 0.02 | | 0.02 | |
| Volatile organics (acetic acid + furfural + HMF) kg/hr | 0.96 | 0.95 | | | 0.02 | 0.05 | | 0.05 | |
| Lactic Acid kg/hr | | | | | | | | | |
| Uronic Acid kg/hr | 0.61 | 0.60 | | | 0.01 | 0.03 | | 0.03 | |
| Ammonia (NH3) kg/hr | | | | | | | | | |
| NaOH kg/h | | | | | | | 0.68 | | |
| Sulfuric acid kg/hr | 0.89 | | | | 0.06 | 0.05 | | 0.67 | 0.01 |
| Carbon Dioxide kg/hr | | | | | | | | 0.05 | |
| Oxygen kg/hr | | | | | | | | | |
| Nitrogen kg/hr | | | | | | | | | |
| Starch (IS) kg/hr | | | | | | | | | |
| Glucan (IS) kg/hr | | | | | | 14.47 | | | 14.32 |
| Xylan (IS) kg/hr | | | | | | 0.90 | | | 0.76 |
| Arabinan (IS) kg/hr | | | | | | 0.30 | | | 0.24 |
| Non-glucose C6 Solid (IS) kg/hr | | | | | | 0.23 | | | 0.18 |
| Lignin (IS) kg/hr | | | | | | 7.52 | | | 2.26 |
| Acetate (IS) kg/hr | | | | | | 0.04 | | | 0.04 |
| Uronic Acid (IS) kg/hr | | | | | | 0.64 | | | 0.64 |
| Ash (IS) kg/hr | | | | | | 1.50 | | | 1.50 |
| Protein kg/hr | | | | 0.03 | | | | | |
| Yeast (IS) kg/h | | | | | 0.10 | | | | |
| Enzyme (IS) kg/hr | | | | | | | | | |
| Unknown (IS) kg/hr | | | | | | | | | |
| Unknown (SS) kg/hr | | | | | | | | | |
| Corn mash (35% TS), kg/hr | | | | | | | | | |
| 75% glucose syrup | | | | | | | | | |
| Nutrients, kg/hr | | | | | | | | | |

| | Caustic insol fibers to enz pdn 21 | Caustic insol fibers to hyd 22 | Enz pdn supplement 23 | Crude enzyme 24 | Water to Enz Hyd 25 | Enz Hydrolysate 26 | C6 yeast suppl 27 | C6 dry yeast 28 | C6 yeast inoculum 29 |
|---|---|---|---|---|---|---|---|---|---|
| Component & Units | | | | | | | | | |
| Total Flow kg/hr | 0.57 | 56.48 | 2.59 | 2.81 | 42.36 | 112.21 | | | 5.61 |
| Dry total solids, kg/h | 0.20 | 19.77 | | 0.21 | | 29.06 | | 0.01 | 0.12 |
| Total Solids, wt fraction | 0.35 | 0.35 | | 0.07 | | 0.26 | | | 0.02 |
| Moisture, wt fraction | 0.65 | 0.65 | | 0.93 | | 0.74 | | | |
| Insoluble, wt fraction | 0.35 | 0.35 | | 0.07 | | 0.13 | | | |
| Soluble solids, wt fraction | 0.00 | | 0.00 | | | 0.13 | | | |
| Insoluble, kg/hr | 0.20 | 19.77 | | | | 14.26 | | | |
| Soluble solids, kg/hr | 0.00 | 0.01 | | | | 14.60 | | | |
| Ethanol Concentration, wt % | | | | | | | | | |
| Temperature ° C. | 45 | 45 | 35 | 35 | 45 | 45 | | | |
| pH | 8.0 | 8.0 | 5.0 | 5.0 | | | | | |
| Pressure, psig | | | | | | | | | |
| Steam | | | | | | | | | |
| Water kg/hr | | 36.71 | 1.49 | 2.59 | 42.36 | 83.15 | | | |
| Ethanol kg/hr | | | | | | | | | 5.49 |
| Glucose (SS) kg/hr | | | 0.35 | | | 13.51 | | | |
| Xylose (SS) kg/hr | | | | | | 0.81 | | | |
| Arabinose (SS) kg/hr | | | | | | 0.27 | | | |
| C6 Sugar (SS) kg/hr | | | | | | 0.20 | | | |
| Lignin (SS) kg/hr | | | | | | | | | |
| Inorganic Salts (SS) kg/hr | | | | | | | | | |
| Volatile organics (acetic acid + furfural + HMF) kg/hr | | | | | | | | | |
| Lactic Acid kg/hr | | | | | | | | | |
| Uronic Acid kg/hr | | | | | | | | | |
| Ammonia (NH3) kg/hr | | | | | | | | | |
| NaOH kg/h | | | | | | | | | |
| Sulfuric acid kg/hr | | | | | | | | | |
| Carbon Dioxide kg/hr | | | | | | | | | |
| Oxygen kg/hr | | | | | | | | | |
| Nitrogen kg/hr | | | | | | | | | |
| Starch (IS) kg/hr | | | | | | | | | |

TABLE 10-continued

| | | | |
|---|---|---|---|
| Glucan (IS) kg/hr | 14.32 | | 2.15 |
| Xylan (IS) kg/hr | 0.89 | | 0.18 |
| Arabinan (IS) kg/hr | 0.30 | | 0.30 |
| C6 Solid (IS) kg/hr | 0.23 | | 0.23 |
| Lignin (IS) kg/hr | 7.45 | | 7.45 |
| Acetate (IS) kg/hr | 0.04 | | 0.04 |
| Uronic Acid (IS) kg/hr | 0.64 | | 0.64 |
| Ash (IS) kg/hr | 1.49 | | 1.49 |
| Protein kg/hr | | 0.21 | 1.71 |
| Yeast (IS) kg/h | | | 0.01 0.08 |
| Enzyme (IS) kg/hr | | | |
| Unknown (IS) kg/hr | | | |
| Unknown (SS) kg/hr | | | |
| Corn mash (35% TS), kg/hr | | | |
| 75% glucose syrup | 0.47 | | 0.37 |
| Nutrients, kg/hr | 0.27 | 0.08 | 0.04 |

| | C5 beer 30 | C6 beer 31 | Distillation feed 32 | High-wine 33 | Whole stillage 34 | Solid residue 35 | Thin Stillage 36 | 93% sulfuric acid to lignin precipitate 37 | Lignin powder product 38 |
|---|---|---|---|---|---|---|---|---|---|
| Component & Units | | | | | | | | | |
| Total Flow kg/hr | 119.88 | 117.82 | 237.71 | 25.12 | 243.58 | 52.88 | 190.64 | 1.06 | 5.27 |
| Dry total solids, kg/h | 5.04 | 16.82 | 21.86 | | 20.57 | 18.51 | 2.06 | | 4.74 |
| Total Solids, wt fraction | 0.04 | 0.14 | 0.09 | | 0.08 | 0.35 | 0.01 | | 0.90 |
| Moisture, wt fraction | | | | | | | | | |
| Insoluble, wt fraction | | | | | | | | | |
| Soluble solids, wt fraction | | | | | | | | | |
| Insoluble, kg/hr | | | | | | | | | |
| Soluble solids, kg/hr | | | | | | | | | |
| Ethanol Concentration, wt % | 3.80 | 6.63 | 0.05 | 42.00 | 0.00 | | | | |
| Temperature ° C. | 35 | 37 | 36 | 50 | 90 | | | | |
| pH | 4.5 | 4.5 | 4.5 | | 4.5 | | | | |
| Pressure, psig | | | | | | | | | |
| Steam | | | | | | | | | |
| Water kg/hr | 108.99 | 88.64 | 197.63 | 14.57 | 222.96 | 34.37 | 188.58 | 0.07 | |
| Ethanol kg/hr | 4.31 | 6.29 | 10.60 | 10.55 | 0.05 | | | | |
| Glucose (SS) kg/hr | 0.42 | 1.35 | 1.77 | | 1.77 | | | | |
| Xylose (SS) kg/hr | 2.15 | 0.81 | 2.96 | | 2.96 | | | | |
| Arabinose (SS) kg/hr | 1.21 | 0.27 | 1.48 | | 1.48 | | | | |
| C6 Sugar (SS) kg/hr | 0.25 | 0.02 | | | | | | | |
| Lignin (SS) kg/hr | 0.45 | | | | | | | | |
| Inorganic Salts (SS) kg/hr | 0.35 | | | | | | | | |
| Volatile organics (acetic acid + furfural + HMF) kg/hr | 0.95 | | | | | | | | |
| Lactic Acid kg/hr | | | | | | | | | |
| Uronic Acid kg/hr | | | | | | | | | |
| Ammonia (NH3) kg/hr | 0.60 | | | | | | | | |
| NaOH kg/h | | | | | | | | | |
| Sulfuric acid kg/hr | | | | | | | | 0.98 | |
| Carbon Dioxide kg/hr | | | | | | | | | |
| Oxygen kg/hr | | | | | | | | | |
| Nitrogen kg/hr | | | | | | | | | |
| Starch (IS) kg/hr | | | | | | | | | |
| Glucan (IS) kg/hr | | 2.15 | | | 2.15 | | | | |
| Xylan (IS) kg/hr | | 0.18 | | | 0.18 | | | | |
| Arabinan (IS) kg/hr | | 0.30 | | | 0.30 | | | | |
| C6 Solid (IS) kg/hr | | 0.23 | | | 0.23 | | | | |
| Lignin (IS) kg/hr | | 7.45 | | | 7.45 | | | 4.74 | |
| Acetate (IS) kg/hr | | 0.04 | | | 0.04 | | | | |
| Uronic Acid (IS) kg/hr | | 0.64 | | | 0.64 | | | | |
| Ash (IS) kg/hr | | 1.49 | | | 1.49 | | | | |
| Protein kg/hr | | 1.71 | | | 1.71 | | | | |
| Yeast (IS) kg/h | 0.22 | 0.18 | | | 0.18 | | | | |
| Enzyme (IS) kg/hr | | | | | | | | | |
| Unknown (IS) kg/hr | | | | | | | | | |
| Unknown (SS) kg/hr | | | | | | | | | |
| Corn mash (35% TS), kg/hr | | | | | | | | | |
| 75% glucose syrup | | | | | | | | | |
| Nutrients, kg/hr | | | | | | | | | |

| | Lignin filtrate 39 | Lignin slurry product (alternate) 40 | Distillation steam 41 |
|---|---|---|---|
| Component & Units | | | |
| Total Flow kg/hr | 152.13 | 17.56 | 39.90 |
| Dry total solids, kg/h | 2.83 | 5.27 | |

TABLE 10-continued

| | | |
|---|---|---|
| Total Solids, wt fraction | 0.02 | 0.30 |
| Moisture, wt fraction | | |
| Insoluble, wt fraction | | |
| Soluble solids, wt fraction | | |
| Insoluble, kg/hr | | |
| Soluble solids, kg/hr | | |
| Ethanol Concentration, wt % | | |
| Temperature ° C. | | 160 |
| pH | | |
| Pressure, psig | | 75.0 |
| Steam | | 39.90 |
| Water kg/hr | | |
| Ethanol kg/hr | | |
| Glucose (SS) kg/hr | | |
| Xylose (SS) kg/hr | | |
| Arabinose (SS) kg/hr | | |
| C6 Sugar (SS) kg/hr | | |
| Lignin (SS) kg/hr | | |
| Inorganic Salts (SS) kg/hr | | |
| Volatile organics (acetic acid + furfural + HMF) kg/hr | | |
| Lactic Acid kg/hr | | |
| Uronic Acid kg/hr | | |
| Ammonia (NH3) kg/hr | | |
| NaOH kg/h | | |
| Sulfuric acid kg/hr | | |
| Carbon Dioxide kg/hr | | |
| Oxygen kg/hr | | |
| Nitrogen kg/hr | | |
| Starch (IS) kg/hr | | |
| Glucan (IS) kg/hr | | |
| Xylan (IS) kg/hr | | |
| Arabinan (IS) kg/hr | | |
| C6 Solid (IS) kg/hr | | |
| Lignin (IS) kg/hr | | |
| Acetate (IS) kg/hr | | |
| Uronic Acid (IS) kg/hr | | |
| Ash (IS) kg/hr | | |
| Protein kg/hr | | |
| Yeast (IS) kg/h | | |
| Enzyme (IS) kg/hr | | |
| Unknown (IS) kg/hr | | |
| Unknown (SS) kg/hr | | |
| Corn mash (35% TS), kg/hr | | |
| 75% glucose syrup | | |
| Nutrients, kg/hr | | |

Example 6

This example provides a mass balance (Table 11) for an ethanol production process of the present invention prepared using corn stover and generally corresponding to the process depicted in FIG. 3.

TABLE 11

| | Milled & cleaned CS 1 | Dilute Acid 2 | Acidified CS 3 | Pretreatment steam 4 | Pretreatment flash steam 5 | PCS 6 | Reactants 7 | Conditioned PCS slurry 8 | Enzyme 9 |
|---|---|---|---|---|---|---|---|---|---|
| Component & Units | | | | | | | | | |
| Total Flow kg/hr | 46.30 | 48.38 | 94.68 | 27.46 | 13.61 | 106.06 | 16.17 | 122.23 | 0.95 |
| Dry total solids, kg/h | 41.67 | | | | | 40.42 | 1.62 | 42.03 | 0.07 |
| Total Solids, wt fraction | 0.90 | | | | | 0.38 | 0.10 | 0.34 | 0.08 |
| Moisture, wt fraction | 0.10 | | | | | 0.62 | 0.90 | 0.66 | 0.92 |
| Insoluble, wt fraction | 1.00 | | | | | 0.65 | 0.36 | 0.64 | |
| Soluble solids, wt fraction | 0.00 | | | | | 0.35 | 0.54 | 0.36 | |
| Insoluble, kg/hr | | | | | | 26.27 | 0.58 | 26.85 | 0.07 |
| Soluble solids, kg/hr | | | | | | 14.15 | 1.03 | 15.18 | |
| Temperature ° C. | 20 | 60 | 60 | 192 | | 100 | 50 | 60 | 20 |
| pH | | | 1.1 | | | 1.8 | 4.5 | 4.5 | 4.5 |
| Pressure, psig | 14.7 | | | 175.0 | | | | | |
| Steam, kg/hr | | | | 27.46 | 13.61 | | | | |
| Water kg/hr | 4.63 | 47.44 | 52.07 | | | 65.64 | 14.55 | 80.19 | 0.88 |
| Ethanol kg/hr | | | | | | | | | |
| Glucose + oligomers (SS) kg/hr | | | | | | 1.78 | | | |

TABLE 11-continued

| | | | | |
|---|---|---|---|---|
| Xylose + oligomers (SS) kg/hr | | | | 9.22 |
| Arabinose + oligomers (SS) kg/hr | | | | 1.30 |
| Non-glucose C6 Sugar + oligomers (SS) kg/hr | | | | 1.10 |
| Lignin (SS) kg/hr | | | | 0.48 |
| Inorganic Salts (SS) kg/hr | | | | 0.38 |
| Volatile organics (acetic acid + furfural + HMF) kg/hr | | | | 1.02 |
| Lactic Acid kg/hr | | | | |
| Uronic Acid kg/hr | | | | 0.64 |
| Ammonia (NH3) kg/hr | | | | |
| NaOH kg/h | | | | |
| Sulfuric acid kg/hr | | 0.94 | 0.94 | 0.94 |
| Carbon Dioxide kg/hr | | | | |
| Oxygen kg/hr | | | | |
| Nitrogen kg/hr | | | | |
| Starch (IS) kg/hr | | | | |
| Glucan (IS) kg/hr | 16.08 | | 16.08 | 14.47 |
| Xylan (IS) kg/hr | 9.02 | | 9.02 | 0.90 |
| Arabinan (IS) kg/hr | 1.45 | | 1.45 | 0.30 |
| Non-glucose C6 Solid (IS) kg/hr | 1.22 | | 1.22 | 0.23 |
| Lignin (IS) kg/hr | 8.00 | | 8.00 | 7.52 |
| Acetate (IS) kg/hr | 0.83 | | 0.83 | 0.04 |
| Uronic Acid (IS) kg/hr | 1.29 | | 1.29 | 0.64 |
| Ash (IS) kg/hr | 1.88 | | 1.88 | 1.50 |
| Protein kg/hr | 1.50 | | 1.50 | | 0.07 |
| Yeast (IS) kg/h | | | | |
| Enzyme (IS) kg/hr | | | | |
| Unknown (IS) kg/hr | 0.40 | | 0.40 | 0.40 |
| Unknown (SS) kg/hr | | | | |
| Corn mash (35% TS), kg/hr | | | | |
| 75% glucose syrup | | | | |
| Nutrients, kg/hr | | | | |

| | PCS feed to sugar extraction 10 | Wash water 11 | Sugar extract 12 | Sugar extract to xylose ferm 13 | Suplement 1 to xylose yeast prop 14 | Xylose yeast slurry 15 | Xylose yeast inoculum 16 | Washed fibers from sugar extraction 17 | Washed fibers to enz production 18 |
|---|---|---|---|---|---|---|---|---|---|
| Component & Units | | | | | | | | | |
| Total Flow kg/hr | 123.18 | 80.83 | 118.49 | 116.12 | 0.31 | 8.29 | | 85.45 | 0.85 |
| Dry total solids, kg/h | 42.11 | | 14.69 | 14.40 | 0.03 | 0.37 | | 27.34 | 0.27 |
| Total Solids, wt fraction | 0.34 | | 0.12 | 0.12 | 0.10 | 0.04 | | 0.32 | 0.32 |
| Moisture, wt fraction | 0.66 | | 0.88 | 0.88 | 0.90 | 0.96 | | 0.68 | 0.68 |
| Insoluble, wt fraction | 0.22 | | 0.00 | 0.00 | 0.10 | 0.01 | | 0.31 | 0.32 |
| Soluble solids, wt fraction | 0.12 | | 0.12 | 0.12 | 0.00 | 0.03 | | 0.01 | 0.00 |
| Insoluble, kg/hr | 26.93 | | 0.27 | 0.26 | 0.03 | 0.10 | | 26.58 | 0.27 |
| Soluble solids, kg/hr | 15.18 | | 14.42 | 14.13 | 0.00 | 0.27 | | 0.76 | 0.00 |
| Temperature ° C. | 60 | 70 | 65 | 32 | | 40 | | 65 | 45 |
| pH | 4.5 | 6.8 | 2.5 | 5.0 | | 6.8 | | 3.7 | 3.7 |
| Pressure, psig | | | | | | | | | |
| Steam, kg/hr | | | | | | | | | |
| Water kg/hr | 81.07 | 80.83 | 103.80 | 101.72 | 0.27 | 7.27 | | 58.10 | 0.58 |
| Ethanol kg/hr | | | | | | | | | |
| Glucose + oligomers (SS) kg/hr | | | 1.70 | 1.66 | | 0.03 | | | |
| Xylose + oligomers (SS) kg/hr | | | 8.76 | 8.59 | | 0.18 | | | |
| Arabinose + oligomers (SS) kg/hr | | | 1.23 | 1.21 | | 0.02 | | | |
| Non-glucose C6 Sugar + oligomers (SS) kg/hr | | | 1.04 | 1.02 | | 0.02 | | | |
| Lignin (SS) kg/hr | | | 0.46 | 0.45 | | 0.01 | | | |
| Inorganic Salts (SS) kg/hr | | | 0.36 | 0.35 | | 0.01 | | | |
| Volatile organics (acetic acid + furfural + HMF) kg/hr | | | 0.96 | 0.95 | | 0.02 | | | |
| Lactic Acid kg/hr | | | | | | | | | |
| Uronic Acid kg/hr | | | 0.61 | 0.60 | | 0.01 | | | |
| Ammonia (NH3) kg/hr | | | | | | | | | |
| NaOH kg/h | | | | | | | | | |
| Sulfuric acid kg/hr | | | 0.89 | | | 0.06 | | | |
| Carbon Dioxide kg/hr | | | | | | | | | |
| Oxygen kg/hr | | | | | | | | | |
| Nitrogen kg/hr | | | | | | | | | |
| Starch (IS) kg/hr | | | | | | | | 14.47 | 0.14 |
| Glucan (IS) kg/hr | | | | | | | | 0.90 | 0.01 |
| Xylan (IS) kg/hr | | | | | | | | 0.30 | 0.00 |
| Arabinan (IS) kg/hr | | | | | | | | 0.23 | 0.00 |
| Non-glucose C6 Solid (IS) kg/hr | | | | | | | | 7.52 | 0.08 |
| Lignin (IS) kg/hr | | | | | | | | 0.04 | 0.00 |
| Acetate (IS) kg/hr | | | | | | | | 0.64 | 0.01 |

TABLE 11-continued

| | | |
|---|---|---|
| Uronic Acid (IS) kg/hr | 1.50 | 0.02 |
| Ash (IS) kg/hr | | |
| Protein kg/hr | 0.10 | |
| Yeast (IS) kg/h | 0.03 | |
| Enzyme (IS) kg/hr | | |
| Unknown (IS) kg/hr | | |
| Unknown (SS) kg/hr | | |
| Corn mash (35% TS), kg/hr | | |
| 75% glucose syrup | | |
| Nutrients, kg/hr | | |

| | Washed fibers to enz hydrolysis 19 | Enz pdn supplement 20 |
|---|---|---|
| Component & Units | | |
| Total Flow kg/hr | 84.59 | 2.59 |
| Dry total solids, kg/h | 27.07 | |
| Total Solids, wt fraction | 0.32 | |
| Moisture, wt fraction | 0.68 | |
| Insoluble, wt fraction | 0.31 | |
| Soluble solids, wt fraction | 0.01 | |
| Insoluble, kg/hr | 26.31 | |
| Soluble solids, kg/hr | 0.76 | |
| Temperature ° C. | 45 | 35 |
| pH | 3.7 | 5.0 |
| Pressure, psig | | |
| Steam, kg/hr | | |
| Water kg/hr | 58.69 | 1.49 |
| Ethanol kg/hr | | |
| Glucose + oligomers (SS) kg/hr | 0.09 | 0.35 |
| Xylose + oligomers (SS) kg/hr | 0.46 | |
| Arabinose + oligomers (SS) kg/hr | 0.06 | |
| Non-glucose C6 Sugar + oligomers (SS) kg/hr | 0.05 | |
| Lignin (SS) kg/hr | 0.02 | |
| Inorganic Salts (SS) kg/hr | 0.02 | |
| Volatile organics (acetic acid + furfural + HMF) kg/hr | 0.05 | |
| Lactic Acid kg/hr | | |
| Uronic Acid kg/hr | 0.03 | |
| Ammonia (NH3) kg/hr | | |
| NaOH kg/h | | |
| Sulfuric acid kg/hr | 0.05 | |
| Carbon Dioxide kg/hr | | |
| Oxygen kg/hr | | |
| Nitrogen kg/hr | 14.32 | |
| Starch (IS) kg/hr | 0.89 | |
| Glucan (IS) kg/hr | 0.30 | |
| Xylan (IS) kg/hr | 0.23 | |
| Arabinan (IS) kg/hr | 7.45 | |
| Non-glucose C6 Solid (IS) kg/hr | 0.04 | |
| Lignin (IS) kg/hr | 0.64 | |
| Acetate (IS) kg/hr | 1.49 | |
| Uronic Acid (IS) kg/hr | | |
| Ash (IS) kg/hr | | |
| Protein kg/hr | | |
| Yeast (IS) kg/hr | | |
| Enzyme (IS) kg/hr | | |
| Unknown (IS) kg/hr | | |
| Unknown (SS) kg/hr | | |
| Corn mash (35% TS), kg/hr | | |
| 75% glucose syrup | | 0.47 |
| Nutrients, kg/hr | | 0.27 |

| | Crude enzyme 21 | Water to enz hydrolysis 22 | Enzyme Hydrolysate 23 | C6 yeast suppl 24 | C6 dry yeast 25 | C6 yeast inoculum 26 | C5 beer 27 | C6 beer 28 | Distillation feed 29 |
|---|---|---|---|---|---|---|---|---|---|
| Component & Units | | | | | | | | | |
| Total Flow kg/hr | 2.81 | 50.76 | 141.28 | 2.81 | 0.00 | 7.06 | 119.88 | 148.34 | 268.23 |
| Dry total solids, kg/h | 0.21 | | 29.25 | 0.21 | 0.07 | 1.20 | 5.04 | 17.76 | 22.80 |
| Total Solids, wt fraction | 0.07 | | 0.21 | 0.07 | | 0.17 | 0.04 | 0.12 | 0.08 |
| Moisture, wt fraction | 0.93 | | 0.79 | 0.93 | | 0.83 | 0.96 | 0.88 | 0.92 |
| Insoluble, wt fraction | 0.07 | | 0.10 | 0.07 | | 0.17 | 0.00 | 0.11 | 0.06 |
| Soluble solids, wt fraction | | | 0.10 | | | 0.00 | | | 0.02 |
| Insoluble, kg/hr | | | 14.45 | | | 1.20 | 0.22 | 16.65 | 16.87 |
| Soluble solids, kg/hr | | | 14.60 | | | 0.00 | 4.82 | 1.10 | 5.93 |
| Ethanol Concentration, wt % | | | | | | | 3.80 | 5.07 | 4.47 |
| Temperature ° C. | 35 | 45 | 45 | 35 | 45 | 45 | 35 | 35 | 35 |

TABLE 11-continued

|  |  |  |  |  |  |  |  |  |
|---|---|---|---|---|---|---|---|---|
| pH | 5.0 | 7.0 | 4.5 | 5.0 |  | 4.5 | 4.5 | 4.5 | 4.5 |
| Pressure, psig |  |  |  |  |  |  |  |  |
| Steam |  |  |  |  |  |  |  |  |
| Water kg/hr | 2.59 | 50.76 | 112.03 | 2.59 |  | 5.86 | 108.99 | 117.89 | 226.88 |
| Ethanol kg/hr |  |  |  |  |  |  | 4.31 | 6.29 | 10.60 |
| Glucose (SS) kg/hr |  |  | 13.51 |  |  |  | 0.42 | 1.35 | 1.77 |
| Xylose (SS) kg/hr |  |  | 0.81 |  |  |  | 2.15 | 0.81 | 2.96 |
| Arabinose (SS) kg/hr |  |  | 0.27 |  |  |  | 1.21 | 0.27 | 1.48 |
| C6 Sugar (SS) kg/hr |  |  | 0.20 |  |  |  | 0.25 | 0.02 | 0.27 |
| Lignin (SS) kg/hr |  |  |  |  |  |  | 0.45 |  | 0.45 |
| Inorganic Salts (SS) kg/hr |  |  |  |  |  |  | 0.35 |  | 0.35 |
| Volatile organics (acetic acid + furfural + HMF) kg/hr |  |  |  |  |  |  | 0.95 |  | 0.95 |
| Lactic Acid kg/hr |  |  |  |  |  |  |  |  |  |
| Uronic Acid kg/hr |  |  |  |  |  |  | 0.60 |  | 0.60 |
| Ammonia (NH3) kg/hr |  |  |  |  |  |  |  |  |  |
| NaOH kg/h |  |  |  |  |  |  |  |  |  |
| Sulfuric acid kg/hr |  |  |  |  |  |  |  |  |  |
| Carbon Dioxide kg/hr |  |  |  |  |  |  |  |  |  |
| Oxygen kg/hr |  |  |  |  |  |  |  |  |  |
| Nitrogen kg/hr |  |  |  |  |  |  |  |  |  |
| Starch (IS) kg/hr |  |  |  |  |  |  |  |  |  |
| Glucan (IS) kg/hr |  |  | 2.15 |  |  |  |  | 2.15 | 2.15 |
| Xylan (IS) kg/hr |  |  | 0.18 |  |  |  |  | 0.18 | 0.18 |
| Arabinan (IS) kg/hr |  |  | 0.30 |  |  |  |  | 0.30 | 0.30 |
| C6 Solid (IS) kg/hr |  |  | 0.23 |  |  |  |  | 0.23 | 0.23 |
| Lignin (IS) kg/hr |  |  | 7.45 |  |  |  |  | 7.45 | 7.45 |
| Acetate (IS) kg/hr |  |  | 0.04 |  |  |  |  | 0.04 | 0.04 |
| Uronic Acid (IS) kg/hr |  |  | 0.64 |  |  |  |  | 0.64 | 0.64 |
| Ash (IS) kg/hr |  |  | 1.49 |  |  |  |  | 1.49 | 1.49 |
| Protein kg/hr | 0.21 |  | 1.71 | 0.21 |  |  |  | 1.71 | 1.71 |
| Yeast (IS) kg/h |  |  |  |  |  | 0.07 | 1.12 | 0.22 | 1.12 | 1.12 |
| Enzyme (IS) kg/hr |  |  |  |  |  |  |  |  |  |
| Unknown (IS) kg/hr |  |  |  |  |  |  |  |  |  |
| Unknown (SS) kg/hr |  |  |  |  |  |  |  |  |  |
| Corn mash (35% TS), kg/hr |  |  |  |  |  |  |  |  |  |
| 75% glucose syrup |  |  |  |  |  |  |  |  |  |
| Nutrients, kg/hr |  |  | 0.27 |  |  | 0.08 |  |  | .56 |

|  | Whole stillage 30 | High-wine 31 | Stillage cake 32 | Thin stillage 33 | Caustic to lignin extraction 34 | Lignin extract 35 | 93% sulfuric acid to lignin precipitate 36 | Lignin powder product 37 | Lignin filtrate to wastewater 38 |
|---|---|---|---|---|---|---|---|---|---|
| Component & Units |  |  |  |  |  |  |  |  |  |
| Total Flow kg/hr | 280.19 | 25.12 | 305.31 | 223.16 | 128.55 | 154.46 | 1.20 | 7.30 | 177.38 |
| Dry total solids, kg/h | 22.80 |  | 16.95 | 5.85 | 0.80 | 8.74 |  | 6.94 | 2.39 |
| Total Solids, wt fraction | 0.08 |  | 0.06 | 0.03 | 0.01 | 0.06 |  | 0.95 | 0.01 |
| Moisture, wt fraction | 0.92 |  | 0.94 | 0.97 |  |  |  | 0.05 |  |
| Insoluble, wt fraction | 0.06 |  | 0.95 | 0.14 |  |  |  | 0.98 |  |
| Soluble solids, wt fraction | 0.02 |  | 0.05 | 0.86 |  |  |  | 0.02 |  |
| Insoluble, kg/hr | 16.87 |  | 16.03 | 0.84 |  |  |  | 6.83 |  |
| Soluble solids, kg/hr | 5.93 |  | 0.92 | 5.00 |  | 8.74 |  | 0.11 |  |
| Ethanol Concentration, wt % | 0.02 | 42.00 | 0.02 | 0.02 |  |  |  |  |  |
| Temperature ° C. | 35 | 50 | 90 | 90 | 20 | 50 |  | 25 |  |
| pH | 4.5 |  | 4.5 | 4.5 | 13.0 | 12.0 |  | 3.0 |  |
| Pressure, psig |  |  |  |  |  |  |  |  |  |
| Steam |  |  |  |  |  |  |  |  |  |
| Water kg/hr | 257.34 | 14.57 | 40.07 | 217.32 | 127.75 | 145.72 | 0.08 |  | 174.98 |
| Ethanol kg/hr | 0.05 | 10.55 | 0.01 | 0.04 |  |  |  |  |  |
| Glucose (SS) kg/hr | 1.77 |  |  |  |  |  |  |  |  |
| Xylose (SS) kg/hr | 2.15 |  |  |  |  |  |  |  |  |
| Arabinose (SS) kg/hr | 0.30 |  |  |  |  |  |  |  |  |
| C6 Sugar (SS) kg/hr | 0.25 |  |  |  |  |  |  |  | 0.79 |
| Lignin (SS) kg/hr | 0.11 |  |  |  |  | 6.33 |  |  | 0.32 |
| Inorganic Salts (SS) kg/hr | 0.09 |  |  |  |  |  |  |  | 1.28 |
| Volatile organics (acetic acid + furfural + HMF) | 0.24 |  |  |  |  |  |  |  |  |
| Lactic Acid kg/hr |  |  |  |  |  |  |  |  |  |
| Uronic Acid kg/hr | 0.15 |  |  |  |  |  |  |  |  |
| Ammonia (NH3) kg/hr |  |  |  |  | 0.80 | 0.76 | 1.12 |  |  |
| NaOH kg/h |  |  |  |  |  |  |  |  |  |
| Sulfuric acid kg/hr |  |  |  |  |  |  |  |  |  |
| Carbon Dioxide kg/hr |  |  |  |  |  |  |  |  |  |
| Oxygen kg/hr |  |  |  |  |  |  |  |  |  |
| Nitrogen kg/hr |  |  |  |  |  |  |  |  |  |
| Starch (IS) kg/hr |  |  |  |  |  |  |  |  |  |
| Glucan (IS) kg/hr | 2.15 |  |  |  |  |  |  |  | 0.86 |
| Xylan (IS) kg/hr | 0.18 |  |  |  |  |  |  |  |  |
| Arabinan (IS) kg/hr | 0.30 |  |  |  |  |  |  |  |  |

TABLE 11-continued

| | | |
|---|---|---|
| C6 Solid (IS) kg/hr | 0.23 | |
| Lignin (IS) kg/hr | 7.45 | 6.33 |
| Acetate (IS) kg/hr | 0.04 | |
| Uronic Acid (IS) kg/hr | 0.64 | |
| Ash (IS) kg/hr | 1.49 | |
| Protein kg/hr | 1.71 | |
| Yeast (IS) kg/h | 1.12 | |
| Enzyme (IS) kg/hr | | |
| Unknown (IS) kg/hr | | |
| Unknown (SS) kg/hr | | |
| Corn mash (35% TS), kg/hr | | |
| 75% glucose syrup | | |
| Nutrients, kg/hr | | |

| | Lignin slurry product (alternate) 39 | Residue 40 | Distillation steam 41 |
|---|---|---|---|
| Component & Units | | | |
| Total Flow kg/hr | 29.13 | 31.11 | 45.02 |
| Dry total solids, kg/h | 8.74 | 9.01 | |
| Total Solids, wt fraction | 0.30 | 0.30 | |
| Moisture, wt fraction | | | |
| Insoluble, wt fraction | | | |
| Soluble solids, wt fraction | | | |
| Insoluble, kg/hr | | 8.84 | |
| Soluble solids, kg/hr | 8.74 | 0.13 | |
| Ethanol Concentration, wt % | | | |
| Temperature ° C. | | | 160 |
| pH | 12.0 | | |
| Pressure, psig | | | 75.0 |
| Steam | | | 45.02 |
| Water kg/hr | | | |
| Ethanol kg/hr | | | |
| Glucose (SS) kg/hr | | | |
| Xylose (SS) kg/hr | | | |
| Arabinose (SS) kg/hr | | | |
| C6 Sugar (SS) kg/hr | | | |
| Lignin (SS) kg/hr | | | |
| Inorganic Salts (SS) kg/hr | | | |
| Volatile organics (acetic acid + furfural + HMF) kg/hr | | | |
| Lactic Acid kg/hr | | | |
| Uronic Acid kg/hr | | | |
| Ammonia (NH3) kg/hr | | | |
| NaOH kg/h | | 0.04 | |
| Sulfuric acid kg/hr | | | |
| Carbon Dioxide kg/hr | | | |
| Oxygen kg/hr | | | |
| Nitrogen kg/hr | | | |
| Starch (IS) kg/hr | | | |
| Glucan (IS) kg/hr | | | |
| Xylan (IS) kg/hr | | | |
| Arabinan (IS) kg/hr | | | |
| C6 Solid (IS) kg/hr | | | |
| Lignin (IS) kg/hr | | | |
| Acetate (IS) kg/hr | | | |
| Uronic Acid (IS) kg/hr | | | |
| Ash (IS) kg/hr | | | |
| Protein kg/hr | | | |
| Yeast (IS) kg/h | | | |
| Enzyme (IS) kg/hr | | | |
| Unknown (IS) kg/hr | | | |
| Unknown (SS) kg/hr | | | |
| Corn mash (35% TS), kg/hr | | | |
| 75% glucose syrup | | | |
| Nutrients, kg/hr | | | |

Example 7

This example demonstrates the relationship between particle size and ash content of milled dried corn stover.

A 30 g sample of 1.25 inch roto-chopped corn stover was dried in a convection oven at 45° C. under atmospheric pressure (760 mm Hg absolute; 101.3 kPa) over 20 hours. After 20 hours, the chopped corn stover was weighed.

Then the chopped corn stover was milled in a kinematic knife mill equipped with a 2 mm outlet screen. The milled corn stover particles passing through the 2 mm screen were classified in a Tyler sieve shaker containing a 20 Mesh screen (840 μm) and a 100 Mesh screen (150 μm).

Approximately 2.0 g samples of each corn stover fraction (i.e., the 1.25-inch roto-chopped, 2 mm, >20 mesh, >100 mesh to <20 mesh, and <100 mesh fraction) were placed in a crucible, and heated in a muffle furnace equipped with a thermostat, set to 575 (±25° C.) for 22 hours. After 22 hours the weight of each sample was measured, which represents the total ash content of the dried corn stover samples.

Table 12 shows the total ash content of the dried corn stover fractions. The results show that the <100 Mesh fraction has over 80 wt % ash and the >20 Mesh fraction has the lowest percentage of ash at about 6.5 wt %.

TABLE 12

| Sample | Experiment 1 (wt %) | Experiment 2 (wt %) | Average (wt %) |
|---|---|---|---|
| 1.25-inch roto-chopped | 7.91 | 9.60 | 8.75 |
| 2 mm | 17.51 | 16.60 | 17.05 |
| >20 mesh | 6.55 | 5.86 | 6.21 |
| >100 mesh to <20 mesh | 24.77 | 25.63 | 25.20 |
| <100 mesh | 81.98 | 81.55 | 81.76 |

Example 8

The example describes Protocol A for determining the acid neutralization capacity of a biomass feedstock and fractions thereof (e.g., fine particulate fractions and cleaned biomass feedstocks).

Step 1: Determine the dry weight ($W_s$) of the biomass sample.

To determine the dry weight of the biomass sample, place a 30 g sample in a convection oven at 105° C. under atmospheric pressure (760 mm Hg absolute; 101.3 kPa) until constant weight is achieved (i.e., change in weight is less than +/−1 wt % upon reheating) and then weigh the sample.

Step 2: Determine $pH_{initial}$ of a standard acid sulfuric acid solution.

In a 1000 ml beaker place 500 ml of a standard sulfuric acid solution (e.g., 0.01N, 0.02N, or 0.05N solution). Measure the pH value of the standard sulfuric acid solution using a calibrated pH meter.

Step 3: Determine $pH_{final}$ of the slurry

Add the 30 g (dry weight) of the biomass sample to the standard sulfuric acid solution in the 1000 ml beaker. Place the beaker with a magnetic agitator in a water bath at 25° C., and stir at 330 revolutions per minute (rpm) for 30 minutes. After the 30 minutes, measure the pH value of the slurry with the calibrated pH meter.

Step 4: Calculate the acid neutralizing capacity

Acid neutralizing capacity (ANC: g/g) of the sample is calculated according to the following equation:

$$ANC = [H^+](\text{neutralized}) \times V \times MW \times MR \times 1/W_s$$

wherein, $[H^+](\text{neutralized}) = (10^{-pH_{initial}} - 10^{-pH_{final}})$ (mol/L)

V = total volume of slurry (L)

MW = molecular weight of sulfuric acid (i.e., 98 g/mol)

MR = mole ratio of sulfuric acid to hydrogen ion (i.e., 1/2)

$W_s$ = dry weight of sample (g)

Example 9

This example compares the acid neutralization capacity as determined in accordance with Protocol A for three corn stover samples, including the effects of screening the milled corn stover using a screen having openings of a size of about U.S. Sieve No. 60 (250 µm). Table 13 provides the ash content and acid neutralization capacity for the fractions tested.

TABLE 13

| Dry, Milled Corn Stover | Sample 1 | Sample 2 | Sample 3 |
|---|---|---|---|
| Approximate Weight (g) | 100 | 100 | 100 |
| Ash content (wt %) | 5.4 | 9.0 | 11.0 |
| Acid Neutralization Capacity (g sulfuric acid/g dry matter) | 0.0054 | 0.0108 | 0.0148 |
| Screened & Milled Corn Stover (g) | 96.6 | 95.4 | 93.9 |
| Ash Content of Screened & Milled Corn Stover (wt %) | 4.0 | 7.0 | 7.8 |
| Acid Neutralization Capacity of Screened & Milled Corn Stover (g sulfuric acid/g dry matter) | 0.0038 | 0.0080 | 0.0107 |
| Fines (g) | 3.4 | 4.7 | 6.1 |
| Ash Content of Fines (wt %) | 45.0 | 50.0 | 60.0 |
| Acid Neutralization Capacity of Fines (g sulfuric acid/g dry matter) | 0.0093 | 0.0140 | 0.0206 |

Example 10

Protocol B for determining the xylose content of a biomass feedstock, pretreated biomass feedstock, and fractions thereof, which is necessary for determining xylose yield (based on the hemicellulose content of the biomass feedstock) is the method described in the National Renewable Energy Laboratory (NREL) Technical Report NREL/TP-510-42623, January 2008, which is entitled "Determination of Sugars, Byproducts, and Degradation Products in Liquid Fraction Process Samples," Laboratory Analytical Procedure (LAP), Issue Date: Dec. 8, 2006, by A. Sluiter, B. Hames, R. Ruiz, C. Scarlata, J. Sluiter, and D. Templeton. The entire contents of this report are hereby incorporated herein by reference for all relevant purposes.

Example 11

This example describes Protocol C for determining the cellulose digestibility of a biomass feedstock, pretreated biomass feedstock, and fractions thereof.

This protocol describes the enzymatic saccharification of cellulose from native or pretreated lignocellulosic biomass to glucose in order to determine the maximum extent of digestibility possible. This protocol covers the determination of the maximum extent of digestibility of lignocellulosic biomass. If the biomass is suspected to have some starch content, the dry weight percent cellulose calculated from total glucan must be corrected to subtract the starch contribution to total dry weight percent glucose.

Samples should be washed to remove any free acid or alkali prior to conducting this protocol.

1. Sampling and Test Specimens

The test specimen consists of about 1 gram of 6 wt % total solids pretreated biomass sample obtained in such a manner as to ensure that it is representative of the entire lot of material being tested.

All lignocellulosic materials which have undergone some aqueous pretreatment must not have undergone any drying prior to enzyme digestibility, since irreversible pore collapse can occur in the micro-structure of the biomass leading to decreased enzymatic release of glucose from the cellulose. Additionally, all frozen lignocellulosic materials which are to be subjected to digestibility tests can not have been frozen for more than one month prior to analysis, since, depending on the environment, sublimation could have occurred leading to possible irreversible collapse of micro-pores in the biomass.

2. Apparatus & Materials

Incubator set at 50±1° C.

Micro-centrifuge pH meter

Analytical balance: sensitive to 0.0001 grams.

HPLC column with refractive index detector and BioRad Aminex® HPX-87P column

Drying oven adjusted to 105±2° C.

A 10, 20, 200 μL, and a 1000 μL, pipetteman with corresponding tips

A pipette tip clipper for sampling high solids slurries 250 ml or 500 mL baffled glass shake flasks equipped with plastic-lined caps or rubber stoppers or drilled rubber stoppers fitted with airlocks or bubble traps 3. Reagents a) Cellulase enzyme (e.g., Celluclast 1.5 L from Novozymes, Accellerase 1000 from Genencor, and 22 CG from Novozymes) of known activity (e.g., FPU/mL). In some cases, a different unit of activity may be specified by the enzyme manufacturer so that the enzyme loadings can be compared on a weight and/or cost basis; b) Sodium citrate buffer (1M, ph 4.8); c) β-glucosidase enzyme of known activity, p-nitrophenyl-glucoside units (pNPGU/mL) (This is only for Celluclast 1.5 L); d) Distilled water or reverse osmosis purified water; e) LACTROL 4. Sample Preparation Determine the Total Solids (TS %/100) for all cellulose containing samples to be digested.

Weigh out about 1 gram of 6 wt % total solids pretreated biomass sample and add to a 250 mL flask. To each flask, add 5.0 mL 1.0 M, pH 4.8 sodium citrate buffer.

To each flask, add 0.5 mg LACTROL to prevent the growth of organisms during the digestion.

Calculate the amount of distilled water needed to bring the total volume in each flask to 100.00 mL after addition of the enzymes specified in the following step. Add the appropriate calculated volume of water to each flask. All solutions and the biomass are assumed to have a specific gravity of 1.000 g/mL. Thus, if 6.0 g of biomass is added to the flask, it is assumed to occupy 6.0 mL and 94 mL of total liquid is to be added.

Bring the contents of each flask to 50° C. by warming in the incubator set at 50±1° C. To each flask is added an appropriate volume of the cellulase enzyme preparation to equal 5 FPU/g glucan (for Celluclast 1.5 L) and the appropriate volume of β-glucosidase enzyme to equal 7.5 p-nitrophenyl-glucoside units (pNPGU)/g glucan for a ratio of 1:1.5 of cellulase to glucosidase. This ratio may not be possible if the two enzymes come premixed in a cocktail so the enzyme loading should be adjusted accordingly. The rate of enzymatic release of glucose is to be measured; all contents of the container prior to the addition of the enzyme must be at 50° C. and pH=4.8. Enzymes are added last since the reaction is initiated by the addition of enzyme.

Prepare a reaction blank for the substrate. The substrate blank contains buffer, water, and the identical amount of substrate in a 100.00 mL volume.

Prepare enzyme blanks for cellulase and β-glucosidase with buffer, water, and the identical amount of the enzyme.

Close the vials tightly and incubate with gentle rotation (150 RPM) for a period of 72 to 110 hours or until the release of soluble sugars from the sample(s) becomes negligible.

If the progress of the reaction is to be measured, a 0.3-0.5 mL aliquot is removed at each predetermined time interval (0, 6, 12, 24, 48, 72, 96 hrs) after the vial contents have been well mixed by shaking. The sample is heated at 100° C. for 10 minutes to inactivate the enzyme, the sample is the cooled down and expelled into a 1.5 mL microcentrifuge tube and centrifuged for 5 minutes. The supernatant is subjected to glucose analysis using HPLC.

5. Calculations

To calculate the percent digestibility of the cellulose added to the container, determine glucose concentration in the centrifuged supernatant by HPLC. Subtract the glucose concentrations, if any, from the substrates and enzyme blanks. Correct for hydration by multiplying the glucose reading by 0.9 to correct for the water molecule added upon hydrolysis of the cellulose polymer and multiply by 100 mL total volume of assay.

Example: If the glucose analyzer reading (corrected with blanks) is 9.9 mg/mL, then the amount of glucan digested is: 0.0099 g/mL×100 mL×0.9=0.891 g Calculate Cellulose Digestibility:

$$\text{Cellulose Digestibility}(\%) = 100\% \times (\text{Gram Cellulose Digested/Grams Cellulose Added})$$

6. Notes and Precautions

Report the results to two decimal places, on a 105° C. dry basis. For replicate analyses of the same sample, report the average, standard deviation and relative percent difference (% RPD).

b) Relative percent difference criteria: Not defined; depend on the substrate being tested. Different preparations of pretreated biomass will exhibit different amount of homogeneity, which will influence the extent to which they are hydrolyzed.

Sample storage: Store pretreated samples should be stored moist, frozen in a well sealed container or vacuum packed not longer than three months.

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and applicants intend each of those words to be so interpreted in construing this entire specification.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for pretreatment of cellulosic biomass feedstock comprising cellulose, hemicellulose, and lignin, the method comprising:

contacting the cellulosic biomass feedstock with an acidic liquid medium to form an acid-impregnated biomass feedstock;

contacting the acid-impregnated cellulosic biomass feedstock with $H_2O$ at elevated temperature and pressure within a contact zone under conditions effective for solubilizing hemicellulose and producing a steam treated feedstock, wherein the pressure in the contact zone is at least about 55 psig;

subjecting the steam treated feedstock within a depressurization zone to conditions and for at time effective for solubilizing hemicellulose and producing a volatilized fraction of the steam treated feedstock; and releasing at least a portion of the volatilized fraction from the depressurization zone for control of temperature and pressure within the depressurization zone, wherein the pressure within the depressurization zone is controlled to from about 5 to about 50 psig.

2. The method of claim 1 wherein the acid-impregnated cellulosic biomass feedstock is contacted with $H_2O$ in the contact zone as saturated steam at a pressure of from about 75 psig to about 250 psig.

3. The method of claim 1 wherein the acid-impregnated cellulosic biomass feedstock is contacted with $H_2O$ in the contact zone as saturated steam at a temperature of from about 160° C. to about 230° C.

4. The method of claim 1 wherein the acid-impregnated cellulosic biomass feedstock is contacted with $H_2O$ in the contact zone as saturated steam for from about 1 to about 15 minutes.

5. The method of claim 1 wherein the depressurization zone temperature is from about 110° C. to about 150° C.

6. The method of claim 1 wherein the pressure within the depressurization zone is from about 5 psig to about 40 psig and the temperature is from about 110° C. to about 140° C.

7. The method of claim 1 wherein the pressure within the depressurization zone is from about 10 psig to about 15 psig and the temperature is from about 110° C. to about 120° C.

8. The method of claim 1 wherein the steam treated feedstock is subjected to conditions effective for solubilizing hemicellulose and producing a volatilized fraction of the steam treated feedstock in the depressurization zone for from about 2 to about 30 minutes.

9. The method of claim 1 wherein the steam treated feedstock within the contact zone comprises a liquid fraction comprising xylose and the steam treated feedstock within the depressurization zone comprises a liquid fraction comprising xylose, and wherein the xylose content of the liquid fraction of the steam treated feedstock within the depressurization zone represents a xylose yield of at least about 60%.

10. The method of claim 9 wherein the xylose content of the liquid fraction of the steam treated feedstock within the depressurization zone represents a xylose yield of at least about 70%.

11. The method of claim 9 wherein the xylose content of the liquid fraction in the depressurization zone is at least about 5% higher than the xylose content of the liquid fraction in the contact zone.

12. The method of claim 1 wherein the volatilized fraction of the steam treated feedstock released from the depressurization zone comprises furfural, acetic acid, steam, or a combination thereof.

13. The method of claim 1 wherein the method comprises:
continuously contacting the acid-impregnated cellulosic biomass feedstock with $H_2O$ in the contact zone;
continuously subjecting the steam treated feedstock to the conditions within the depressurization zone; and
continuously releasing at least a portion of the volatilized fraction from the depressurization zone.

14. The method of claim 1 wherein the contact zone and depressurization zone are contained within a single vessel.

15. The method of claim 1 wherein the contact zone and depressurization zone are contained within separate vessels.

16. The method of claim 1 wherein the contact zone comprises a first pretreatment stage and a second pretreatment stage wherein, in the second pretreatment stage, at least a portion of the volatilized fraction is released from the contact zone at a rate effective to control the pressure in the contact zone, wherein the pressure in the second pretreatment stage is reduced by at least 30 psig as compared to the pressure in the first pretreatment stage.

17. A method for pretreatment of cellulosic biomass feedstock comprising cellulose, hemicellulose, and lignin, the method comprising:
contacting the cellulosic biomass feedstock with an acidic liquid medium to form an acid-impregnated cellulosic biomass feedstock;
in a first pretreatment stage, contacting the acid-impregnated cellulosic biomass feedstock with $H_2O$ at elevated temperature within a contact zone containing a vapor phase wherein the partial pressure of water vapor is at least about 55 psig to solubilize hemicellulose and produce a volatilized fraction of the acid-impregnated feedstock; and
in a second pretreatment stage, releasing at least a portion of the volatilized fraction from the contact zone at a rate effective to control the pressure of in the contact zone, wherein the pressure in the second pretreatment stage is reduced by at least about 30 psig as compared to the first pretreatment stage pressure, the pressure in the second pretreatment stage is controlled above atmospheric pressure, and the acid-impregnated feedstock is held in the second pretreatment stage for a time effective for solubilizing hemicellulose and producing a volatilized fraction of the steam treated feedstock.

18. The method of claim 17 wherein the volatilized fraction comprises acetic acid, furfural, hydroxymethyl furfural, condensable gases, or a combination thereof.

19. The method of claim 17 wherein the acid impregnated cellulosic biomass in the first pretreatment stage and the second pretreatment stage comprises a liquid fraction comprising xylose, wherein the xylose content of the liquid fraction in the second pretreatment stage is at least about 5% higher than the xylose content of the liquid fraction in the first pretreatment stage.

20. The method of claim 17 wherein the first pretreatment stage pressure is at least about 150 psig.

21. The method of claim 17 wherein the second pretreatment stage pressure is from about 25 psig to about 150 psig.

22. The method of claim 17 wherein the first pretreatment stage temperature is from about 160° C. to about 220° C.

23. The method of claim 17 wherein the second pretreatment stage temperature is from about 130° C. to about 185° C.

24. The method of claim 17 wherein the second pretreatment stage hold time is from about 0.1 to about 5 minutes.

25. The method of claim 17 further comprising treating the acid-impregnated feedstock from the second pretreatment stage steam treated feedstock within a depressurization zone to conditions and for at time effective for solubilizing hemicellulose and producing a volatilized fraction of the steam treated feedstock; and
releasing at least a portion of the volatilized fraction from the depressurization zone for control of temperature and pressure within the depressurization zone, wherein control of the temperature and pressure within the depressurization zone comprises releasing at least a portion of the volatilized fraction therefrom, wherein the pressure within the depressurization zone is controlled to from about 5 to about 50 psig.

26. A method for pretreatment of cellulosic biomass feedstock comprising cellulose, hemicellulose, and lignin, the method comprising:

introducing said feedstock into a steam contact zone, said contact zone having an inlet for steam and an outlet for pretreated feedstock;

introducing steam into said contact zone at said inlet to contact steam and said feedstock and form a steam treated feedstock, wherein the pressure in the contact zone is at least about 51) psig; and removing pretreated feedstock from said contact zone through said outlet and into a receiving zone, wherein the pressure in the receiving zone does not differ from the pressure in the contact zone by more than about 200 psig, the pressure in the receiving zone is controlled above atmospheric pressure, and the pretreated feedstock is held in the receiving zone for a time effective for solubilizing hemicellulose and producing a volatilized fraction of the steam treated feedstock.

27. A method as set forth in claim 26 wherein the pressure within said contact zone is at least about 100 psig.

28. The method of claim 26 wherein the acid impregnated cellulosic biomass in the contact zone and receiving zone comprises a liquid fraction comprising xylose, wherein the xylose content of the liquid fraction in the receiving zone is at least about 5% higher than the xylose content of the liquid fraction in the contact zone.

29. The method of claim 26 wherein the contact zone pressure is at least about 150 psig.

30. The method of claim 26 wherein the receiving zone pressure is from about 25 psig to about 150 psig.

31. The method of claim 26 wherein the contact zone temperature is from about 160° C. to about 220° C.

32. The method of claim 26 wherein the receiving zone temperature is from about 130° C. to about 185° C.

33. The method of claim 26 wherein the receiving zone hold time is from about 0.1 to about 5 minutes.

34. A method for pretreatment of cellulosic biomass feedstock comprising cellulose, hemicellulose, and lignin, the method comprising:

introducing said feedstock into a steam contact zone;

introducing steam into said contact zone to contact said feedstock and form a steam-treated feedstock, wherein the pressure in the contact zone is at least about 51) psig; and passing said steam-treated feedstock from said steam contact zone through a flow restriction and into a receiving zone, the pressure drop across said flow restriction being less than about 150 psi, the pressure in the receiving zone is controlled above atmospheric pressure, and the steam-treated feedstock is held in the receiving zone for a time effective for solubilizing hemicellulose and producing a volatilized fraction of the steam treated feedstock.

35. The method of claim 34 wherein the acid impregnated cellulosic biomass in the contact zone and receiving zone comprises a liquid fraction comprising xylose, wherein the xylose content of the liquid fraction in the receiving zone is at least about 5% higher than the xylose content of the liquid fraction in the contact zone.

36. The method of claim 34 wherein the contact zone pressure is at least about 150 psig.

37. The method of claim 34 wherein the receiving zone pressure is from about 25 psig to about 150 psig.

38. The method of claim 34 wherein the contact zone temperature is from about 160° C. to about 220° C.

39. The method of claim 34 wherein the receiving zone temperature is from about 130° C. to about 185° C.

40. The method of claim 34 wherein the receiving zone hold time is from about 0.1 to about 5 minutes.

41. A method for pretreatment of cellulosic biomass feedstock comprising cellulose, hemicellulose, and lignin, the method comprising:

in a first pretreatment stage, contacting the cellulosic biomass feedstock with H20 within a contact zone containing a vapor phase wherein the partial pressure of water vapor is at least about 55 psig, said H20 being distributed within said zone so that the biomass is brought to a target temperature, and the average temperature of any region of the biomass that contains more than 15% by weight of the biomass does not differ by more than 5° C. from said target temperature, and in a second pretreatment stage, reducing the pressure by at least 31) psig as compared to the first pretreatment stage pressure, the pressure in the second pretreatment stage is controlled above atmospheric pressure, and the feedstock-is held in the second pretreatment stage for a time effective for solubilizing hemicellulose and producing a volatilized fraction of the steam treated feedstock.

42. The method of claim 41 wherein the average temperature of any region of biomass that contains more than about 10% by weight of the biomass does not differ by more than 5° C. from said target temperature.

43. The method of claim 41 wherein the acid impregnated cellulosic biomass in the first pretreatment stage and the second pretreatment stage comprises a liquid fraction comprising xylose, wherein the xylose content of the liquid fraction in the second pretreatment stage is at least about 5% higher than the xylose content of the liquid fraction in the first pretreatment stage.

44. The method of claim 41 wherein the first pretreatment stage pressure is at least about 150 psig.

45. The method of claim 41 wherein the second pretreatment stage pressure is from about 25 psig to about 150 psig.

46. The method of claim 41 wherein the first pretreatment stage temperature is from about 160° C. to about 220° C.

47. The method of claim 41 wherein the second pretreatment stage temperature is from about 130° C. to about 185° C.

48. The method of claim 41 wherein the second pretreatment stage hold time is from about 0.1 to about 5 minutes.

* * * * *